US010385337B2

(12) United States Patent
Manoharan et al.

(10) Patent No.: US 10,385,337 B2
(45) Date of Patent: Aug. 20, 2019

(54) OLIGONUCLEOTIDE END CAPS

(71) Applicant: Alnylam Pharmaceuticals, Inc., Cambridge, MA (US)

(72) Inventors: Muthiah Manoharan, Cambridge, MA (US); Kallanthottathil G. Rajeev, Cambridge, MA (US)

(73) Assignee: Alnylam Pharmaceuticals, Inc., Cmabridge, MA (US)

( * ) Notice: Subject to any disclaimer, the term of this patent is extended or adjusted under 35 U.S.C. 154(b) by 197 days.

(21) Appl. No.: 15/334,019

(22) Filed: Oct. 25, 2016

(65) Prior Publication Data

US 2017/0107511 A1    Apr. 20, 2017

Related U.S. Application Data

(63) Continuation of application No. 13/382,353, filed as application No. PCT/US2010/041215 on Jul. 7, 2010, now Pat. No. 9,512,164.

(60) Provisional application No. 61/223,665, filed on Jul. 7, 2009.

(51) Int. Cl.
| *C07H 21/04* | (2006.01) |
| *C12N 15/113* | (2010.01) |
| *C07H 21/02* | (2006.01) |
| *C12N 15/115* | (2010.01) |
| *C12N 15/82* | (2006.01) |

(52) U.S. Cl.
CPC .......... *C12N 15/113* (2013.01); *C07H 21/02* (2013.01); *C07H 21/04* (2013.01); *C12N 15/115* (2013.01); *C12N 15/8222* (2013.01); *C12N 2310/14* (2013.01); *C12N 2310/16* (2013.01); *C12N 2310/31* (2013.01); *C12N 2310/317* (2013.01); *C12N 2310/344* (2013.01)

(58) Field of Classification Search
None
See application file for complete search history.

(56) References Cited

U.S. PATENT DOCUMENTS

| 6,605,708 B1 | 8/2003 | Habus et al. |
| 2005/0261218 A1 | 11/2005 | Esau et al. |
| 2006/0276422 A1* | 12/2006 | Usman ............... C12N 15/1138 514/44 A |
| 2011/0039259 A1 | 2/2011 | Ju et al. |

FOREIGN PATENT DOCUMENTS

| WO | 9202534 | 2/1992 |
| WO | 9205186 | 4/1992 |
| WO | 9504066 | 2/1995 |
| WO | 2007084865 | 7/2007 |

OTHER PUBLICATIONS

Hebb et al. Molecular Brain Research (1997), vol. 47, pp. 223-228.*
Sengupta et al. J. Org. Chem. (2008), vol. 73, pp. 6860-6863.*
Beaucage, Serge L. et al., "The Functionalization of Oligonucleotides Via Phosphoramidite Derivatives" Tetrahedron, Elsevier Science Publishers, Tetrahedron 49, 10:1925-1963, (1993).
Shaw, Jeng-Pyng et al., "Modified Deoxyoligonucleotides Stable to Exonuclease Degradation in Serum" Oxford University 1991, Press Nucleic Acids Research 19, 4:747-750 (1991).
Prabahar, K. Joseph et al. Effect of Phosphate Activating Group on Oligonucleotide Formation on Montmorillonite: The Regioselective Formation of 3',5'-Linked Oligoadenylates, J. Am. Chem. Soc., 116:10914-10920 (1994).

* cited by examiner

*Primary Examiner* — Patrick T Lewis
(74) *Attorney, Agent, or Firm* — Jeffrey N. Townes; Cozen O'Connor

(57) ABSTRACT

Modified nucleic acids are described herein, including pharmaceutical compositions comprising the modified nucleic acids, and methods of using the modified nucleic acids.

13 Claims, 6 Drawing Sheets

OLIGONUCLEOTIDE END CAPS

PRIORITY

This application is a continuation application of U.S. patent application Ser. No. 13/382,353, filed Feb. 22, 2012, which claims priority to PCT Application No. PCT/US2010/041215, filed Jul. 7, 2010, which claims benefit of priority to U.S. Provisional Application No. 61/223,665, filed Jul. 7, 2009, all of which are herein incorporated by reference in their entirety.

TECHNICAL FIELD

Described herein are modified nucleic acids designed to increase the half-life of oligonucleotides, as well as increasing their effectiveness in inhibiting expression or activity of a target gene.

BACKGROUND

Oligonucleotides and their analogs have been developed for various uses in molecular biology, including uses as probes, primers, linkers, adapters, and gene fragments. In a number of these applications, the oligonucleotides specifically hybridize to a target nucleic acid sequence. Hybridization is the sequence specific hydrogen bonding of oligonucleotides via Watson-Crick and/or Hoogsteen base pairs to RNA or DNA. The bases of such base pairs are said to be complementary to one another.

Double-stranded RNA molecules (dsRNAs) can block gene expression by virtue of a highly conserved regulatory mechanism known as RNA interference (RNAi). Briefly, the RNA III Dicer enzyme processes dsRNA into small interfering RNAs (also sometimes called short interfering RNAs or siRNAs) of approximately 22 nucleotides. One strand of the siRNA (the "antisense strand") then serves as a guide sequence to induce cleavage of messenger RNAs (mRNAs) including a nucleotide sequence which is at least partially complementary to the sequence of the antisense strand by an RNA-induced silencing complex, RISC. The antisense strand is not cleaved or otherwise degraded in this process, and the RISC including the antisense strand can subsequently affect the cleavage of further mRNAs.

It is desirable that oligonucleotides be able to be synthesized to have customized properties that are tailored for desired uses. Thus a number of chemical modifications have been introduced into oligonucleotides to increase their usefulness in diagnostics, as research reagents and as therapeutic entities. (Chemically modified oligonucleotides include, for example, pseudouridine derivatives and lipid-containing oligonucleotides.) Such modifications include those designed to increase binding to a target strand (i.e., increase their melting temperatures, $T_m$), to assist in identification of the oligonucleotide or an oligonucleotide-target complex, to increase cell penetration, to stabilize against nucleases and other enzymes that degrade or interfere with the structure or activity of the oligonucleotides, to provide a mode of disruption (a terminating event) once sequence-specifically bound to a target, and to improve the pharmacokinetic properties of the oligonucleotide.

Even given the advances that have already been made in the art, there remains an ongoing need for new modifications designed to, for example, increase the resistance of oligonucleotides to chemical and/or nuclease digestion, increase the half-life of a nucleic acid agent, or to reduce off-target effects.

SUMMARY OF THE INVENTION

Provided herein are end caps that can be used to improve the resistance of oligonucleotides to chemical and/or nuclease digestion, and thus increased stability in biological samples and a longer in vivo half-life. Increasing the in vivo half-life of the oligonucleotides results in enhanced bioavailability, and hence improved effectiveness in inhibiting expression or activity of a target gene.

Provided herein are non-nucleosidic end caps comprising formula (I), (II) or (III) and methods for preparing them. The nucleosidic end caps may be attached to the 3' end, 2' end or the 5' end of the strand.

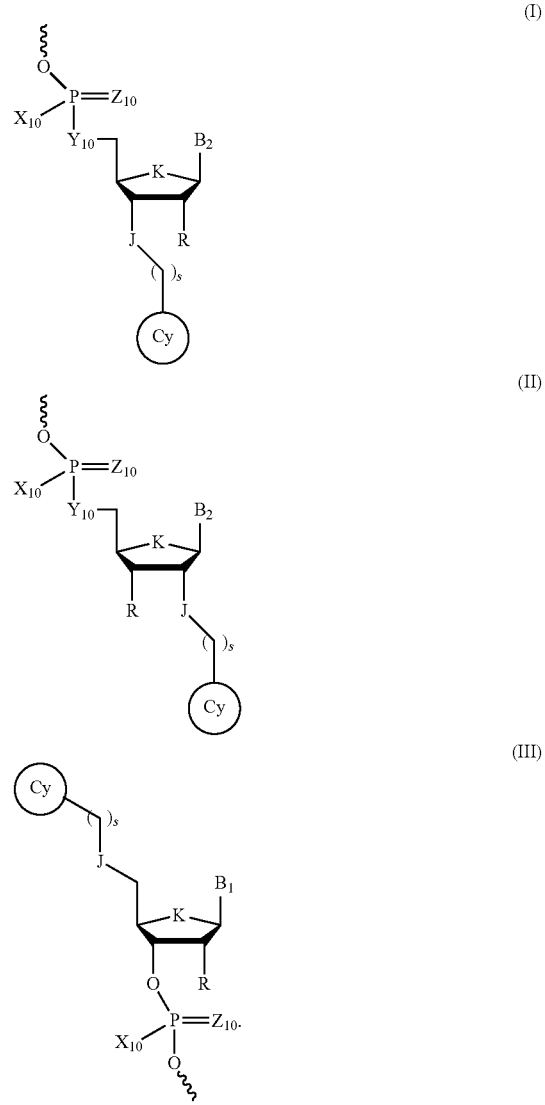

DETAILED DESCRIPTION

Figure 1A:
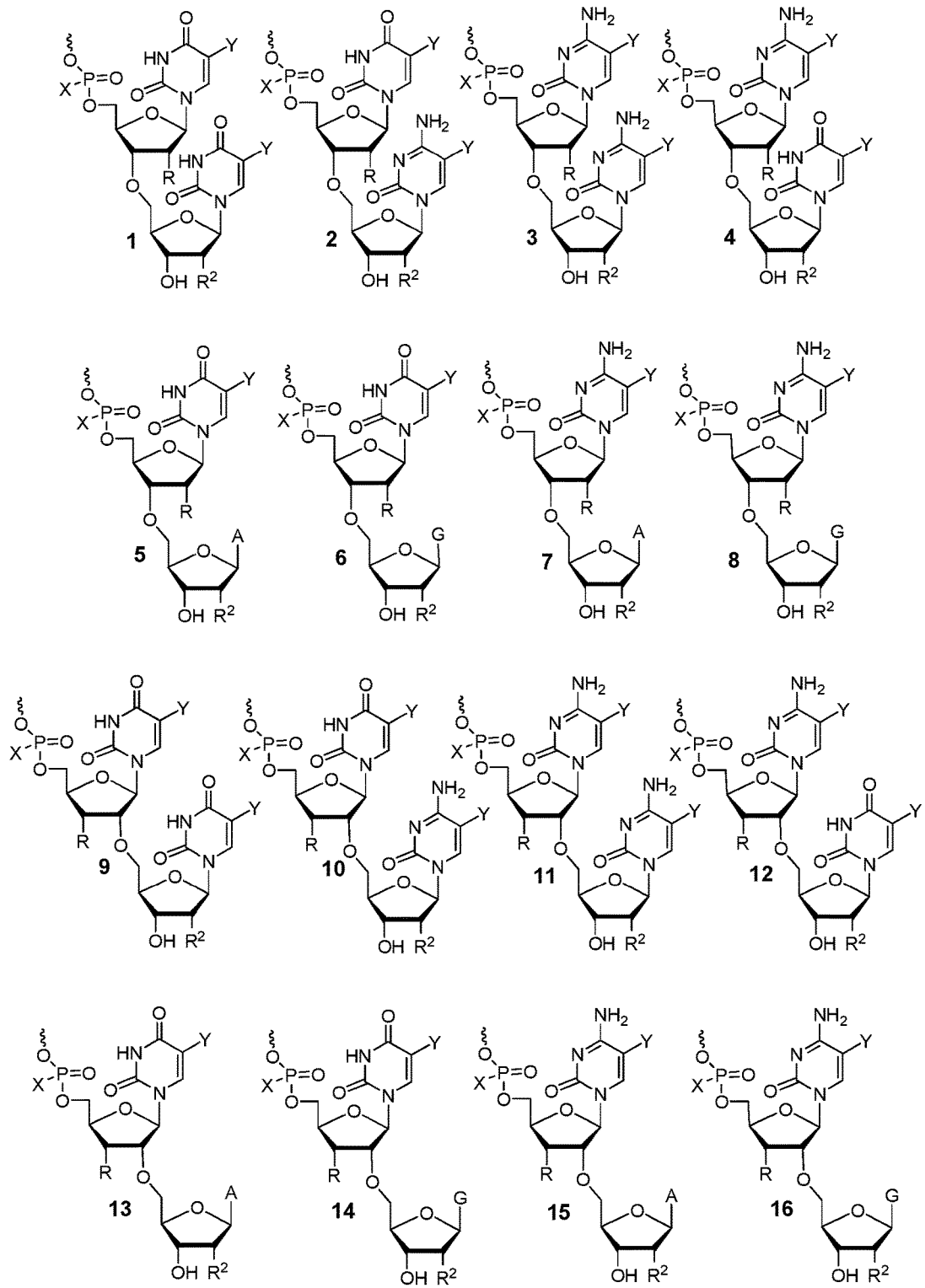
FIG. 1A-1F depict exemplary modified nucleic acids, wherein each Y is independently H or $CH_3$; each X is independently O or S; each R is independently H, OH, $OCH_3$, F or $O(CH_2)_2OCH_3$; each $R^2$ is independently hydrogen, $C_1$-$C_{32}$ alkyl, $C_1$-$C_{32}$ alkoxy, —$(CH_2)_n$—$NR^bR^c$, —O(CH$_2$)$_n$—NR$^b$R$^c$, —[O(CH$_2$)$_r$]$_m$—OR$^b$, —[O(CH$_2$)]$_m$—NR$^b$R$^c$, —(CH$_2$)$_n$—O—NR$^b$R$^c$, —O—(CH$_2$)$_n$—O—NR$^b$R$^c$, —[O(CH$_2$)$_r$]$_m$—O—NR$^b$R$^c$, —(CH$_2$)$_n$—N(R$^b$)—C(=NR$^b$)—NR$^b$R$^c$, —O—(CH$_2$)$_n$—NR$^b$—C(=NR$^b$)—NR$^b$R$^c$, —[O(CH$_2$)$_r$]$_m$—N(R$^b$)—C(=NR$^b$)—NR$^b$R$^c$, —(CH$_2$)$_n$—O—NR$^b$—C(=NR$^b$)—NR$^b$R$^c$, —O—(CH$_2$)$_n$—O—NR$^b$—C(=NR$^b$)—NR$^b$R$^c$, or —[O(CH$_2$)$_r$]$_m$—O—NR$^b$—C(=NR$^b$)—NR$^b$R$^c$; R$^4$ is hydrogen, C$_1$-C$_{32}$ alkyl, —C(X$_1$)—(CH$_2$)$_n$—H, —C(X$_1$)Y$_1$—(CH$_2$)$_n$—H, —C(X$_1$)N(R$^b$)—(CH$_2$)$_n$—H, —(CH$_2$)$_n$—NR$^b$R$^c$, —C(X)—(CH$_2$)$_n$—NR$^b$R$^c$, —C(X$_1$)Y$_1$—(CH$_2$)$_n$—NR$^b$R$^c$, —C(X$_1$)N(R$^b$)—(CH$_2$)$_n$—NR$^b$R$^c$, —(CH$_2$)$_n$—N(R$^b$)—C(=NR$^b$)—NR$^b$R$^c$, —C(X$_1$)—(CH$_2$)$_n$—N(R$^b$)—C(=NR$^b$)—NR$^b$R$^c$, —C(X$_1$)Y$_1$—(CH$_2$)$_n$—N(R$^b$)—C(=NR$^b$)—NR$^b$R$^c$ or —C(X$_1$)N(R$^b$)—(CH$_2$)$_n$—N(R$^b$)—C(=NR$^b$)—NR$^b$R$^c$; n is 1-20; r is 1-20; m is 0-20; X$_1$ is O or S; Y$_1$ is absent, O, or N(R$^b$), and each R$^b$ and R$^c$ is independently hydrogen or C$_1$-C$_{32}$ alkyl.

Described herein are modified nucleic acid agents. Exemplary nucleic acids include those described herein, e.g., single-stranded nucleic acid agents and double-stranded nucleic acid agents.

A nucleic acid agent may be modified at either the 5' end, 2' end or the 3' end of the strand with an end cap, e.g., as provided in formula (I), (II) and formula (III), provided that

is not

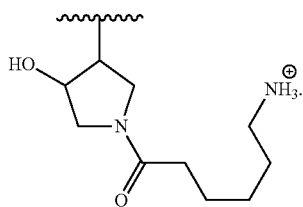

In some embodiments, the nucleic acid is modified at both of the 5' end and 3'end. The end cap may be a nucleosidic end cap or a non-nucleosidic end-cap (e.g., an end cap based on a pyrrolidine ring). The end cap may be attached to the strand via a variety of linkers, such as phosphodiester, sulfur, amino, ester, carbamate or ether linkages. The end cap may be linked to the strand through a variety of positions on the end cap. For example, when an agent is modified at the 5' end of the agent, the end cap may be linked to the strand via the 2' or the 3' position of the end cap. When an agent is modified at the 3' end of the agent, the end cap may be linked to the strand via the 5' position of the end cap.

A nucleic acid agent described herein may have a modification which, in some embodiments, may slow or prevent degradation of the agent by an exonuclease (e.g., a 5'-exonuclease or a 3'-exonuclease). This may increase the half-life of the agent, e.g., in serum or in liver homogenates. A nucleic acid agent modified as described herein (e.g., with an end cap described herein), may have an increase in half-life relative to an unmodified nucleic acid agent or even a modified agent such as a nucleic acid agent modified with a phosphorthioate linkage (e.g., a nucleic acid agent modified at the 3'end). The half-life of a nucleic acid agent can be evaluated using methods known in the art. For example, the half-life of the nucleic acid agent can be evaluated in serum or using liver homogenate.

In some embodiments, the nucleic acid agent modified as described herein has a half-life in serum (e.g., rat serum) of at least about 2 hours, e.g., at least about 3 hours, at least about 4 hours, at least about 5 hours, at least about 6 hours, at least about 8 hours, at least about 10 hours, or at least about 12 hours. In some embodiments, the nucleic acid agent modified as described herein has a half-life in liver homogenate (e.g., rat serum) of at least about 2 hours, e.g., at least about 3 hours, at least about 4 hours, at least about 5 hours, at least about 6 hours, at least about 8 hours, at least about 10 hours, at least about 12 hours, or at least about 24 hours.

In some embodiments, a nucleic acid agent as modified herein has reduced off-target effects, for example, relative to an unmodified nucleic acid agent or a nucleic acid agent without an end cap modification as described herein (e.g., as provided in formula of the invention). The term "off-target" and the phrase "off-target effects" refer to any instance in which an RNAi agent against a given target causes an unintended affect by interacting either directly or indirectly with another mRNA sequence, a DNA sequence or a cellular protein or other moiety. For example, an "off-target effect" may occur when there is a simultaneous degradation of other transcripts due to partial homology or complementarity between that other transcript and the sense and/or antisense strand of a double-stranded RNAi agent.

A nucleosidic end cap may be attached to the 3' end of the strand to either the 3' or 2' position of the ribo sugar via a J linker, such as in the following:

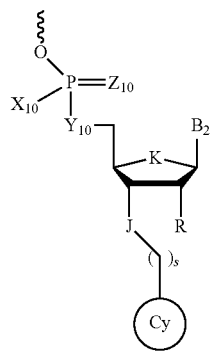

attached at 3' position

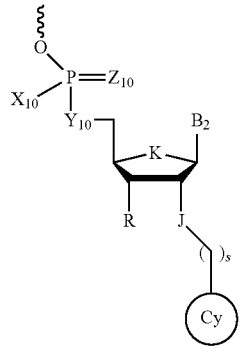

attached at 2' position wherein J is an ether, sulfide, amino, ester, sulfonamide, amide, urea, carbamate or a phosphorus containing linkage;

K is independently O, S, NR', optionally substituted alkyl in each occurrence, where R' is hydrogen, acyl, aliphatic or substituted aliphatic;

$B^1$ and $B^2$ are natural or modified nucleobases;

$X_{10}$ is H, OH, OM, SH, SM, optionally substituted alkyl, optionally substituted alkoxy, optionally substituted alkylthio, optionally substituted alkylamino, optionally substituted dialkylamino, where M represents independently for each occurrence an alkali metal or a transition metal with an overall charge of +1;

$Z_{10}$ is O, S or NR';

$Y_{10}$ is O, S or NR';

R is each independently H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino; s is 0-10; and Cy is a substituted or unsubstituted heteroaryl, a substituted or unsubstituted heterocyclic, a substituted or unsubstituted aryl, a substituted or unsubstituted cycloalkyl; and provided that when

is a ribo, J is not a phosphorus containing linkage.

In one example,

is piperazinyl, pyrrolidinyl, dioxanyl, morpholinyl or tetrahydrofuranyl.

The remainder of the oligonucleotide may be attached through the oxygen with the open bond, i.e. through the

in the above formulas.

A nucleosidic end cap may be attached to the 3' end of the strand to either the 3' or 2' position of the ribo sugar via an ether linkage, such as in the following:

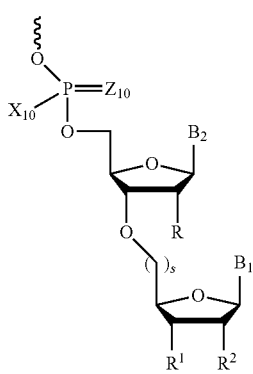

attached at 3' position

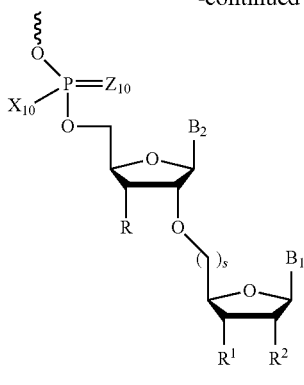

attached at 2' position wherein $B^1$ and $B^2$ are natural or modified nucleobases;

$X_{10}$ is H, OH, OM, SH, SM, optionally substituted alkyl, optionally substituted alkoxy, optionally substituted alkylthio, optionally substituted alkylamino, optionally substituted dialkylamino, where M represents independently for each occurrence an alkali metal or a transition metal with an overall charge of +1;

$Z_{10}$ is O, S or NR', where R' is hydrogen, acyl, aliphatic or substituted aliphatic;

R, $R^1$ or $R^2$ is each independently H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino; and s is 0-10.

In one embodiment, R is independently H, OH, OMe, F or $O(CH_2)_2OMe$; each $R^1$ or $R^2$ is independently hydrogen, OH, F, $C_1$-$C_{32}$ alkyl, $C_1$-$C_{32}$ alkoxy, —$(CH_2)_n$—$NR^bR^c$, —$O(CH_2)_n$—$NR^bR^c$, —$[O(CH_2)_r]_m$—$OR^b$, —$[O(CH_2)_r]_m$—$NR^bR^c$, —$(CH_2)_n$—O—$NR^bR^c$, —O—$(CH_2)_n$—O—$NR^bR^c$, —$[O(CH_2)_r]_m$—O—$NR^bR^c$, —$(CH_2)_n$—$N(R^b)$—$C(=NR^b)$—$NR^bR^c$, —O—$(CH_2)_n$—$NR^b$—$C(=NR^b)$—$NR^bR^c$, —$[O(CH_2)_r]_m$—$N(R^b)$—$C(=NR^b)$—$NR^bR^c$, —$(CH_2)_n$—O—$NR^b$—$C(=NR^b)$—$NR^bR^c$, —O—$(CH_2)_n$—O—$NR^b$—$C(=NR^b)$—$NR^bR^c$, or —$[O(CH_2)_r]_m$—O—$NR^b$—$C(=NR^b)$—$NR^bR^c$; and each $R^b$ and $R^c$ is independently hydrogen or $C_1$-$C_{32}$ alkyl; X is O or S; and n, m or r are each independently 1-20.

A modified agent may have a non-nucleosidic end cap at the 3' end of the strand, which may be based, for example, on a pyrrolidine ring.

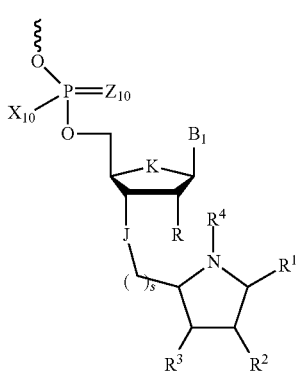

attached at 3' position

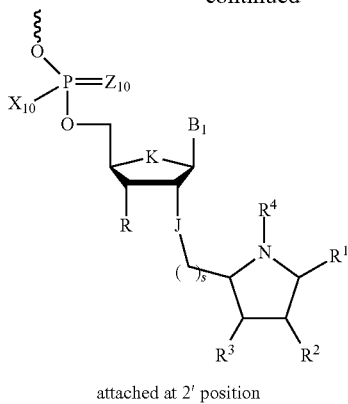

attached at 2' position

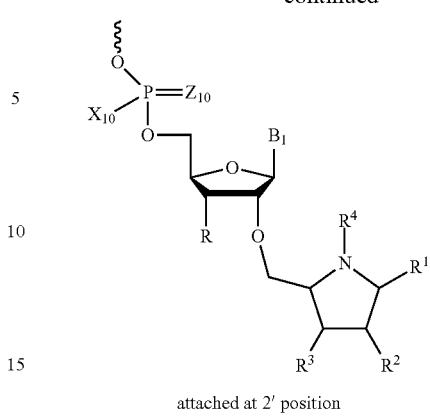

attached at 2' position wherein J is an ether, sulfide, amino, ester, sulfonamide, amide, urea, carbamate or a phosphorus containing linkage;

K is independently O, S, NR', optionally substituted alkyl in each occurrence, where R' is hydrogen, acyl, aliphatic or substituted aliphatic;

$B^1$ and $B^2$ are natural or modified nucleobases;

$X_{10}$ is H, OH, OM, SH, SM, optionally substituted alkyl, optionally substituted alkoxy, optionally substituted alkylthio, optionally substituted alkylamino, optionally substituted dialkylamino, where M represents independently for each occurrence an alkali metal or a transition metal with an overall charge of +1;

$Z_{10}$ is O, S or NR';

$Y_{10}$ is O, S or NR'; each of R, $R^1$, $R^2$ or $R^4$ is each independently H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino;

s is 0-7; and $R^4$ is hydrogen, optionally substituted alkyl, optionally substituted acyl, optionally substituted sulfonamide.

A non-nucleosidic end cap may be attached to the strand at either the 3' or 2' position of the strand via a phosphodiester linkage, such as in the following examples:

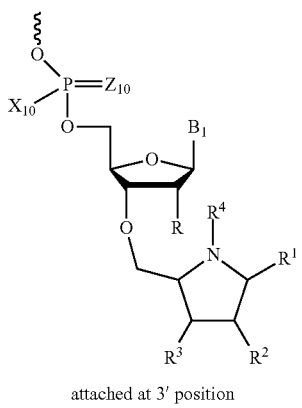

attached at 3' position wherein $B^1$ is a natural or modified nucleobase;

R is H, OH, OMe, F, or $O(CH_2)_n(Z)(CH_2)_m$—H, where n is 1-20, m is 0-20, and Z is O or S;

$X_{10}$ is H, OH, OM, SH, SM, optionally substituted alkyl, optionally substituted alkoxy, optionally substituted alkylthio, optionally substituted alkylamino, optionally substituted dialkylamino, where M represents independently for each occurrence an alkali metal or a transition metal with an overall charge of +1;

$Z_{10}$ is O, S or NR', where R' is hydrogen, acyl, aliphatic or substituted aliphatic; each $R^1$, $R^2$ and $R^3$ is independently H, F, hydroxyl, alkoxy, amino, alkylamino or dialkylamino; and $R^4$ is hydrogen, $C_1$-$C_{32}$ alkyl, —C(X)—$(CH_2)_n$—H, —C($X_1$)$Y_1$—$(CH_2)_n$—H, —C($X_1$)N($R^b$)—$(CH_2)_n$—H, —$(CH_2)_n$—$NR^bR^c$, —C($X_1$)—$(CH_2)_n$—$NR^bR^c$, —C($X_1$)$Y_1$—$(CH_2)_n$—$NR^bR^c$, —C($X_1$)N($R^b$)—$(CH_2)_n$—$NR^bR^c$, —$(CH_2)_n$—N($R^b$)—C(=$NR^b$)—$NR^bR^c$, —C($X_1$)—$(CH_2)_n$—N($R^b$)—C(=$NR^b$)—$NR^bR^c$, —C($X_1$)$Y_1$—$(CH_2)_n$—N($R^b$)—C(=$NR^b$)—$NR^bR^c$ or —C($X_1$)N($R^b$)—$(CH_2)_n$—N($R^b$)—C(=$NR^b$)—$NR^bR^c$, where n is 1-20; m is 0-20; $X_1$ is O or S; $Y_1$ is absent, O, or N($R^b$), and each $R^b$ and $R^c$ is independently hydrogen or $C_1$-$C_{32}$ alkyl.

A non-nucleosidic end cap may be attached to the 3' end of the strand at either the 3' or 2' position of the strand via an ether linkage, such as in the following examples:

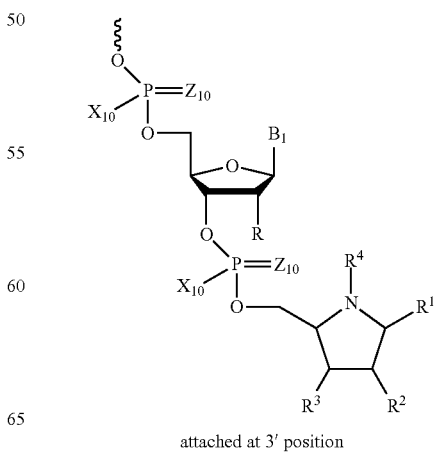

attached at 3' position

-continued

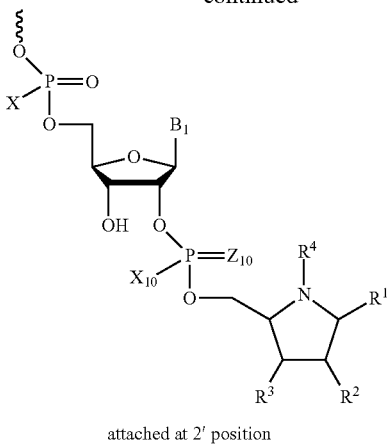

attached at 2' position wherein $B^1$ is a natural or modified nucleobase;

R is H, OH, OMe, F, or $O(CH_2)_n(Z)(CH_2)_m$—H, where n is 1-20, m is 0-20, and Z is O or S;

each of $X_{10}$ is independently H, OH, OM, SH, SM, optionally substituted alkyl, optionally substituted alkoxy, optionally substituted alkylthio, optionally substituted alkylamino, optionally substituted dialkylamino, where M represents independently for each occurrence an alkali metal or a transition metal with an overall charge of +1;

each of $Z_{10}$ is independently O, S or NR', where R' is hydrogen, acyl, aliphatic or substituted aliphatic;

$R^4$ is hydrogen, $C_1$-$C_{32}$ alkyl, —C(X)—$(CH_2)_n$—H, —C($X_1$)$Y_1$—$(CH_2)_n$—H, —C($X_1$)N($R^b$)—$(CH_2)_n$—H, —$(CH_2)_n$—$NR^bR^c$, —C($X_1$)—$(CH_2)_n$—$NR^bR^c$, —C($X_1$)$Y_1$—$(CH_2)_n$—$NR^bR^c$, —C($X_1$)N($R^b$)—$(CH_2)_n$—$NR^bR^c$, —$(CH_2)_n$—N($R^b$)—C(=$NR^b$)—$NR^bR^c$, —C($X_1$)—$(CH_2)_n$—N($R^b$)—C(=$NR^b$)—$NR^bR^c$, —C($X_1$)$Y_1$—$(CH_2)_n$—N($R^b$)—C(=$NR^b$)—$NR^bR^c$ or —C($X_1$)N($R^b$)—$(CH_2)_n$—N($R^b$)—C(=$NR^b$)—$NR^bR^c$, where n is 1-20; m is 0-20; $X_1$ is O or S; $Y_1$ is absent, O, or N($R^b$), and each $R^b$ and $R^c$ is independently hydrogen or $C_1$-$C_{32}$ alkyl.

A nucleosidic end cap may be attached to the 5' end of the strand via a J linker, such as in the following:

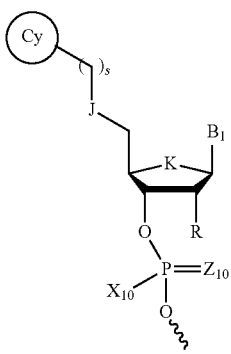

wherein J is an ether, sulfide, amino, ester, sulfonamide, amide, urea, carbamate or a phosphorus containing linkage;

K is independently O, S, NR', optionally substituted alkyl in each occurrence, where R' is hydrogen, acyl, aliphatic or substituted aliphatic;

$B^1$ and $B^2$ are natural or modified nucleobases;

$X_{10}$ is H, OH, OM, SM, SH, optionally substituted alkyl, optionally substituted alkoxy, optionally substituted alkylthio, optionally substituted alkylamino, optionally substituted dialkylamino, where M represents independently for each occurrence an alkali metal or a transition metal with an overall charge of +1;

$Z_{10}$ is O, S or NR';

$Y_{10}$ is O, S or NR';

R is each independently H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino; s is 0-10; and Cy is a substituted or unsubstituted heteroaryl, a substituted or unsubstituted heterocyclic, a substituted or unsubstituted aryl, a substituted or unsubstituted cycloalkyl. Provided that when Cy is a ribo, J is not a phosphorus containing linkage.

In one example,

is piperazinyl, pyrrolidinyl, dioxanyl, morpholinyl or tetrahydrofuranyl.

A nucleosidic end cap may be attached to the 5' end of the strand through the 3' or 2' position of the end cap via an ether linkage, such as in the following:

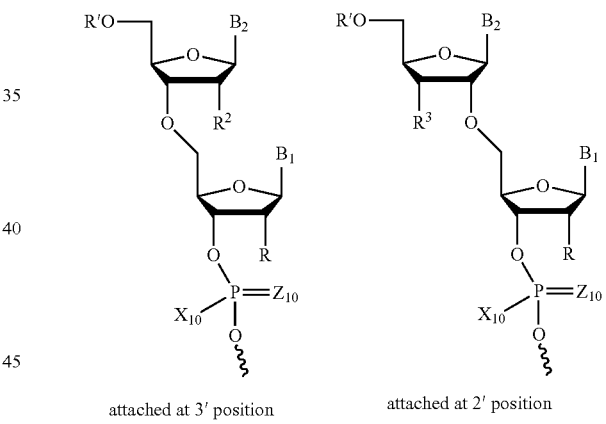

attached at 3' position    attached at 2' position wherein $B^1$ and $B^2$ are natural or modified nucleobases;

$X_{10}$ is H, OH, OM, SH, SM, optionally substituted alkyl, optionally substituted alkoxy, optionally substituted alkylthio, optionally substituted alkylamino, optionally substituted dialkylamino, where M represents independently for each occurrence an alkali metal or a transition metal with an overall charge of +1;

$Z_{10}$ is O, S or NR', where R' is hydrogen, acyl, aliphatic or substituted aliphatic;

R, $R^2$ or $R^3$ each is independently H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino.

A non-nucleosidic end cap may be attached to the strand through various position of the pyrrolidinyl end cap via a phosphodiester linkage, such as in the following examples:

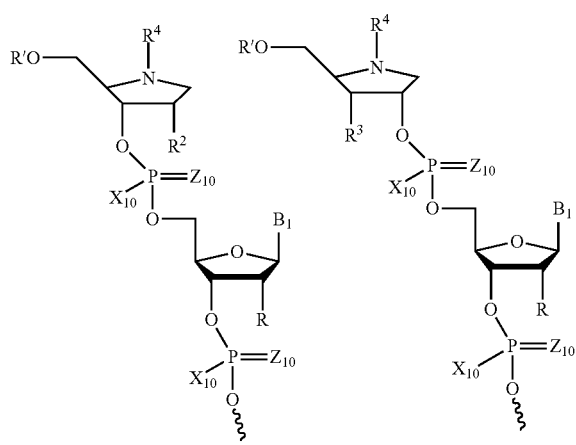

wherein is $B^1$ natural or modified nucleobases;

each $X_{10}$ is independently H, OH, OM, SH, SM, optionally substituted alkyl, optionally substituted alkoxy, optionally substituted alkylthio, optionally substituted alkylamino, optionally substituted dialkylamino, where M represents independently for each occurrence an alkali metal or a transition metal with an overall charge of +1;

each $Z_{10}$ is independently O, S or NR', where R' is hydrogen, acyl, aliphatic or substituted aliphatic;

R, $R^2$ or $R^3$ each is independently H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino.

A non-nucleosidic end cap may be attached to the 5' end of the strand through various position of the pyrrolidinyl end cap via an ether linkage, such as in the following examples:

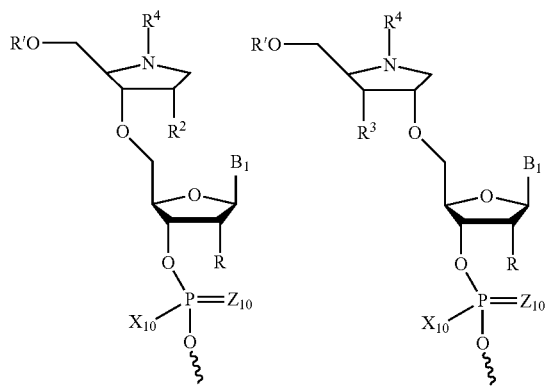

wherein is $B^1$ natural or modified nucleobases;

each $X_{10}$ is independently H, OH, OM, SH, SM, optionally substituted alkyl, optionally substituted alkoxy, optionally substituted alkylthio, optionally substituted alkylamino, optionally substituted dialkylamino, where M represents independently for each occurrence an alkali metal or a transition metal with an overall charge of +1;

each $Z_{10}$ is independently O, S or NR', where R' is hydrogen, acyl, aliphatic or substituted aliphatic;

R, $R^2$ or $R^3$ each is independently H, OH, SH, halogen, optionally substituted alkyl, optionally substituted alkenyl, optionally substituted alkynyl, optionally substituted alkoxy, optionally substituted alkylthio, optionally substituted alkylamino, optionally substituted dialkylamino.

Figure 1B:
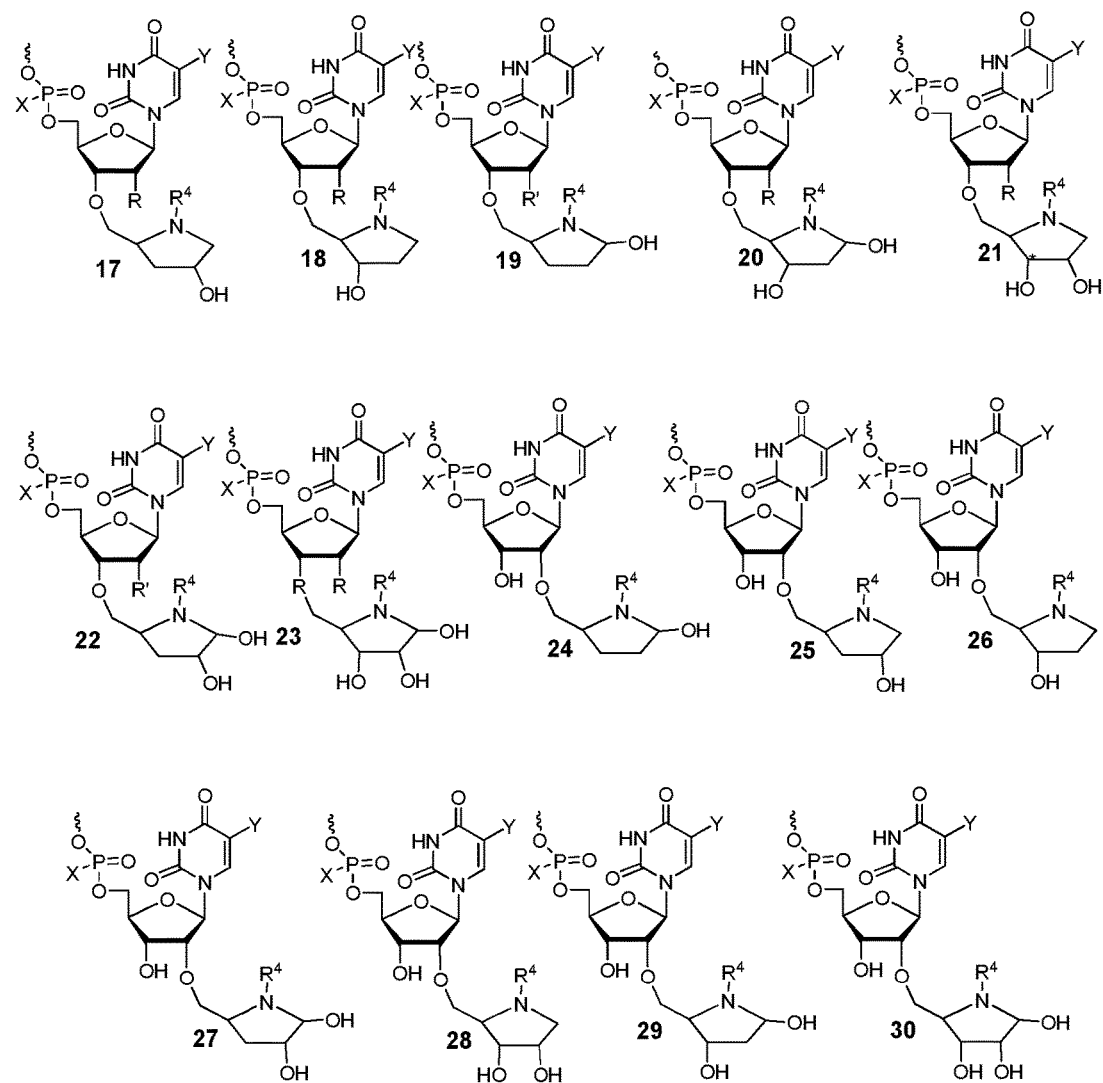
Figure 1C:
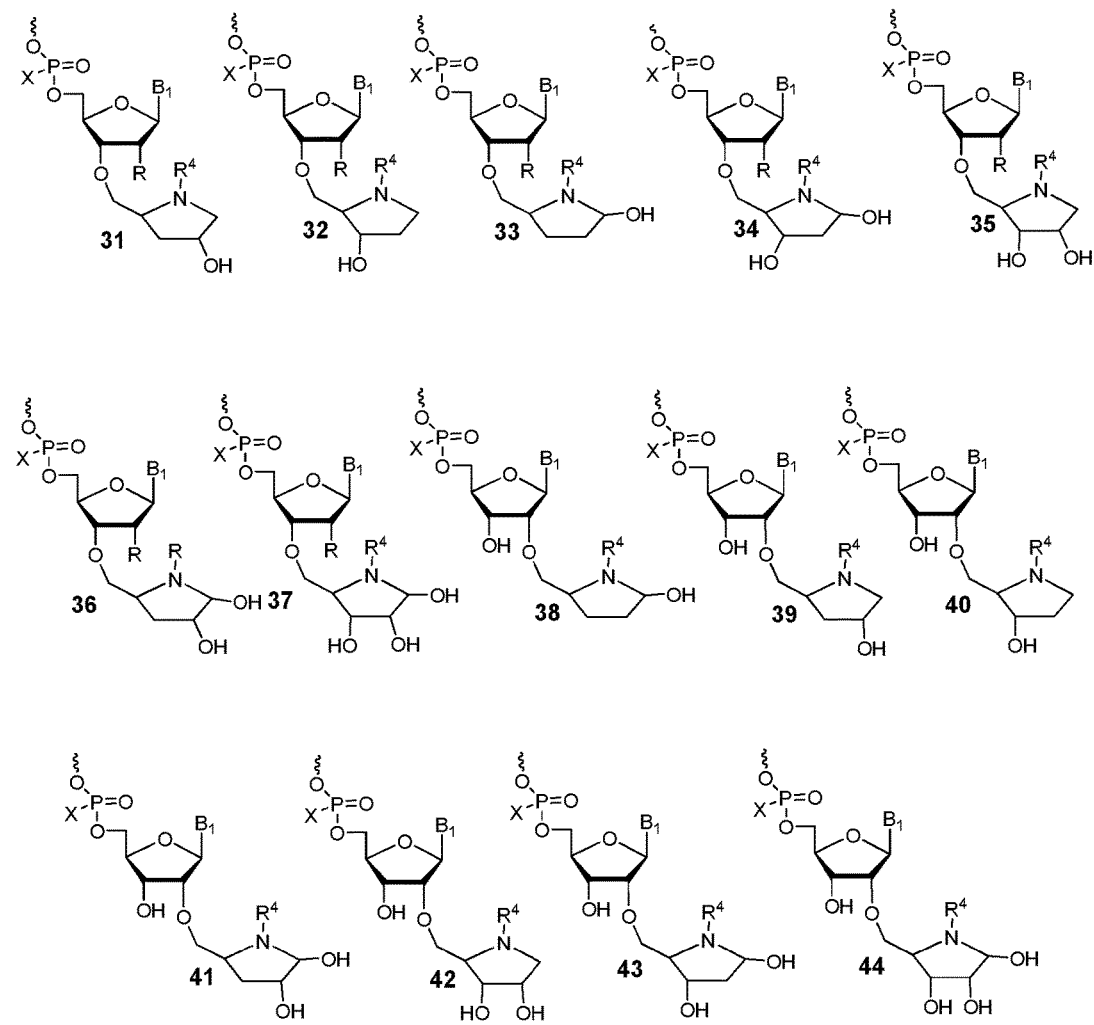
Figure 1D:
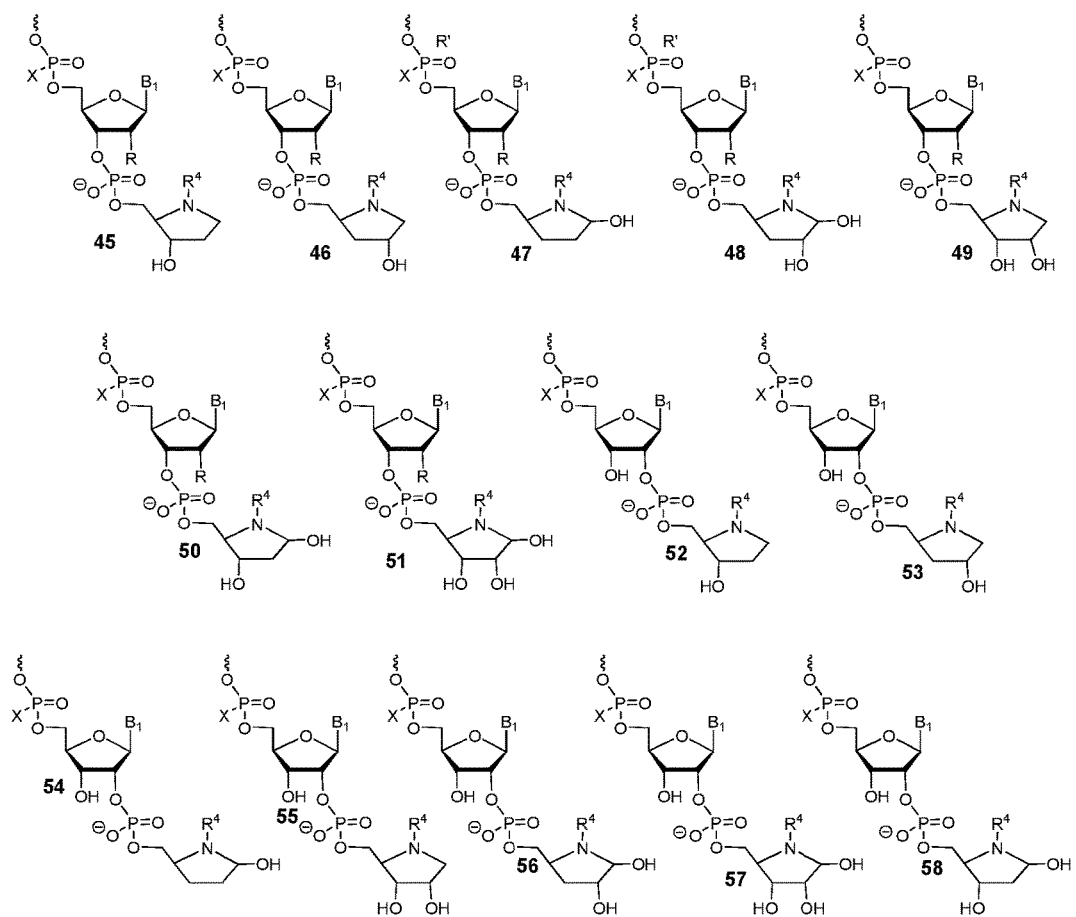
Figure 1E:
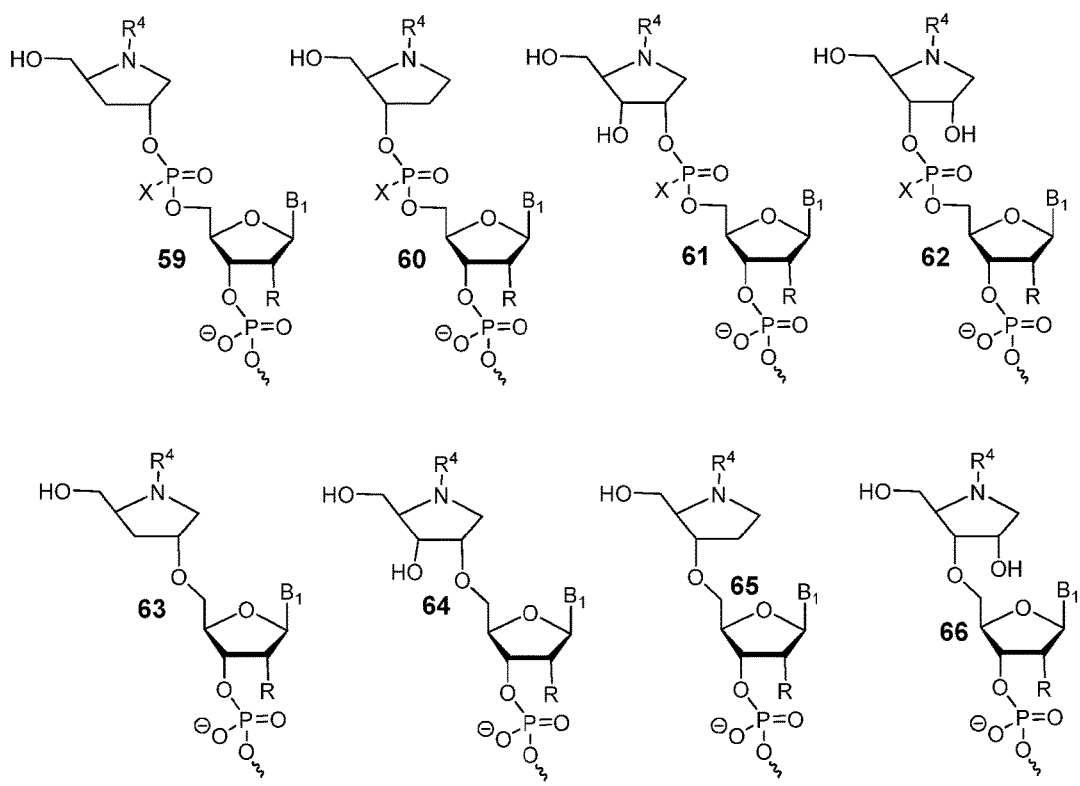
Figure 1F:
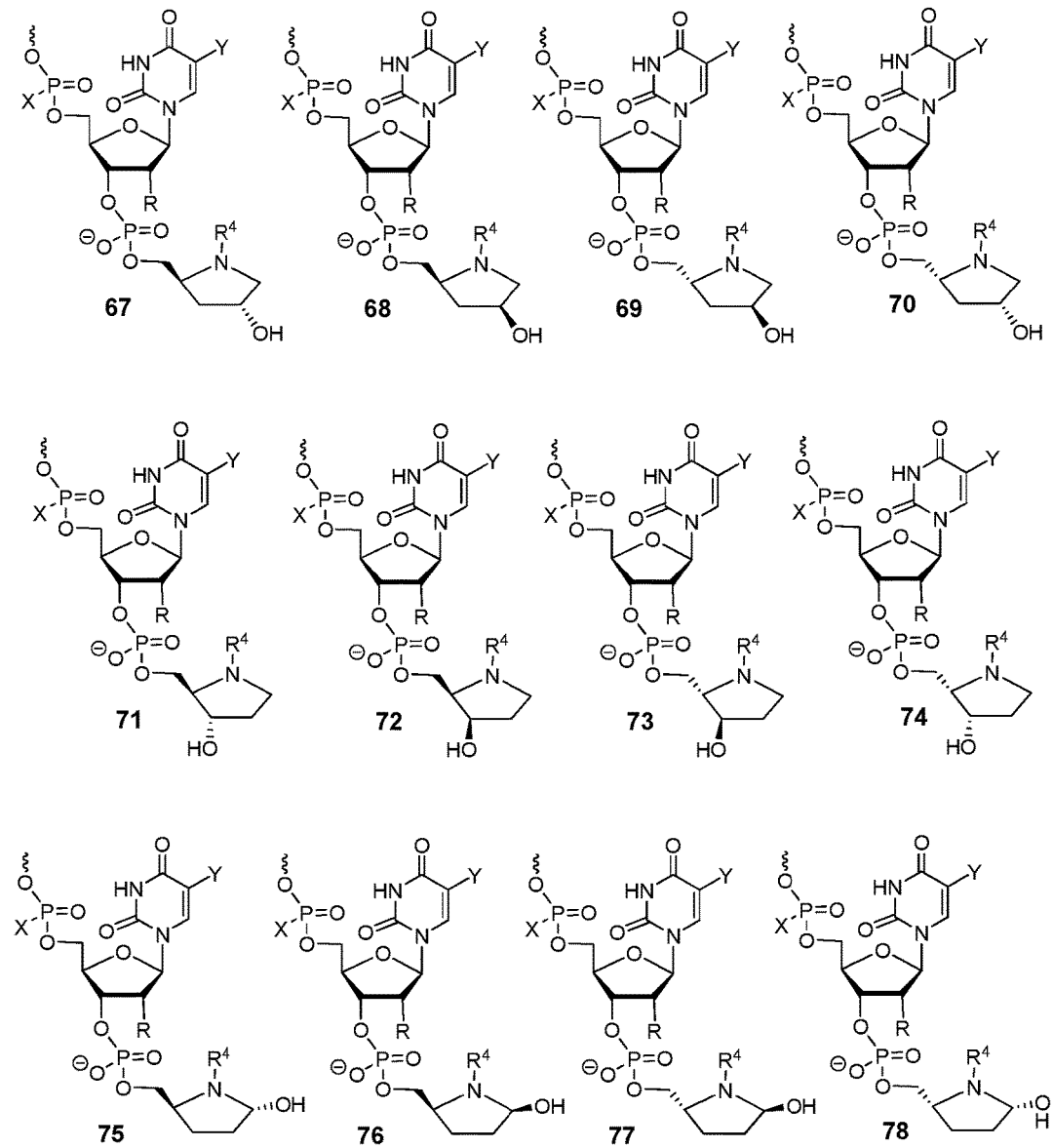

Exemplary modified nucleic acids are provided in FIGS. 1A-1F. The figures depict at least one base from the nucleic acid bound to a end caps of the invention as provided herein.

The end cap modifications described herein can be used on any of the nucleic acid agents described herein, including single stranded and double stranded agents. Where a nucleic acid agent is a double stranded agent, one or both of the strands of the agent can be modified with an end cap described herein. For example, a double stranded agent can be modified on the 3' end of both strands with an end cap described herein. The nucleic acid agents can be further modified, for example, with one or more modifications described herein.

In one embodiment, the end caps of the invention provides oligonucleotides with an in-vivo half-life of at least about 1 hours, at least about 2 hours, at least about 3 hours, at least about 4 hours, at least about 5 hours, at least about 6 hours, at least about 7 hours, at least about 8 hours, at least about 9 hours, and at least about 10 hours.

In one embodiment, B is uracil, 5-methyluracil, 5-methylcytosine, cytosine, 5-thiazolo-uracil, 5-thiazolo-cytosine, adenine, guanine or 2,6-diaminopurine, 6-oxopurine, pseudouridine, N1 substituted pseudouridine, xanthine, 2-aminopurine, or 7-deazapurine.

In one embodiment, the oligonucleotides of the invention comprise internucleoside linkages selected from phosphorus and non-phosphorus containing internucleoside. In one example, the phosphorus containing internucleoside includes, but not limited to, phosphodiester, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity where one or more internucleotide linkages is a 3' to 3', 5' to 5' or 2' to 2' linkage. Oligonucleotides having inverted polarity can comprise a single 3' to 3' linkage at the 3'-most inter-nucleotide linkage i.e. a single inverted nucleoside residue which may be abasic (the nucleobase is missing or has a hydroxyl group in place thereof). Various salts, mixed salts and free acid forms are also included. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

In one embodiment, oligonucleotides of the invention comprise one or more internucleoside linkages that don't contain a phosphorus atom. Such oligonucleotides include, but are not limited to, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above non-phosphorus containing internucleoside linking group include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In one embodiment, oligonucleotides of the invention comprise one or more neutral internucleoside linkages that are non-ionic. Suitable neutral internucleoside linkages include, but are not limited to, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'); nonionic linkages containing siloxane (dialkylsiloxane), carboxylate ester, carboxamide, sulfide, sulfonate ester and/or amides (See for example: Carbohydrate Modifications in Antisense Research; Y. S. Sanghvi and P. D. Cook Eds. ACS Symposium Series 580; Chapters 3 and 4, (pp. 40-65)); and nonionic linkages containing mixed N, O, S and $CH_2$ component parts.

In one embodiment, the non-phosphodiester backbone linkage is selected from the group consisting of phosphorothioate, phosphorodithioate, alkyl-phosphonate and phosphoramidate backbone linkages.

In one aspect, the present invention provides an oligonucleotide comprising at least one modified non nucleosidic end caps of the inventions optionally in combination with natural base and derivatives thereof, or modified nucleobase. The modified base includes high affinity modification such as G-clamp and its analogs; phenoxazines and their analogs; bi- and tricyclic non-natural nucleoside bases. The invention further provides said modified oligonucleotides with 3', 5' or both 3' and 5' terminal phosphate or phosphate mimics. The phosphate or phosphate mimics includes α- and/or β-configuration with respect to the sugar ring or combinations thereof. The phosphate or phosphate mimics include but not limited to: natural phosphate, phosphorothioate, phosphorodithioate, borano phosphate, borano thiophosphate, phosphonate, halogen substituted phosphonates, phosphoramidates, phosphodiester, phosphotriester, thiophosphodiester, thiophosphotriester, diphosphates and triphosphates. The invention also provides sugar-modified purine dimers at 3' and 5'-terminals (i.e. 5'/3'-GG, AA, AG, GA, GI, IA etc.), where the purine bases are natural or chemically modified preferably at the 2, 6, 7, and 8 positions; $N^2$ and $N^6$ exocyclic amine positions of the base or combinations thereof. The nucleoside at position 1 (5'-end) may contain a 2' and/or 4'-sugar modified natural and modified nucleobase, purine or pyrimidine nucleobase mimics or combinations thereof. The modified oligonucleotides may be single stranded siRNA, double stranded siRNA, micro RNA, antimicroRNA, supermir, aptamer, immunostimulatory, U1 adaptor, RNA activator or an antisense oligonucleotide containing a motif selected from the modifications described herein and combinations of modifications thereof. The modified oligonucleotide is one of the strands or constitute for both strands of a double-stranded siRNA. In one occurrence the modified oligonucleotide is the guide or antisense strand, and in another occurrence the modified oligonucleotide is sense or passenger strand of the double-stranded siRNA; or both strands of ds siRNA bear modified oligonucleotides.

In one embodiment, the oligonucleotide comprises at least one ligand conjugate.

In one embodiment, the oligonucleotide comprises two or more ligand conjugates.

In one embodiment, the oligonucleotide is a double-stranded oligonucleotide.

In one embodiment, only one strand comprises the modified nucleoside.

In one embodiment, both strands comprise the modified nucleoside.

In one embodiment, the modified nucleoside is the same in the two strands.

In one embodiment, the modified nucleoside is different in the two strands.

In one embodiment, the oligonucleotide is a single-stranded oligonucleotide.

In one embodiment, the oligonucleotide has a hairpin structure.

In one embodiment, the oligonucleotide is an RNAi agent, an antisense, an antagomir, a microRNA, a pre-microRNA, an antimir, a ribozyme, RNA activator, U1 adaptor, immunostimulatory or an aptamer oligonucleotide.

In one embodiment, the RNAi agent is single stranded.

In one embodiment, the RNAi agent is double stranded and only the sense strand comprises the modified nucleoside.

In one embodiment, the RNAi agent is double stranded and only the antisense strand comprises the modified nucleoside.

In one embodiment, the RNAi agent is double-stranded and both the sense and the antisense strands comprise at least one modified nucleoside.

In one embodiment, the modified nucleoside is the same in both the sense and the antisense strands.

In one embodiment, the sense and the antisense strands comprise different modified nucleosides.

The nucleoside and oligonucleotides described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion. In general, the term "oligomeric compound" refers to a contiguous sequence of linked monomelic subunits. In general each linked monomeric subunits is directly or indirectly attached to a heterocyclic base moiety but abasic sites are also possible. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having a plurality of non-naturally occurring nucleoside mimetics and or nucleosides having sugar surrogate groups.

Oligonucleotides

In the context of this invention, the term "oligonucleotide" refers to a polymer or oligomer of nucleotide or nucleoside monomers consisting of naturally occurring bases, sugars and intersugar (backbone) linkages. The term "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

The nucleic acids used herein can be single-stranded or double-stranded. A single stranded oligonucleotide may have double stranded regions and a double stranded oligonucleotide may have regions of single-stranded regions. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include, e.g., antisense oligonucleotides, ribozymes, microRNAs, aptamers, antagomirs, triplex-forming oligonucleotides and single-stranded RNAi agents.

Oligonucleotides of the present invention may be of various lengths. In particular embodiments, oligonucleotides may range from about 10 to 100 nucleotides in length. In various related embodiments, oligonucleotides, single-stranded, double-stranded, and triple-stranded, may range in length from about 10 to about 50 nucleotides, from about 20 to about 50 nucleotides, from about 15 to about 30 nucleotides, from about 20 to about 30 nucleotides in length.

The oligonucleotides of the invention may comprise any oligonucleotide modification described herein and below. In certain instances, it may be desirable to modify one or both strands of a dsRNA. In some cases, the two strands will include different modifications. Multiple different modifications can be included on each of the strands. The modifications on a given strand may differ from each other, and may also differ from the various modifications on other strands. For example, one strand may have a modification, e.g., a modification described herein, and a different strand may have a different modification, e.g., a different modification described herein. In other cases, one strand may have two or more different modifications, and the another strand may include a modification that differs from the at least two modifications on the other strand.

In one embodiment, oligonucleotides of the invention comprises 5' phosphorothioate or 5'-phosphorodithioate, nucleotides 1 and 2 having cationic modifications via C-5 position of pyrimidines, 2-Position of Purines, N2-G, G-clamp, 8-position of purines, 6-position of purines, internal nucleotides having a 2'-F sugar with base modifications (Pseudouridine, G-clamp, phenoxazine, pyridopyrimidines, gem2'-Me-up/2'-F-down), 3'-end with two purines with novel 2'-substituted MOE analogs, 5'-end nucleotides with novel 2'-substituted MOE analogs, 5'-end having a 3'-F and a 2'-5'-linkage, 4'-substituted nucleoside at the nucleotide 1 at 5'-end and the substituent is cationic, alkyl, alkoxyalkyl, thioether and the like, 4'-substitution at the 3'-end of the strand, and combinations thereof.

Double-Stranded Oligonucleotides

In one embodiment, the invention provides double-stranded ribonucleic acid (dsRNA) molecules for inhibiting the expression of the target gene (alone or in combination with a second dsRNA for inhibiting the expression of a second target gene) in a cell or mammal, where the dsRNA comprises an antisense strand comprising a region of complementarity which is complementary to at least a part of an mRNA formed in the expression of the target gene, and where the region of complementarity is less than 30 nucleotides in length, generally 19-24 nucleotides in length, and where the dsRNA, upon contact with a cell expressing the target gene, inhibits the expression of the target gene. The dsRNA comprises two RNA strands that are sufficiently complementary to hybridize to form a duplex structure. Generally, the duplex structure is between 15 and 30, more generally between 18 and 25, yet more generally between 19 and 24, and most generally between 19 and 21 base pairs in length. In one embodiment, longer dsRNAs of between 25 and 30 base pairs in length are preferred. In one embodiment, shorter dsRNAs of between 10 and 15 base pairs in length are preferred. In another embodiment, the dsRNA is at least 21 nucleotides long and includes a sense RNA strand and an antisense RNA strand, where the antisense RNA strand is 25 or fewer nucleotides in length, and the duplex region of the dsRNA is 18-25 nucleotides in length, e.g., 19-24 nucleotides in length.

In certain embodiments, the double-stranded region of a double-stranded oligonucleotide is equal to or at least, 10, 11, 12, 13, 14, 15, 16, 17, 18, 19, 20, 21, 22, 23, 23, 24, 25, 26, 27, 28, 29, or 30 nucleotide pairs in length.

In certain embodiments, the antisense strand of a double-stranded oligonucleotide is equal to or at least 14, 15, 16, 17, 18, 19, 20, 21, 22, 23, 23, 24, 25, 26, 27, 28, 29, or 30 nucleotides in length.

In certain embodiments, the sense strand of a double-stranded oligonucleotide is equal to or at least 10, 11, 12, 13, 14, 15, 16, 17, 18, 19, 20, 21, 22, 23, 23, 24, 25, 26, 27, 28, 29, or 30 nucleotides in length.

Similarly, the region of complementarity to the target sequence is between 15 and 30, more generally between 18 and 25, yet more generally between 19 and 24, and most generally between 19 and 21 nucleotides in length. The dsRNA of the invention may further comprise one or more single-stranded nucleotide overhang(s).

In a preferred embodiment, the target gene is a human target gene. In one embodiment, the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, p73 gene, p21(WAF1/CIP1) gene, p27(KIP1) gene, PPM1D gene, RAS gene, caveolin I gene, MIB I gene, MTAI gene, M68 gene, mutations in tumor suppressor genes, p53 tumor suppressor gene, and combinations thereof.

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above the dsRNAs of the invention can comprise at least one strand of a length of minimally 21 nt. It can be reasonably expected that shorter dsRNAs comprising a known sequence minus only a few nucleotides on one or both ends may be similarly effective as compared to the dsRNAs of the lengths described above. Hence, dsRNAs comprising a partial sequence of at least 15, 16, 17, 18, 19, 20, or more contiguous nucleotides, and differing in their ability to inhibit the expression of the target gene by not more than 5, 10, 15, 20, 25, or 30% inhibition from a dsRNA comprising the full sequence, are contemplated by the invention. Further dsRNAs that cleave within the target sequence can readily be made using the target gene sequence and the target sequence provided.

Double-stranded and single-stranded oligonucleotides that are effective in inducing RNA interference are also referred to as siRNA, RNAi agent and/or iRNA agent. These RNA interference inducing oligonucleotides associate with a cytoplasmic multi-protein complex known as RNAi-induced silencing complex (RISC). In certain embodiments, single-stranded and double stranded RNAi agents are sufficiently long that they can be cleaved by an endogenous molecule, e.g. by Dicer, to produce smaller oligonucleotides that can enter the RISC machinery and participate in RISC mediated cleavage of a target sequence, e.g. a target mRNA.

The present invention further includes RNAi agents that target within the sequence targeted by one of the agents of the present invention. As used herein a second RNAi agent is said to target within the sequence of a first RNAi agent if the second RNAi agent cleaves the message anywhere within the mRNA that is complementary to the antisense strand of the first RNAi agent. Such a second agent will generally consist of at least 15 contiguous nucleotides coupled to additional nucleotide sequences taken from the region contiguous to the selected sequence in the target gene.

The dsRNA of the invention may contain one or more mismatches to the target sequence. In a preferred embodiment, the dsRNA of the invention contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of the target gene, the dsRNA generally does not contain any mismatch within the central 13 nucleotides. The methods described within the invention can be used to determine whether a dsRNA containing a mismatch to a target sequence is effective in inhibiting the expression of the target gene. Consideration of the efficacy of dsRNAs with mismatches in inhibiting expression of the target gene is important, especially if the particular region of complementarity in the target gene is known to have polymorphic sequence variation within the population.

In certain embodiments, the sense-strand comprises a mismatch to the antisense strand. In certain embodiments, the mismatch is within 5 nucleotides from the end of the double stranded region, for example at positions 5, 4, 3, 2, or 1 from the end of the duplex region. Preferably, the mismatch is within 5 nucleotides from the end of the duplex corresponding to the 3'-end of the sense strand. In some embodiments, the mismatch is located in the target cleavage site region. In one embodiment, the sense strand comprises no more than 1, 2, 3, 4 or 5 mismatches to the antisense strand. In preferred embodiments, the sense strand comprises no more than 3 mismatches to the antisense strand.

In one embodiment, the sense strand comprises a nucleobase modification, e.g. an optionally substituted natural or non-natural nucleobase, a universal nucleobase, in the target cleavage site region.

In certain embodiments, the sense strand comprises an abasic nucleotide in the target cleavage site region.

The "target cleavage site" herein means the backbone linkage in the target gene, e.g. target mRNA, or the sense strand that is cleaved by the RISC mechanism by utilizing the iRNA agent. And the "target cleavage site region" comprises at least one or at least two nucleotides on both side of the cleavage site. For the sense strand, the target cleavage site is the backbone linkage in the sense strand that would get cleaved if the sense strand itself was the target to be cleaved by the RNAi mechanism. The target cleavage site can be determined using methods known in the art, for example the 5'-RACE assay as detailed in Soutschek et al., *Nature* (2004) 432, 173-178. As is well understood in the art, the cleavage site region for a conical double stranded RNAi agent comprising two 21-nucleotides long strands (wherein the strands form a double stranded region of 19 consecutive basepairs having 2-nucleotide single stranded overhangs at the 3'-ends), the cleavage site region corresponds to positions 9-12 from the 5'-end of the sense strand.

In one embodiment, at least one end of the dsRNA has a single-stranded nucleotide overhang of 1 to 4, generally 1 or 2 nucleotides. In certain embodiments, both ends of the double-stranded region have a single-stranded nucleotide overhang of 1 to 4, generally 1 or 2 nucleotides. As used herein, the term "overhang" refers to a double-stranded structure where at least one end of one strand is longer than the corresponding end of the other strand forming the double-stranded structure.

In some embodiments it is particularly preferred, e.g., to enhance stability, to include particular nucleobases in the single-stranded overhangs, or to include modified nucleotides or nucleotide surrogates, in single-strand overhangs. For example, it can be desirable to include purine nucleotides in overhangs. In some embodiments all or some of the bases in the single strand overhang will be modified, e.g., with a modification described herein. Modifications in the single-stranded overhangs can include any oligonucleotide modification described herein and below, e.g., the use of sugars with modifications at the 2' position, e.g., the use of deoxyribonucleotides, e.g., deoxythymidine, instead of ribonucleotides, and modifications in the phosphate group, e.g., phosphothioate modifications. Overhangs need not be homologous with the target sequence. In certain embodiments, the single strand overhangs are asymmetrically modified with a modification described herein, e.g. a first single-stand overhang comprises a modification that is not present in a second single-strand overhang.

In certain embodiments, the unpaired nucleotide adjacent to the terminal nucleotide base pair on the end of the double-stranded region is a purine.

In one embodiment, the single-stranded overhang has the sequence 5'-GCNN-3', where N is independently for each occurrence, A, G, C, U, dT, dU or absent. In certain embodiments, the single-stranded overhang has the sequence 5'-NN-3', wherein N is independently for each occurrence a modified or unmodified nucleotide described herein and below. dsRNAs having at least one nucleotide overhang have unexpectedly superior inhibitory properties than their blunt-ended counterparts. Without wishing to be bound by theory, presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Generally, the antisense strand of the dsRNA has a nucleotide overhang at the 3'-end, and the 5'-end is blunt.

In one embodiment, the antisense strand of the dsRNA has 1-10 nucleotides overhangs each at the 3' end and the 5' end over the sense strand. In one embodiment, the sense strand of the dsRNA has 1-10 nucleotides overhangs each at the 3' end and the 5' end over the antisense strand.

In certain embodiments, one strand has at least one stretch of 1-5 single-stranded nucleotides in the double-stranded region. In certain other embodiments, both strands have at least one stretch of 1-5 single-stranded nucleotides in the double stranded region. When both strands have a stretch of 1-5 single-stranded nucleotides in the double stranded region, such single-stranded nucleotides may be opposite to each other or they can be located such that the second strand has no single-stranded nucleotides opposite to the single-stranded oligonucleotides of the first strand and vice versa.

In certain embodiments, at least one strand of the double-stranded oligonucleotide has a ZXY structure, such as is described in PCT Application No. PCT/US2004/07070 filed on Mar. 8, 2004, contents of which are hereby incorporated in their entireties.

The dsRNAs of the invention may comprise any oligonucleotide modification described herein and below. In certain instances, it may be desirable to modify one or both strands of a dsRNA. In some cases, the two strands will include different modifications. Multiple different modifications can be included on each of the strands. The modifications on a given strand may differ from each other, and may also differ from the various modifications on other strands. For example, one strand may have a modification, e.g., a modification described herein, and a different strand may have a different modification, e.g., a different modification described herein. In other cases, one strand may have two or more different modifications, and the another strand may include a modification that differs from the at least two modifications on the other strand.

In one embodiment, the dsRNA is chemically modified to enhance stability. In one preferred embodiment, one or more of the nucleotides in the overhang is replaced with a nucleoside thiophosphate.

The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of an dsRNA compound. These dsRNAs typically contain at least one region where the dsRNA is modified so as to confer upon the dsRNA increased resistance to nuclease degradation, increased cellular uptake, and/or increased binding affinity for the target nucleic acid. An additional region of the dsRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression.

The present invention also includes dsRNAs where the two strands are linked together. The two strands can be linked to each other at both ends, or at one end only. When the two strands are linked to each other at both ends, 5'-end of one strand is linked to the 3'-end of the second strand and vice versa. The two strands can be linked together by a polynucleotide linker such as $(dT)_n$; where n is 4-10. When the two strands are linked to each other through a polynucleotide linker at one end only, the oligonucleotide forms a hairpin. The two strands can also be linked together by a non-nucleosidic linker, e.g. a linker described herein. It will be appreciated by one of skill in the art that any oligonucleotide chemical modifications or variations describe herein can be used in the polynucleotide linker.

Hairpin RNAi agents will have a duplex region equal to or at least 16, 17, 18, 19, 29, 21, 22, 23, 24, or 25 nucleotide pairs. The duplex region will may be equal to or less than 200, 100, or 50, in length. In one embodiment, ranges for the duplex region are 15-30, 17 to 23, 19 to 23, and 19 to 21 nucleotides pairs in length. The hairpin may have a single strand overhang or terminal unpaired region, in some embodiments at the 3', and in one embodiment on the antisense side of the hairpin. In one embodiment, the overhangs are 1-4 and preferably 2-3 nucleotides in length.

The RNAi agents of the invention can target more than one RNA region. For example, an RNAi agent can include a first and second sequence that are sufficiently complementary to each other to hybridize. The first sequence can be complementary to a first target RNA region and the second sequence can be complementary to a second target RNA region. The first and second sequences of the RNAi agent can be on different RNA strands, and the mismatch between the first and second sequences can be less than 50%, 40%, 30%, 20%, 10%, 5%, or 1%. The first and second sequences of the RNAi agent can be on the same RNA strand, and in a related embodiment more than 50%, 60%, 70%, 80%, 90%, 95%, or 1% of the RNAi agent can be in bimolecular form. The first and second sequences of the RNAi agent can be fully complementary to each other.

RNAi agents of the invention can be used to target two or more RNA regions where the RNA regions differ from each other at 1, 2, 3, 4 or 5 positions. As used in this context, the phrase "differ from each other" refers to the RNA regions having different nucleotides at that position. In these cases the RNAi agent strand that is complementary to the RNA region to be targeted comprises universal nucleobases at positions complementary to where the RNA regions are different from each other. For example, the antisense strand of the double-stranded RNAi agent comprises universal nucleobases at positions complementary to where the RNA regions to be targeted do not match each other.

As used herein, a universal nucleobase is any modified, unmodified, naturally occurring or non-naturally occurring nucleobase that can base pair with all of the four naturally occurring nucleobases without substantially affecting the melting behavior, recognition by intracellular enzymes or activity of the oligonucleotide duplex. Some exemplary universal nucleobases include, but are not limited to, 2,4-difluorotoluene, nitropyrrolyl, nitroindolyl, 8-aza-7-deazaadenine, 4-fluoro-6-methylbenzimidazle, 4-methyl-benzimidazle, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylinolyl, 4,6-dimethylindolyl, phenyl, napthalenyl, anthracenyl, phenanthracenyl, pyrenyl, stilbenyl, tetracenyl, pentacenyl, and structural derivatives thereof.

The first target RNA region can be encoded by a first gene and the second target RNA region can encoded by a second gene, or the first and second target RNA regions can be different regions of an RNA from a single gene. The first and second sequences can differ by at least 1 nucleotide.

The first and second target RNA regions can be on transcripts encoded by first and second sequence variants, e.g., first and second alleles, of a gene. The sequence variants can be mutations, or polymorphisms, for example. The first target RNA region can include a nucleotide substitution, insertion, or deletion relative to the second target RNA region, or the second target RNA region can a mutant or variant of the first target region.

The first and second target RNA regions can comprise viral or human RNA regions. The first and second target RNA regions can also be on variant transcripts of an oncogene or include different mutations of a tumor suppressor gene transcript. In addition, the first and second target RNA regions can correspond to hot-spots for genetic variation.

The double stranded oligonucleotides can be optimized for RNA interference by increasing the propensity of the duplex to disassociate or melt (decreasing the free energy of duplex association), in the region of the 5' end of the antisense strand This can be accomplished, e.g., by the inclusion of modifications or modified nucleosides which increase the propensity of the duplex to disassociate or melt in the region of the 5' end of the antisense strand. It can also be accomplished by inclusion of modifications or modified nucleosides or attachment of a ligand that increases the propensity of the duplex to disassociate of melt in the region of the 5'end of the antisense strand. While not wishing to be bound by theory, the effect may be due to promoting the effect of an enzyme such as helicase, for example, promoting the effect of the enzyme in the proximity of the 5' end of the antisense strand.

Modifications which increase the tendency of the 5' end of the antisense strand in the duplex to dissociate can be used alone or in combination with other modifications described herein, e.g., with modifications which decrease the tendency of the 3' end of the antisense in the duplex to dissociate. Likewise, modifications which decrease the tendency of the 3' end of the antisense in the duplex to dissociate can be used alone or in combination with other modifications described herein, e.g., with modifications which increase the tendency of the 5' end of the antisense in the duplex to dissociate.

Nucleic acid base pairs can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; I:C is preferred over G:C (I=inosine); mismatches, e.g., non-canonical or other than canonical pairings are preferred over canonical (A:T, A:U, G:C) pairings; pairings which include a universal base are preferred over canonical pairings.

It is preferred that pairings which decrease the propensity to form a duplex are used at 1 or more of the positions in the duplex at the 5' end of the antisense strand. The terminal pair (the most 5' pair in terms of the antisense strand), and the subsequent 4 base pairing positions (going in the 3' direction in terms of the antisense strand) in the duplex are preferred for placement of modifications to decrease the propensity to form a duplex. More preferred are placements in the terminal most pair and the subsequent 3, 2, or 1 base pairings. It is preferred that at least 1, and more preferably 2, 3, 4, or 5 of the base pairs from the 5'-end of antisense strand in the duplex be chosen independently from the group of: A:U, G:U, I:C, mismatched pairs, e.g., non-canonical or other than canonical pairings or pairings which include a universal base. In a preferred embodiment at least one, at least 2, or at least 3 base-pairs include a universal base.

Modifications or changes which promote dissociation are preferably made in the sense strand, though in some embodiments, such modifications/changes will be made in the antisense strand.

Nucleic acid base pairs can also be ranked on the basis of their propensity to promote stability and inhibit dissociation or melting (e.g., on the free energy of association or dissociation of a particular pairing, the simplest approach is to examine the pairs on an individual pair basis, though next neighbor or similar analysis can also be used). In terms of promoting duplex stability: G:C is preferred over A:U, Watson-Crick matches (A:T, A:U, G:C) are preferred over non-canonical or other than canonical pairings, analogs that increase stability are preferred over Watson-Crick matches (A:T, A:U, G:C), e.g. 2-amino-A:U is preferred over A:U, 2-thio U or 5 Me-thio-U:A, are preferred over U:A, G-clamp (an analog of C having 4 hydrogen bonds):G is preferred over C:G, guanadinium-G-clamp:G is preferred over C:G, psuedo uridine:A, is preferred over U:A, sugar modifications, e.g., 2' modifications, e.g., 2'-O-methyl (2'-OMe), 2'-F, locked nucleic acids, e.g., ENA and LNA, which enhance binding are preferred over non-modified moieties and can be present on one or both strands to enhance stability of the duplex.

It is preferred that pairings which increase the propensity to form a duplex are used at 1 or more of the positions in the duplex at the 3' end of the antisense strand. The terminal pair (the most 3' pair in terms of the antisense strand), and the subsequent 4 base pairing positions (going in the 5' direction in terms of the antisense strand) in the duplex are preferred for placement of modifications to decrease the propensity to form a duplex. More preferred are placements in the terminal most pair and the subsequent 3, 2, or 1 base pairings. It is preferred that at least 1, and more preferably 2, 3, 4, or 5 of the pairs of the recited regions be chosen independently from the group of: G:C, a pair having an analog that increases stability over Watson-Crick matches (A:T, A:U, G:C), 2-amino-A:U, 2-thio U or 5 Me-thio-U:A, G-clamp (an analog of C having 4 hydrogen bonds):G, guanadinium-G-clamp:G, psuedo uridine:A, a pair in which one or both subunits has a sugar modification, e.g., a 2' modification, e.g., 2'-OMe, 2'-F, ENA or LNA, which enhance binding. In some embodiments, at least one, at least, at least 2, or at least 3, of the base pairs promote duplex stability.

In a preferred embodiment, at least one, at least 2, or at least 3, of the base pairs are a pair in which one or both subunits has a sugar modification, e.g., a 2' modification, e.g., 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA) and 2'-O—CH$_2$CH$_2$-(4'-C) (ENA), which enhances binding.

G-clamps and guanidinium G-clamps are discussed in the following references: Holmes and Gait, "The Synthesis of 2'-O-Methyl G-Clamp Containing Oligonucleotides and Their Inhibition of the HIV-1 Tat-TAR Interaction," Nucleosides, Nucleotides & Nucleic Acids, 22:1259-1262, 2003; Holmes et al., "Steric inhibition of human immunodeficiency virus type-1 Tat-dependent trans-activation in vitro and in cells by oligonucleotides containing 2'-O-methyl G-clamp ribonucleoside analogues," Nucleic Acids Research, 31:2759-2768, 2003; Wilds, et al., "Structural basis for recognition of guanosine by a synthetic tricyclic cytosine analogue: Guanidinium G-clamp," Helvetica Chimica Acta, 86:966-978, 2003; Rajeev, et al., "High-Affinity Peptide Nucleic Acid Oligomers Containing Tricyclic Cytosine Analogues," Organic Letters, 4:4395-4398, 2002; Ausin, et al., "Synthesis of Amino- and Guanidino-G-Clamp PNA Monomers," Organic Letters, 4:4073-4075, 2002; Maier et al., "Nuclease resistance of oligonucleotides containing the tricyclic cytosine analogues phenoxazine and 9-(2-aminoethoxy)-phenoxazine ("G-clamp") and origins of their nuclease resistance properties," Biochemistry, 41:1323-7, 2002; Flanagan, et al., "A cytosine analog that confers enhanced potency to antisense oligonucleotides," Proceedings Of The National Academy Of Sciences Of The United States Of America, 96:3513-8, 1999.

As is discussed above, an oligonucleotide can be modified to both decrease the stability of the antisense 5'end of the duplex and increase the stability of the antisense 3' end of the duplex. This can be effected by combining one or more of the stability decreasing modifications in the antisense 5' end of the duplex with one or more of the stability increasing modifications in the antisense 3' end of the duplex.

In certain embodiments, the terminal base pair of the double stranded region is a G-C base pair or four consecutive base pairs from the terminal end comprise at least two G-C base pairs. In further embodiments, each terminal end of the double stranded region comprises a G-C base pair at the terminal position or four consecutive base pairs from the terminal end comprise at least two G-C base pairs.

Single-Stranded Oligonucleotides

The single-stranded oligonucleotides of the present invention also comprise nucleotide sequence that is substantially complementary to a "sense" nucleic acid encoding a gene expression product, e.g., complementary to the coding strand of a double-stranded cDNA molecule or complementary to an RNA sequence, e.g., a pre-mRNA, mRNA, miRNA, or pre-miRNA. The region of complementarity is less than 30 nucleotides in length, and at least 15 nucleotides in length. Generally, the single stranded oligonucleotides are 10 to 25 nucleotides in length (e.g., 11, 12, 13, 14, 15, 16, 18, 19, 20, 21, 22, 23, or 24 nucleotides in length). In one embodiment the strand is 25-30 nucleotides. Single strands having less than 100% complementarity to the target mRNA, RNA or DNA are also embraced by the present invention. These single-stranded oligonucleotides are also referred to as antisense, antagomir and antimir oligonucleotides. In certain embodiments, the single-stranded oligonucleotide has a ZXY structure, such as is described in PCT Application No. PCT/US2004/07070, filed on Mar. 8, 2005. The single-stranded oligonucleotide can hybridize to a complementary RNA, and prevent access of the translation machinery to the target RNA transcript, thereby preventing protein synthesis. The single-stranded oligonucleotide can also hybridize to a complementary RNA and the RNA target can be subsequently cleaved by an enzyme such as RNase H. Degradation of the target RNA prevents translation.

Single-stranded oligonucleotides, including those described and/or identified as single stranded siRNAs, microRNAs or mirs which may be used as targets or may serve as a template for the design of oligonucleotides of the invention are taught in, for example, Esau, et al. US Publication #20050261218 (U.S. Ser. No. 10/909,125) entitled "Oligonucleotides and compositions for use in modulation small non-coding RNAs" the entire contents of which is incorporated herein by reference. It will be appreciated by one of skill in the art that any oligonucleotide chemical modifications or variations describe herein also apply to single stranded oligonucleotides.

MicroRNAs (miRNAs or mirs) are a highly conserved class of small RNA molecules that are transcribed from DNA in the genomes of plants and animals, but are not translated into protein. Pre-microRNAs are processed into miRNAs. Processed microRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

The number of miRNA sequences identified to date is large and growing, illustrative examples of which can be found, for example, in: "miRBase: microRNA sequences, targets and gene nomenclature" Griffiths-Jones S, Grocock R J, van Dongen S, Bateman A, Enright A J. NAR, 2006, 34, Database Issue, D140-D144; "The microRNA Registry" Griffiths-Jones S. NAR, 2004, 32, Database Issue, D109-D111; and also on the worldwide web at http://microrna.dot.sanger.dot.ac.dot.uk/sequences/.

Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate backbone and, for example, a cholesterol-moiety at 3'-end. Antagomirs may be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein in its entirety. Antagomir RNAs may be synthesized using standard solid phase oligonucleotide synthesis protocols. See U.S. patent application Ser. Nos. 11/502,158 and 11/657,341 (the disclosure of each of which are incorporated herein by reference).

An antagomir can include ligand-conjugated monomer subunits and monomers for oligonucleotide synthesis. Exemplary monomers are described in U.S. application Ser. No. 10/916,185, filed on Aug. 10, 2004. An antagomir can have a ZXY structure, such as is described in PCT Application No. PCT/US2004/07070 filed on Mar. 8, 2004. An antagomir can be complexed with an amphipathic moiety. Exemplary amphipathic moieties for use with oligonucleotide agents are described in PCT Application No. PCT/US2004/07070, filed on Mar. 8, 2004.

Single stranded siRNAs (ss siRNAs) are known and are described in US publication US 2006/0166910 and hereby incorporated by reference herein by its entirety. A "single stranded siRNA" as used herein, is an RNAi agent which is made up of a single molecule. A single stranded RNAi agent may include a duplexed region, formed by intra-strand pairing, e.g., it may be, or include, a hairpin or pan-handle structure. Single strand RNAi agents may be antisense with regard to the target molecule.

A single strand RNAi agent may be sufficiently long that it can enter the RISC and participate in RISC mediated cleavage of a target mRNA. A single strand RNAi agent is at least 14, and in other embodiments at least 15, at least 20, at least 25, at least 29, at least 35, at least 40, or at least 50 nucleotides in length. In certain embodiments, it is less than 200, 100, or 60 nucleotides in length. In certain embodiments single strand RNAi agents are 5' phosphorylated or include a phosphoryl analog at the 5' prime terminus. In one embodiment, the single-stranded oligonucleotide inhibits the expression of a target gene via RISC mediated cleavage of the target sequence.

Preferably, the single-stranded RNA molecule has a length from 15-29 nucleotides. The RNA-strand may have a 3'hydroxyl group. In some cases, however, it may be preferable to modify the 3' end to make it resistant against 3' to 5' exonucleases. Tolerated 3'-modifications are for example terminal 2'-deoxy nucleotides, 3' phosphate, 2',3'-cyclic phosphate, C3 (or C6, C7, C12) aminolinker, thiol linkers, carboxyl linkers, non-nucleotidic spacers (C3, C6, C9, C12, abasic, triethylene glycol, hexaethylene glycol), biotin, fluoresceine, etc. Single stranded siRNAs of the invention include at least one of the following motifs: 5' phosphorothioate or 5'-phosphorodithioate, nucleotides 1 and 2 having cationic modifications via C-5 position of pyrimidines, 2-Position of Purines, N2-G, G-clamp, 8-position of purines, 6-position of purines, internal nucleotides having a 2'-F sugar with base modifications (Pseudouridine, G-clamp, phenoxazine, pyridopyrimidines, gem2'-Me-up/2'-F-down), 3'-end with two purines with novel 2'-substituted MOE analogs, 5'-end nucleotides with novel 2'-substituted MOE analogs, 5'-end having a 3'-F and a 2'-5'-linkage, 4'-substituted nucleoside at the nucleotide 1 at 5'-end and the substituent is cationic, alkyl, alkoxyalkyl, thioether and the like, 4'-substitution at the 3'-end of the strand, and combinations thereof.

Ribozymes are oligonucleotides having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). At least six basic varieties of naturally-occurring enzymatic RNAs are known presently. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Methods of producing a ribozyme targeted to any target sequence are known in the art. Ribozymes may be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

Aptamers are nucleic acid or peptide molecules that bind to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9(1999), and Hermann and Patel, Science 287:820-5 (2000). Aptamers may be RNA or DNA based. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer may be prepared by any known method, including synthetic, recombinant, and purification methods, and may be used alone or in combination with other aptamers specific for the same target. Further, as described more fully herein, the term "aptamer" specifically includes "secondary aptamers" containing a consensus sequence derived from comparing two or more known aptamers to a given target.

Immunostimulatory Oligonucleotides

Nucleic acids of the present invention may be immunostimulatory, including immunostimulatory oligonucleotides (single- or double-stranded) capable of inducing an immune response when administered to a subject, which may be a mammal or other patient. The immune response may be an innate or an adaptive immune response. The immune system is divided into a more innate immune system, and acquired adaptive immune system of vertebrates, the latter of which is further divided into humoral cellular components. In particular embodiments, the immune response may be mucosal.

Immunostimulatory nucleic acids are considered to be non-sequence specific when it is not required that they specifically bind to and reduce the expression of a target polynucleotide in order to provoke an immune response. Thus, certain immunostimulatory nucleic acids may comprise a sequence corresponding to a region of a naturally occurring gene or mRNA, but they may still be considered non-sequence specific immunostimulatory nucleic acids.

In one embodiment, the immunostimulatory nucleic acid or oligonucleotide comprises at least one CpG dinucleotide. The oligonucleotide or CpG dinucleotide may be unmethylated or methylated. In another embodiment, the immunostimulatory nucleic acid comprises at least one CpG dinucleotide having a methylated cytosine. In one embodiment, the nucleic acid comprises a single CpG dinucleotide, wherein the cytosine in said CpG dinucleotide is methylated. Methods of immune stimulation using single stranded oligonucleotides and immune stimulatory oligonucleotides.

The immunostimulatory nucleic acid or oligonucleotide comprises capable of inducing an anti-viral or an antibacterial response, in particular, the induction of type I IFN, IL-18 and/or IL-1β by modulating RIG-I.

Immunostimulatory Oligonucleotides

Nucleic acids of the present invention may be immunostimulatory, including immunostimulatory oligonucleotides (single- or double-stranded) capable of inducing an immune response when administered to a subject, which may be a mammal or other patient. The immune response may be an innate or an adaptive immune response. The immune system is divided into a more innate immune system, and acquired adaptive immune system of vertebrates, the latter of which is further divided into humoral cellular components. In particular embodiments, the immune response may be mucosal.

Immunostimulatory nucleic acids are considered to be non-sequence specific when it is not required that they specifically bind to and reduce the expression of a target polynucleotide in order to provoke an immune response. Thus, certain immunostimulatory nucleic acids may comprise a sequence corresponding to a region of a naturally occurring gene or mRNA, but they may still be considered non-sequence specific immunostimulatory nucleic acids.

In one embodiment, the immunostimulatory nucleic acid or oligonucleotide comprises at least one CpG dinucleotide. The oligonucleotide or CpG dinucleotide may be unmethylated or methylated. In another embodiment, the immunostimulatory nucleic acid comprises at least one CpG dinucleotide having a methylated cytosine. In one embodiment, the nucleic acid comprises a single CpG dinucleotide, wherein the cytosine in said CpG dinucleotide is methylated. Methods of immune stimulation using single stranded oligonucleotides and immune stimulatory oligonucleotides.

The immunostimulatory nucleic acid or oligonucleotide comprises capable of inducing an anti-viral or an antibacterial response, in particular, the induction of type I IFN, IL-18 and/or IL-1β by modulating RIG-I.

RNA Activator

Recent studies have found that dsRNA can also activate gene expression, a mechanism that has been termed "small RNA-induced gene activation" or RNAa. See for example Li, L. C. et al. *Proc Natl Acad Sci USA.* (2006), 103(46): 17337-42 and Li L. C. (2008). "Small RNA-Mediated Gene Activation". RNA and the Regulation of Gene Expression: A Hidden Layer of Complexity. Caister Academic Press. ISBN 978-1-904455-25-7. It has been shown that dsRNAs targeting gene promoters induce potent transcriptional activation of associated genes. Endogenous miRNA that cause RNAa has also been found in humans. Check E. Nature (2007). 448 (7156): 855-858.

Another surprising observation is that gene activation by RNAa is long-lasting. Induction of gene expression has been seen to last for over ten days. The prolonged effect of RNAa could be attributed to epigenetic changes at dsRNA target sites.

miRNA Mimics miRNA mimics represent a class of molecules that can be used to imitate the gene modulating activity of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression. miRNA mimics can be designed as mature molecules (e.g. single stranded) or mimic precursors (e.g., pri- or pre-miRNAs).

In one design, miRNA mimics are double stranded molecules (e.g., with a duplex region of between about 16 and about 31 nucleotides in length) and contain one or more sequences that have identity with the mature strand of a given miRNA.

Modifications can comprise 2' modifications (including 2'-O methyl modifications and 2' F modifications) on one or both strands of the molecule and internucleotide modifications (e.g. phorphorthioate modifications) that enhance nucleic acid stability and/or specificity. In addition, miRNA mimics can include overhangs. The overhangs can consist of 1-6 nucleotides on either the 3' or 5' end of either strand and can be modified to enhance stability or functionality.

In one embodiment, a miRNA mimic comprises a duplex region of between 16 and 31 nucleotides and one or more of the following chemical modification patterns: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3' overhang.

Supermirs

A supermir refers to an oligonucleotide, e.g., single stranded, double stranded or partially double stranded, which has a nucleotide sequence that is substantially identical to an miRNA and that is antisense with respect to its target. This term includes oligonucleotides which comprise at least one non-naturally-occurring portion which functions similarly. In a preferred embodiment, the supermir does not include a sense strand, and in another preferred embodiment, the supermir does not self-hybridize to a significant extent. An supermir featured in the invention can have secondary structure, but it is substantially single-stranded under physiological conditions. An supermir that is substantially single-stranded is single-stranded to the extent that less than about 50% (e.g., less than about 40%, 30%, 20%, 10%, or 5%) of the supermir is duplexed with itself. The supermir can include a hairpin segment, e.g., sequence, preferably at the 3' end can self hybridize and form a duplex region, e.g., a duplex region of at least 1, 2, 3, or 4 and preferably less than 8, 7, 6, or 5 nucleotides, e.g., 5 nucleotides. The duplexed region can be connected by a linker, e.g., a nucleotide linker, e.g., 3, 4, 5, or 6 dTs, e.g., modified dTs. In another embodiment the supermir is duplexed with a shorter oligo, e.g., of 5, 6, 7, 8, 9, or 10 nucleotides in length, e.g., at one or both of the 3' and 5' end or at one end and in the non-terminal or middle of the supermir.

Antimirs or miRNA Inhibitors

The terms "antimir" "microRNA inhibitor", "miR inhibitor", or "inhibitor" are synonymous and refer to oligonucleotides or modified oligonucleotides that interfere with the activity of specific miRNAs. Inhibitors can adopt a variety of configurations including single stranded, double stranded (RNA/RNA or RNA/DNA duplexes), and hairpin designs, in general, microRNA inhibitors comprise one or more sequences or portions of sequences that are complementary or partially complementary with the mature strand (or strands) of the miRNA to be targeted, in addition, the miRNA inhibitor may also comprise additional sequences located 5' and 3' to the sequence that is the reverse complement of the mature miRNA. The additional sequences may be the reverse complements of the sequences that are adjacent to the mature miRNA in the pri-miRNA from which the mature miRNA is derived, or the additional sequences may be arbitrary sequences (having a mixture of A, G, C, U, or dT). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. MicroRNA inhibitors, when double stranded, may include mismatches between nucleotides on opposite strands. Furthermore, microRNA inhibitors may be linked to conjugate moieties in order to facilitate uptake of the inhibitor into a cell.

MicroRNA inhibitors, including hairpin miRNA inhibitors, are described in detail in Vermeulen et al., "Double-Stranded Regions Are Essential Design Components Of Potent Inhibitors of RISC Function," RNA 13: 723-730 (2007) and in WO2007/095387 and WO 2008/036825 each of which is incorporated herein by reference in its entirety. A person of ordinary skill in the art can select a sequence from the database for a desired miRNA and design an inhibitor useful for the methods disclosed herein.

Other Oligonucleotides

Because transcription factors recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to upregulate genes that are suppressed by the binding of a transcription factor. Examples of the utilization of decoy oligonucleotides may be found in Mann et al., J. Clin. Invest., 2000, 106: 1071-1075, which is expressly incorporated by reference herein, in its entirety.

U1 adaptor inhibit polyA sites and are bifunctional oligonucleotides with a target domain complementary to a site in the target gene's terminal exon and a 'U1 domain' that binds to the U1 smaller nuclear RNA component of the U1 snRNP (Goraczniak, et al., 2008, Nature Biotechnology, 27(3), 257-263, which is expressly incorporated by reference herein, in its entirety). U1 snRNP is a ribonucleoprotein complex that functions primarily to direct early steps in spliceosome formation by binding to the pre-mRNA exon-intron boundary (Brown and Simpson, 1998, Annu Rev Plant Physiol Plant Mol Biol 49:77-95). Nucleotides 2-11 of the 5'end of U1 snRNA base pair bind with the 5'ss of the pre mRNA. In one embodiment, oligonucleotides of the invention are U1 adaptors. In one embodiment, the U1 adaptor can be administered in combination with at least one other iRNA agent.

An oligonucleotide can include modification of all or some of the sugar groups of the nucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids, e.g., LNA, in which the 2' hydroxyl is connected by a methylene bridge to the 4' carbon of the same ribose sugar and ENA, in which the 2' hydroxyl is connected by an ethylene bridge to the 4' carbon of the same ribose sugar; O-AMINE (AMINE=$NH_2$, alkylamino, dialkylamino, heterocyclyl, arylamino, diaryl amino, heteroaryl amino, diheteroaryl amino, ethylene diamine, polyamino or aminoalkoxy) and $O(CH_2)_n$AMINE, (e.g., AMINE=$NH_2$, alkylamino, dialkylamino, heterocyclyl, arylamino, diaryl amino, heteroaryl amino, or diheteroaryl amino, ethylene diamine, polyamino or aminoalkoxy). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$, alkylamino, dialkylamino, heterocyclyl, arylamino, diaryl amino, heteroaryl amino, or diheteroaryl amino), NHC(O)R (R=alkyl, cycloalkyl, aryl, aralkyl, heteroaryl or sugar); cyano; mercapto; alkyl-thio-alkyl; thioalkoxy; alkyl; cycloalkyl; aryl; alkenyl and alkynyl, which may be optionally substituted with e.g., an amino functionality.

The sugar group can also contain one or more carbons that possess the opposite stereochemical configuration than that of the corresponding carbon in ribose. Thus, an oligonucleotide can include nucleotides containing e.g., arabinose, as the sugar. The monomer can have an alpha linkage at the 1' position on the sugar, e.g., alpha-nucleosides. Oligonucleotides can also include "abasic" sugars, which lack a nucleobase at C-1'. These abasic sugars can also be further containing modifications at one or more of the constituent sugar atoms. Oligonucleotides can also contain one or more sugars that are in the L form, e.g. L-nucleosides. One or more nucleotides of an oligonucleotide may have L-sugar with modifications in place of the modified nucleoside in its entity pursuant to the invention described. The L-sugar has the same sugar and base modification or combinations thereof as in D-sugar. One or more nucleotides of an oligonucleotide having the L-sugar may have a 2'-5' linkage or inverted linkages, e.g. 3'-3', 5'-5', 2'-2' or 2'-3' linkages. These linkages can be placed between two L-sugar moieties, between L- and D-sugars or between two D-sugars in an oligonucleotide bearing a modified L-nucleoside Modification to the sugar group may also include replacement of the 4'-O with a sulfur, nitrogen or $CH_2$ group. Other modifications to the sugar group include deletion of the C2'

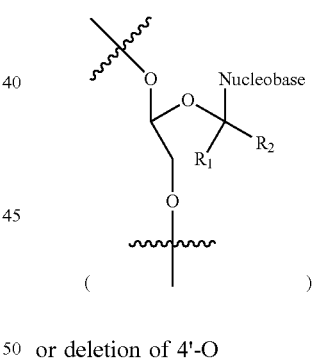

or deletion of 4'-O

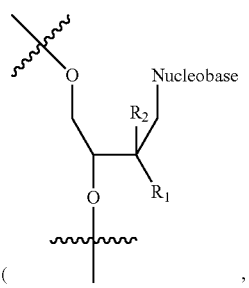

where $R_1$ and $R_2$ independently are H, halogen, $OR_3$, or alkyl; and $R_3$ is H, alkyl, cycloalkyl, aryl, aralkyl, heteroaryl or sugar).

Preferred substitutents are 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH₂-(4'-C) (LNA), 2'-O—CH₂CH₂-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O—CH₂CH₂N(CH₂CH₂NMe₂)₂ and 2'-O-dimethylaminoethyloxyethyl (2'-O-DMAEOE).

One or more nucleotides of an oligonucleotide may have L-sugar with modifications in place of the modified nucleoside in its entity pursuant to the invention described. The L-sugar has the same sugar and base modification or combinations thereof as in D-sugar. One or more nucleotides of an oligonucleotide having the L-sugar may have a 2'-5' linkage or inverted linkages, e.g. 3'-3', 5'-5', 2'-2' or 2'-3' linkages. These linkages can be placed between two L-sugar moieties, between L- and D-sugars or between two D-sugars in an oligonucleotide bearing a modified L-nucleoside. The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

When a linker/phosphate-functional molecular entity-linker/phosphate array is interposed between two strands of a dsRNA, this array can substitute for a hairpin RNA loop in a hairpin-type RNA agent.

Terminal modifications useful for modulating activity include modification of the 5' end with phosphate or phosphate analogs. E.g., in preferred embodiments antisense strands of dsRNAs, are 5' phosphorylated or include a phosphoryl analog at the 5' prime terminus. 5'-phosphate modifications include those which are compatible with RISC mediated gene silencing. Modifications at the 5'-terminal end can also be useful in stimulating or inhibiting the immune system of a subject. In certain embodiments, the 5'-end of the oligonucleotide comprises the modification

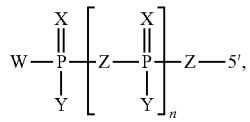

wherein W, X and Y are each independently selected from the group consisting of O, OR (R is hydrogen, alkyl, aryl), S, Se, BR₃ (R is hydrogen, alkyl, aryl), C (i.e. an alkyl group, an aryl group, etc. . . . ), H, NR₂ (R is hydrogen, alkyl, aryl), or OR (R is hydrogen, alkyl or aryl); Z is independently for each occurrence O, S, CH₂, or NR (R is hydrogen, alkyl, aryl); and n is 0-2.

Suitable modifications include: 5'-monophosphate ((HO)₂(O)P—O-5'); 5'-diphosphate ((HO)₂(O)P—O—P(HO)(O)—O-5'); 5'-triphosphate ((HO)₂(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)₂(S)P—O-5'); 5'-monodithiophosphate (phosphorodithioate; (HO)(HS)(S)P—O-5'), 5'-phosphorothiolate ((HO)₂(O)P—S-5'); any additional combination of oxygen/sulfur replaced monophosphate, diphosphate and triphosphates (e.g. 5'-alpha-thiotriphosphate, 5'-b eta-thiotriphosphate, 5'-gamma-thiotriphosphate, etc.), 5'-phosphoramidates ((HO)₂(O)P—NH-5', (HO)(NH₂)(O)P—O-5'), 5'-alkylphosphonates (R=alkyl=methyl, ethyl, isopropyl, propyl, etc., e.g. RP(OH)(O)—O-5'-, (OH)₂(O)P-5'-CH₂—), 5'-alkyletherphosphonates (R=alkylether=methoxymethyl (MeOCH₂—), ethoxymethyl, etc., e.g. RP(OH)(O)—O-5'-); two or more phosphates or all phosphate mimics described with separation by substituted or unsubstituted alkyl, alkenyl or alkynyl spacings: e.g., ((HO)2(X)P—O[—(CH₂)ₐ—O—P(X)(OH)—O]ᵦ-5', ((HO)2(X)P—O[—(CH₂)ₐ—P(X)(OH)—O]ᵦ-5', ((HO)2(X)P—[—(CH₂)ₐ—O—P(X)(OH)—O]ᵦ-5'; dialkyl terminal phosphates and phosphate mimics: HO[—(CH₂)ₐ—O—P(X)(OH)—O]ᵦ-5', H₂N[—(CH₂)ₐ—O—P(X)(OH)—O]ᵦ-5', H[—(CH₂)ₐ—O—P(X)(OH)—O]ᵦ-5', Me₂N[—(CH₂)ₐ—O—P(X)(OH)—O]ᵦ-5', HO[—(CH₂)ₐ—P(X)(OH)—O]ᵦ-5', H₂N[—(CH₂)ₐ—P(X)(OH)—O]ᵦ-5', H[—(CH₂)ₐ—P(X)(OH)—O]ᵦ-5', Me₂N[—(CH₂)ₐ—P(X)(OH)—O]ᵦ-5' Other embodiments include replacement of oxygen/sulfur with BH₃, BH₃⁻ and/or Se. In one occurrence at terminals of the oligonucleotides, the phosphate and phosphate mimics described are β to the sugar moiety and in another occurrence the phosphate and phosphate mimics are β to the sugar moiety; or in another occurrence both α and β phosphate bearing moieties are simultaneously present.

In another embodiment, the phosphate groups described above are placed at the 3'-end of the oligonucleotided, for example at the 2' and/or the 3' position of the 3'-nucleoside sugar.

In one embodiment, the configuration of phosphate or phosphate mimics at 5' terminal is β to the sugar moiety.

In one embodiment, the configuration of phosphate or phosphate mimics at 5' terminal is α to the sugar moiety.

In one embodiment, the configuration of phosphate or phosphate mimics at 3' terminal is β to the sugar moiety.

In another embodiment, the configuration of phosphate or phosphate mimics at 3' terminal is α to the sugar moiety.

In one embodiment both α and β phosphate or phosphate mimics are simultaneously present at the terminals Terminal modifications can also be useful for monitoring distribution, and in such cases the preferred groups to be added include fluorophores, e.g., fluorscein or an Alexa dye, e.g., Alexa 488. Terminal modifications can also be useful for enhancing uptake, useful modifications for this include cholesterol. Terminal modifications can also be useful for cross-linking an RNA agent to another moiety; modifications useful for this include mitomycin C, psoralen and derivatives thereof.

In one embodiment, one or more nucleotides of an oligonucleotide may have a 5'-5', 3'-3', 3'-2', 2'-5', 2'-3' or a 2'-2' linkage, preferably a 2'-5' linkage. In certain embodiments, the last nucleotide on the terminal end is linked via an inverted linkages, e.g. 3'-3', 5'-5', 2'-2' or 2'-3' linkage to the rest of the oligonucleotide.

An oligonucleotide may further comprise at least one 5'-pyrimidine-purine-3' (5'-PyPU-3') dinucleotide motif wherein the pyrimidine ribose sugar is modified at the 2'-position. In certain embodiments, the pyrimidine ribose sugar is replaced by a non ribose moiety, e.g., a six membered ring. In certain other embodiments, the oligonucleotide comprises at least one 5'-pyrimidine-purine-3' (5'-PyPu-3') dinucleotide wherein the ribose sugar of the pyrimidine is modified with a modification chosen independently from a group consisting of 2'-H, 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA) and 2'-O—CH$_2$CH$_2$-(4'-C) (ENA). In one embodiment, the 5'-most pyrimidines in all occurrences of sequence motif 5'-pyrimidine-purine-3' (5'-PyPu-3') dinucleotide in the oligonucleotide comprise a sugar 2'-modification.

In certain embodiments, the oligonucleotide comprises at least one 5'-PyPu-3' dinucleotide motif where the C5 position of the pyrimidine is conjugated with a stabilizing moiety, e.g., a cationic group. In one embodiment, pyrimidines in all 5'-PyPu-3' dinucleotide motif comprise a stabilizing moiety at the C5 position.

In certain embodiments, the oligonucleotide comprises at least one 5'-PyPu-3' dinucleotide motif where the $N^2$, $N^6$, and/or $C^8$ position of the purine is conjugated with a stabilizing moiety, e.g., a cationic group. In one embodiment, purines in all 5'-PyPu-3' dinucleotide motifs comprise a stabilizing moiety at the $N^2$, $N^6$, and/or $C^8$ position.

In certain embodiments, both the pyrimidine and purine in the 5'-PyPu-3' dinucleotide motif are conjugated with stabilizing groups.

In certain embodiments, the internucleotide linkage between 3'- of a pyrimidine and 5'- of a purine is a non-phosphodiester linkage described herein.

In certain embodiments, the both the pyrimidine and the purine in a 5'-PyPu-3' dinucleotide motif are unmodified and the internucleotide linkage between them is a non-phosphodiester linkage described herein.

In certain embodiments, both the pyrimidine and the purine in a 5'-PyPu-3' dinucleotide motif comprise unmodified sugars, e.g., 2'-OH and at least one of them comprises a nucleobase modification. In one embodiment, both the pyrimidine and the purine in a 5'-PyPu-3' dinucleotide motif comprise unmodified sugars, e.g., 2'-OH and both of them comprise a nucleobase modification.

In certain embodiments, the oligonucleotide comprises at least one 5'-PyPu-3'-dinucleotide motif where the pyrimide comprises a modification at the 2'-position, the internucleotide linkage is a non-phosphodiester linkage and at least one of the pyrimidine and the purine comprises a nucleobase modification. In one embodiment, the pyrimidine comprises the nucleobase modification. In another embodiment, the purine comprises the nucleobase modification. In yet another embodiment, both the pyrimidine and the purine comprise the nucleobase modification.

In certain embodiments, the oligonucleotide comprises at least one 5'-PyPu-3'-dinucleotide motif where the purine comprises a modification at the 2'-position, the internucleotide linkage is a non-phosphodiester linkage and at least one of the pyrimidine and the purine comprises a nucleobase modification. In one embodiment, the pyrimidine comprises the nucleobase modification. In another embodiment, the purine comprises the nucleobase modification. In yet another embodiment, both the pyrimidine and the purine comprise the nucleobase modification.

In one embodiment, the single stranded siRNA (ss siRNA) and double stranded siRNA (ds siRNA) of the invention comprises a motif selected from the group consisting of:

(a) 2'-modified uridines in all occurrences of the sequence motif 5'-uridine-adenosine-3' (5'-UA-3'),
(b) 2'-modified uridines in all occurrences of the sequence motif 5'-uridine-guanosine-3' (5'-UG-3'),
(c) 2'-modified cytidines in all occurrences of the sequence motif 5'-cytidine-adenosine-3' (5'-CA-3'),
(d) 2'-modified cytidines in all occurrences of the sequence motif 5'-cytidine-Guanosine-3' (5'-CA-3'),
(e) 2'-modified 5'-most uridines in all occurrences of the sequence motif 5'-uridine-uridine-3' (5'-UU-3'),
(f) 2'-modified 5'-most cytidines in all occurrences of the sequence motif 5'-cytidine-cytidine-3' (5'-CC-3'),
(g) 2'-modified cytidines in all occurrences of the sequence motif 5'-cytidine-uridine-3' (5'-CU-3'),
(h) 2'-modified uridines in all occurrences of the sequence motif 5'-uridine-cytidine-3' (5'-UC-3'), and
(h) combinations thereof;

and wherein siRNA comprises at least one modification at internucleotide linkage, nucleobase and/or 2' sugar modification. Examples of the non-phosphodiester modification includes, but not limited to phosphorothioate, phosphorodithioate, phosphotriesters, aminoalkylphosphotriesters, methyl and other alkyl phosphonates, selenophosphates, phosphoramidates and boranophosphates. Examples of the nucleobase modifications include, but not limited to: C-5 pyrimidine with an alkyl group or aminoalkyls and other cationic groups such as guanidinium and amidine functionalities, $N^2$- and $N^6$- with an alkyl group or aminoalkyls and other cationic groups such as guanidinium and amidine functionalities of purines, G-clamps, guanidinium G-clamps, and pseudouridine known in the art or G-clamps and pseudourines provided herein in. Examples of 2' modifications includes those know in the art, as well as ones disclosed herein. In one example, when there is a 2' OH moiety present in the said motif, at least either internucleotide linkage or nucleobase or both must be modified. In another example, 2'-position of the sugar of the 3'-most nucleoside is modified but not of the 5'-most nucleoside and vice versa, then at least either the internucleotide linkage or nucleobase of the 5'-most or 3'-most or both the nucleobase of the motif or both internucleotide linkage and nucleobase must be modified. In another example, both nucleoside in the motif bear unmodified ribo-sugar (i.e., 2'-OH on both nucleoside), then at least either the internucleotide linkage or nucleobase of the 5'-most or 3'-most or both the nucleobase, or both internucleotide linkage and at least one of the nucleobases of the motif must be modified. The preferred nucleobase modification bears a cationic amino group connected via an appropriate alkyl alkenyl or a tether with an amide linkages.

A double-stranded oligonucleotide may include at least one 5'-uridine-adenine-3' (5'-UA-3') dinucleotide wherein the uridine is a 2'-modified nucleotide, or a terminal 5'-uridine-guanine-3' (5'-UG-3') dinucleotide, wherein the 5'-uridine is a 2'-modified nucleotide, or a terminal 5'-cytidine-adenine-3' (5'-CA-3') dinucleotide, wherein the 5'-cytidine is a 2'-modified nucleotide, or a terminal 5'-uridine-uridine-3' (5'-UU-3') dinucleotide, wherein the 5'-uridine is a 2'-modified nucleotide, or a terminal 5'-cytidine-cytidine-3' (5'-CC-3') dinucleotide, wherein the 5'-cytidine is a 2'-modified nucleotide, or a terminal 5'-cytidine-uridine-3' (5'-CU-3') dinucleotide, wherein the 5'-cytidine is a 2'-modified nucleotide, or a terminal 5'-uridine-cytidine-3' (5'-UC-3') dinucleotide, wherein the 5'-uridine is a 2'-modified nucleotide. Double-stranded oligonucleotides including these modifications are particularly stabilized against endonuclease activity.

Modifications and monomers described herein may be used to asymmetrically modified a double-stranded oligonucleotide. An asymmetrically modified double-stranded oligonucleotide is one in which one strand has a modification which is not present on the other strand. As such, an asymmetrical modification is a modification found on one strand but not on the other strand. Any modification, e.g., any modification described herein, can be present as an asymmetrical modification. An asymmetrical modification can confer any of the desired properties associated with a modification, e.g., those properties discussed herein. For example, an asymmetrical modification can confer resistance to degradation, an alteration in half life; target the oligonucleotide to a particular target, e.g., to a particular tissue; modulate, e.g., increase or decrease, the affinity of a strand for its complement or target sequence; or hinder or promote modification of a terminal moiety, e.g., modification by a kinase or other enzymes involved in the RISC mechanism pathway. The designation of a modification as having one property does not mean that it has no other property, e.g., a modification referred to as one which promotes stabilization might also enhance targeting. Asymmetrical modifications can include those in which only one strand is modified as well as those in which both are modified.

When the two strands of double-stranded oligonucleotide are linked together, e.g. a hairpin or a dumbbell, the two strands of the double stranded region may also be strands forming asymmetrically modified. For example, first strand of the double-stranded region comprises at least one asymmetric modification that is not present in the second strand of the double stranded region or vice versa.

While not wishing to be bound by theory or any particular mechanistic model, it is believed that asymmetrical modification allows a double-stranded RNAi agent to be optimized in view of the different or "asymmetrical" functions of the sense and antisense strands. For example, both strands can be modified to increase nuclease resistance, however, since some changes can inhibit RISC activity, these changes can be chosen for the sense stand. In addition, since some modifications, e.g., a ligand, can add large bulky groups that, e.g., can interfere with the cleavage activity of the RISC complex, such modifications are preferably placed on the sense strand. Thus, ligands, especially bulky ones (e.g. cholesterol), are preferentially added to the sense strand. The ligand may be present at either (or both) the 5' or 3' end of the sense strand of a RNAi agent.

Each strand can include one or more asymmetrical modifications. By way of example: one strand can include a first asymmetrical modification which confers a first property on the oligonucleotide and the other strand can have a second asymmetrical modification which confers a second property on the oligonucleotide. For example, one strand, e.g., the sense strand can have a modification which targets the oligonucleotide to a tissue, and the other strand, e.g., the antisense strand, has a modification which promotes hybridization with the target gene sequence.

In some embodiments both strands can be modified to optimize the same property, e.g., to increase resistance to nucleolytic degradation, but different modifications are chosen for the sense and the antisense strands, because the modifications affect other properties as well.

Multiple asymmetric modifications can be introduced into either or both of the sense and antisense strand. A strand can have at least 1, 2, 3, 4, 5, 6, 7, 8, or more modifications and all or substantially all of the monomers, e.g., nucleotides of a strand can be asymmetrically modified.

In certain embodiments, the asymmetric modifications are chosen so that only one of the two strands of double-stranded RNAi agent is effective in inducing RNAi. Inhibiting the induction of RNAi by one strand may reduce the off target effects due to cleavage of a target sequence by that strand.

Oligonucleotide Production

The oligonucleotide compounds of the invention can be prepared using solution-phase or solid-phase organic synthesis. Organic synthesis offers the advantage that the oligonucleotide strands comprising non-natural or modified nucleotides can be easily prepared. Any other means for such synthesis known in the art may additionally or alternatively be employed. It is also known to use similar techniques to prepare other oligonucleotides, such as the phosphorothioates, phosphorodithioates and alkylated derivatives. The double-stranded oligonucleotide compounds of the invention may be prepared using a two-step procedure. First, the individual strands of the double-stranded molecule are prepared separately. Then, the component strands are annealed.

Regardless of the method of synthesis, the oligonucleotide can be prepared in a solution (e.g., an aqueous and/or organic solution) that is appropriate for formulation. For example, the oligonucleotide preparation can be precipitated and redissolved in pure double-distilled water, and lyophilized. The dried oligonucleotide can then be resuspended in a solution appropriate for the intended formulation process. Teachings regarding the synthesis of particular modified oligonucleotides may be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having .beta.-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-fluoro-oligonucleotides.

Ligands

A wide variety of entities can be coupled to the oligonucleotides of the present invention. Ligands can include naturally occurring molecules, or be recombinant or synthetic molecules. Preferred moieties are ligands, which are coupled, preferably covalently, either directly or indirectly via an intervening tether.

In preferred embodiments, a ligand alters the distribution, targeting or lifetime of the molecule into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Ligands providing enhanced affinity for a selected target are also termed targeting ligands.

Some ligands can have endosomolytic properties. The endosomolytic ligands promote the lysis of the endosome and/or transport of the composition of the invention, or its components, from cellular compartments such as the endosome, lysosome, endoplasmic reticulum (ER), golgi apparatus, microtubule, peroxisome, or other vesicular bodies within the cell, to the cytoplasm of the cell. The endosomolytic ligand may be a polyanionic peptide or peptidomimetic which shows pH-dependent membrane activity and fusogenicity. In one embodiment, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In one embodiment, the endosomolytic component may contain a chemical group (e.g., an amino acid) which will undergo a change in charge or protonation in response to a change in pH. The endosomolytic component may be linear or branched.

Ligands can include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Methods of Use

One aspect of the present invention relates to a method of modulating the expression of a target gene in a cell. The method comprises: (a) providing a composition of the invention; (b) contacting a cell with the composition; and (c) allowing the cell to internalize the composition. The method can be performed in vitro, ex vivo or in vivo, e.g., to treat a subject identified as being in need of treatment by a composition of the invention.

In certain embodiments, the cell is a mammalian cell.

In yet another aspect, the invention provides a method for modulating the expression of the target gene in a mammal. The method comprises: administering a composition featured in the invention to the mammal such that expression of the target gene is modulated. The composition may be administered by any means known in the art including, but not limited to oral or parenteral routes, including intravenous, intramuscular, subcutaneous, transdermal, airway (aerosol), nasal, rectal, and topical (including buccal and sublingual) administration. In preferred embodiments, the compositions are administered by intravenous infusion or injection. Target genes include genes promoting unwanted cell proliferation, growth factor gene, growth factor receptor gene, genes expressing kinases, an adaptor protein gene, a gene encoding a G protein super family molecule, a gene encoding a transcription factor, a gene which mediates angiogenesis, a viral gene, a gene required for viral replication, a cellular gene which mediates viral function, a gene of a bacterial pathogen, a gene of an amoebic pathogen, a gene of a parasitic pathogen, a gene of a fungal pathogen, a gene which mediates an unwanted immune response, a gene which mediates the processing of pain, a gene which mediates a neurological disease, an allene gene found in cells characterized by loss of heterozygosity, or one allege gene of a polymorphic gene.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims.

The phrases "2'-modification" and "2'-modified nucleotide" refer to a nucleotide unit having a sugar moiety, for example a ribosyl moiety, that is modified at the 2'-position such that the hydroxyl group (2'-OH) is replaced by, for example, —F, —H, —CH$_3$, —CH$_2$CH$_3$, —OCH—$_3$, —OCH$_2$CH$_3$, —OCH$_2$CH$_2$OMe, —OCH$_2$C(=O)NHMe, —OCH$_2$-(4'-C) (a so-called "LNA sugar modification"), or —OCH$_2$CH$_2$-(4'-C) (a so-called "ENA sugar modification"). For example, the phrases "2'-fluoro modification" and "2'-fluoro modified nucleotide" refer to a nucleotide unit having a sugar moiety, for example a ribosyl moiety, that is modified at the 2'-position such that the hydroxyl group (2'-OH) is replaced by a fluoro group (2'-F). U.S. Pat. Nos. 6,262,241, and 5,459,255 (both of which are incorporated by reference), are drawn to, inter alia, methods of synthesizing 2'-fluoro modified nucleotides and oligonucleotides.

The phrase "antisense strand" as used herein, refers to a polynucleotide that is substantially or 100% complementary to a target nucleic acid of interest. An antisense strand may comprise a polynucleotide that is RNA, DNA or chimeric RNA/DNA. For example, an antisense strand may be complementary, in whole or in part, to a molecule of messenger RNA, an RNA sequence that is not mRNA (e.g., tRNA, rRNA and hnRNA) or a sequence of DNA that is either coding or non-coding. The phrase "antisense strand" includes the antisense region of both polynucleotides that are formed from two separate strands, as well as unimolecular polynucleotides that are capable of forming hairpin structures. The terms "antisense strand" and "guide strand" are used interchangeably herein.

The phrase "sense strand" refers to a polynucleotide that has the same nucleotide sequence, in whole or in part, as a target nucleic acid such as a messenger RNA or a sequence of DNA. The sense strand is not incorporated into the functional riboprotein RISC. The terms "sense strand" and "passenger strand" are used interchangeably herein.

The term "duplex" includes a region of complementarity between two regions of two or more polynucleotides that comprise separate strands, such as a sense strand and an antisense strand, or between two regions of a single contiguous polynucleotide.

As used herein, "specifically hybridizable" and "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., a to t, a to u, c to g), or in any other manner that allows for the formation of stable duplexes. "Perfect complementarity" or 100% complementarity refers to the situation in which each nucleotide unit of one polynucleotide strand can hydrogen bond with each nucleotide unit of a second polynucleotide strand. Less than perfect complementarity refers to the situation in which some, but not all, nucleotide units of two strands can hydrogen bond with each other. "Substantial complementarity" refers to polynucleotide strands exhibiting 90% or greater complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

The term "off-target" and the phrase "off-target effects" refer to any instance in which an RNAi agent against a given target causes an unintended affect by interacting either directly or indirectly with another mRNA sequence, a DNA sequence or a cellular protein or other moiety. For example, an "off-target effect" may occur when there is a simultaneous degradation of other transcripts due to partial homology or complementarity between that other transcript and the sense and/or antisense strand of a double-strained RNAi agent.

The phrase "first 5' terminal nucleotide" includes first 5' terminal antisense nucleotides and first 5' terminal antisense nucleotides. "First 5' terminal antisense nucleotide" refers to the nucleotide of the antisense strand that is located at the 5' most position of that strand with respect to the bases of the antisense strand that have corresponding complementary bases on the sense strand. Thus, in a double stranded polynucleotide that is made of two separate strands, it refers to the 5' most base other than bases that are part of any 5' overhang on the antisense strand. When the first 5' terminal antisense nucleotide is part of a hairpin molecule, the term "terminal" refers to the 5' most relative position within the antisense region and thus is the 5" most nucleotide of the antisense region. The phrase "first 5" terminal sense nucleotide" is defined in reference to the sense nucleotide. In molecules comprising two separate strands, it refers to the nucleotide of the sense strand that is located at the 5' most position of that strand with respect to the bases of the sense strand that have corresponding complementary bases on the antisense strand. Thus, in a double stranded polynucleotide that is made of two separate strands, it is the 5' most base other than bases that are part of any 5' overhang on the sense strand.

In one embodiment, an siRNA compound is "sufficiently complementary" to a target RNA, e.g., a target mRNA, such that the siRNA compound silences production of protein encoded by the target mRNA. In another embodiment, the siRNA compound is "exactly complementary" to a target RNA, e.g., the target RNA and the siRNA compound anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, In one embodiment, the siRNA compound specifically discriminates a single-nucleotide difference. In this case, the siRNA compound only mediates RNAi if exact complementary is found in the region (e.g., within 7 nucleotides of) the single-nucleotide difference.

In one embodiment, oligonucleotides of the invention are prepared by connecting nucleosides with optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12, pp. 2223-2311 (1992).

In one embodiment, nucleosides having reactive phosphorus groups are provided that are useful for forming internucleoside linkages including for example phosphodiester and phosphorothioate internucleoside linkages. Such reactive phosphorus groups are known in the art and contain phosphorus atoms in $P^{III}$ or $P^{V}$ valence state including, but not limited to, phosphoramidite, H-phosphonate, phosphate triesters and phosphorus containing chiral auxiliaries. A preferred synthetic solid phase synthesis utilizes phosphoramidites ($P^{III}$ chemistry) as reactive phosphites. The intermediate phosphite compounds are subsequently oxidized to the Pv state using known methods to yield, in preferred embodiments, phosphodiester or phosphorothioate internucleotide linkages.

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, non-phosphorus containing internucleoside linking groups such as formacetyl and methyl eneimino, and neutral non-ionic internucleoside linking groups such as amide-3 (3'-CH$_2$—C(=O)—N(H)-5'), amide-4 (3'-CH$_2$—N(H)—C(=O)-5').

As used herein the term "alternating motif" refers to a an oligonucleotide comprising a contiguous sequence of linked monomer subunits wherein the monomer subunits have two different types of sugar groups that alternate for essentially the entire sequence of the oligonucleotide. Oligonucleotides having an alternating motif can be described by the formula: 5'-A(-L-B-L- A)n(-L-B)nn-3' where A and B are monomelic subunits that have different sugar groups, each L is an internucleoside linking group, n is from about 4 to about 12 and nn is 0 or 1. This permits alternating oligonucleotides from about 9 to about 26 monomer subunits in length. This length range is not meant to be limiting as longer and shorter oligonucleotides are also amenable to the present invention. In one embodiment, one of A and B is a 2'-modified nucleoside as provided herein.

As used herein the term "uniformly fully modified motif" refers to an oligonucleotide comprising a contiguous sequence of linked monomer subunits that each have the same type of sugar group. In one embodiment, the uniformly fully modified motif includes a contiguous sequence of nucleosides of the invention. In one embodiment, one or both of the 3' and 5'-ends of the contiguous sequence of the nucleosides provided herein, comprise terminal groups such as one or more unmodified nucleosides.

As used herein the term "hemimer motif" refers to an oligonucleotide having a short contiguous sequence of monomer subunits having one type of sugar group located at the 5' or the 3' end wherein the remainder of the monomer subunits have a different type of sugar group. In general, a hemimer is an oligomeric compound of uniform sugar groups further comprising a short region (1, 2, 3, 4 or about 5 monomelic subunits) having uniform but different sugar groups and located on either the 3' or the 5' end of the oligomeric compound. In one embodiment, the hemimer motif comprises a contiguous sequence of from about 10 to about 28 monomer subunits of one type with from 1 to 5 or from 2 to about 5 monomer subunits of a second type located at one of the termini. In one embodiment, a hemimer is a contiguous sequence of from about 8 to about 20 β-D-2'-deoxyribonucleosides having from 1-12 contiguous nucleosides of the invention located at one of the termini. In one embodiment, a hemimer is a contiguous sequence of from about 8 to about 20 β-D-2'-deoxyribonucleosides having from 1-5 contiguous nucleosides of the invention located at one of the termini. In one embodiment, a hemimer is a contiguous sequence of from about 12 to about 18 β-D-2'-deoxyribo-nucleosides having from 1-3 contiguous nucleosides of the invention located at one of the termini. In one embodiment, a hemimer is a contiguous sequence of from about 10 to about 14 β-D-2'-deoxyribonucleosides having from 1-3 contiguous nucleosides of the invention located at one of the termini.

As used herein the term "blockmer motif" refers to an oligonucleotide comprising an otherwise contiguous sequence of monomer subunits wherein the sugar groups of each monomer subunit is the same except for an interrupting internal block of contiguous monomer subunits having a different type of sugar group. A blockmer overlaps somewhat with a gapmer in the definition but typically only the monomer subunits in the block have non-naturally occurring sugar groups in a blockmer and only the monomer subunits in the external regions have non-naturally occurring sugar groups in a gapmer with the remainder of monomer subunits in the blockmer or gapmer being β-D-2'-deoxyribonucleosides or β-D-ribonucleosides. In one embodiment, blockmer oligonucleotides are provided herein wherein all of the monomer subunits comprise non-naturally occurring sugar groups.

As used herein the term "positionally modified motif" is meant to include an otherwise contiguous sequence of monomer subunits having one type of sugar group that is interrupted with two or more regions of from 1 to about 5 contiguous monomer subunits having another type of sugar group. Each of the two or more regions of from 1 to about 5 contiguous monomer subunits are independently uniformly modified with respect to the type of sugar group. In one embodiment, each of the two or more regions have the same type of sugar group. In one embodiment, each of the two or more regions have a different type of sugar group. In one embodiment, positionally modified oligonucleotides are provided comprising a sequence of from 8 to 20 β-D-2'-deoxyribonucleosides that further includes two or three regions of from 2 to about 5 contiguous nucleosides of the invention. Positionally modified oligonucleotides are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar groups of the external regions being different than the sugar groups of the internal region and wherein the sugar group of each monomer subunit within a particular region is the same. When the sugar groups of the external regions are the same the gapmer is a symmetric gapmer and when the sugar group used in the 5'-external region is different from the sugar group used in the 3'-external region, the gapmer is an asymmetric gapmer. In one embodiment, the external regions are small (each independently 1, 2, 3, 4 or about 5 monomer subunits) and the monomer subunits comprise non-naturally occurring sugar groups with the internal region comprising β-D-2'-deoxyribonucleosides. In one embodiment, the external regions each, independently, comprise from 1 to about 5 monomer subunits having non-naturally occurring sugar groups and the internal region comprises from 6 to 18 unmodified nucleosides. The internal region or the gap generally comprises β-D-2'-deoxyribo-nucleosides but can comprise non-naturally occurring sugar groups.

In one embodiment, the gapped oligonucleotides comprise an internal region of β-D-2'-deoxyribonucleosides with one of the external regions comprising nucleosides of the invention. In one embodiment, the gapped oligonucleotide comprise an internal region of β-D-2'-deoxyribonucleosides with both of the external regions comprising nucleosides of the invention. In one embodiment, the gapped oligonucleotide comprise an internal region of β-D-2'-deoxyribonucleosides with both of the external regions comprising nucleosides of the invention. In one embodiment, gapped oligonucleotides are provided herein wherein all of the monomer subunits comprise non-naturally occurring sugar groups. In one embodiment, gapped oligonucleotides are provided comprising one or two nucleosides of the invention at the 5'-end, two or three nucleosides of the invention at the 3'-end and an internal region of from 10 to 16 β-D-2'-deoxyribonucleosides. In one embodiment, gapped oligonucleotides are provided comprising one nucleoside of the invention at the 5'-end, two nucleosides of the invention at the 3'-end and an internal reg ion of from 10 to 16 β-D-2'-deoxyribonucleosides. In one embodiment, gapped oligonucleotides are provided comprising two nucleosides of the invention at the 5'-end, two nucleosides of the invention at the 3'-end and an internal region of from 10 to 14 β-D-2'-deoxyribonucleosides. In one embodiment, gapped oligonucleotides are provided that are from about 10 to about 21 monomer subunits in length. In one embodiment, gapped oligonucleotides are provided that are from about 12 to about 16 monomer subunits in length. In one embodiment, gapped oligonucleotides are provided that are from about 12 to about 14 monomer subunits in length.

The phrase "pharmaceutically acceptable carrier or diluent" includes compositions that facilitate the introduction of nucleic acid therapeutics such as siRNA, dsRNA, dsDNA, shRNA, microRNA, antimicroRNA, antagomir, antimir, antisense, aptamer or dsRNA/DNA hybrids into a cell and includes but is not limited to solvents or dispersants, coatings, anti-infective agents, isotonic agents, and agents that mediate absorption time or release of the inventive polynucleotides and double stranded polynucleotides. The phrase "pharmaceutically acceptable" includes approval by a regulatory agency of a government, for example, the U.S. federal government, a non-U.S. government, or a U.S. state government, or inclusion in a listing in the U.S. Pharmacopeia or any other generally recognized pharmacopeia for use in animals, including in humans.

The terms "silence" and "inhibit the expression of" and related terms and phrases, refer to the at least partial suppression of the expression of a gene targeted by an siRNA or siNA, as manifested by a reduction of the amount of mRNA transcribed from the target gene which may be isolated from a first cell or group of cells in which the target gene is transcribed and which has or have been treated such that the expression of the target gene is inhibited, as compared to a second cell or group of cells substantially identical to the first cell or group of cells but which has or have not been so treated (i.e., control cells).

The term "halo" refers to any radical of fluorine, chlorine, bromine or iodine.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substitutent groups.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as (C1-C6)alkanoyl (e.g., formyl, acetyl, propionyl, butyryl, valeryl, caproyl, t-butylacetyl, etc.), (C3-Ce)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The term "alkyl" refers to saturated and unsaturated non-aromatic hydrocarbon chains that may be a straight chain or branched chain, containing the indicated number of carbon atoms (these include without limitation propyl, allyl, or propargyl), which may be optionally inserted with N, O, or S. For example, $C_1$-$C_{10}$ indicates that the group may have from 1 to 10 (inclusive) carbon atoms in it. The term "alkoxy" refers to an —O-alkyl radical. The term "alkylene" refers to a divalent alkyl (i.e., —R—). The term "alkylenedioxo" refers to a divalent species of the structure —O—R—O—, in which R represents an alkylene. The term "aminoalkyl" refers to an alkyl substituted with an amino. The term "mercapto" refers to an —SH radical. The term "thioalkoxy" refers to an —S-alkyl radical.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" or "heterocyclic" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, oxo, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, ureido or conjugate groups.

In many cases, protecting groups are used during preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative hydroxyl protecting groups, for example, are disclosed by Beaucage et al. (*Tetrahedron* 1992, 48, 2223-2311). Further hydroxyl protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethyl silylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Evaluation of Candidate RNAs

One can evaluate a candidate RNA agent, e.g., a modified RNA, for a selected property by exposing the agent or modified molecule and a control molecule to the appropriate conditions and evaluating for the presence of the selected property. For example, resistance to a degradant can be evaluated as follows. A candidate modified RNA (and a control molecule, usually the unmodified form) can be exposed to degradative conditions, e.g., exposed to a milieu, which includes a degradative agent, e.g., a nuclease. E.g., one can use a biological sample, e.g., one that is similar to a milieu, which might be encountered, in therapeutic use, e.g., blood or a cellular fraction, e.g., a cell-free homogenate or disrupted cells. The candidate and control could then be evaluated for resistance to degradation by any of a number of approaches. For example, the candidate and control could be labeled prior to exposure, with, e.g., a radioactive or enzymatic label, or a fluorescent label, such as Cy3 or Cy5. Control and modified RNA's can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to silence gene expression. For example, a cell, e.g., a mammalian cell, such as a mouse or human cell, can be co-transfected with a plasmid expressing a fluorescent protein, e.g., GFP, and a candidate RNA agent homologous to the transcript encoding the fluorescent protein (see, e.g., WO 00/44914). For example, a modified dsiRNA homologous to the GFP mRNA can be assayed for the ability to inhibit GFP expression by monitoring for a decrease in cell fluorescence, as compared to a control cell, in which the transfection did not include the candidate dsiRNA, e.g., controls with no agent added and/or controls with a non-modified RNA added. Efficacy of the candidate agent on gene expression can be assessed by comparing cell fluorescence in the presence of the modified and unmodified dssiRNA compounds.

In an alternative functional assay, a candidate dssiRNA compound homologous to an endogenous mouse gene, for example, a maternally expressed gene, such as c-mos, can be injected into an immature mouse oocyte to assess the ability of the agent to inhibit gene expression in vivo (see, e.g., WO 01/36646). A phenotype of the oocyte, e.g., the ability to maintain arrest in metaphase II, can be monitored as an indicator that the agent is inhibiting expression. For example, cleavage of c-mos mRNA by a dssiRNA compound would cause the oocyte to exit metaphase arrest and initiate parthenogenetic development (Colledge et al. Nature 370: 65-68, 1994; Hashimoto et al. Nature, 370:68-71, 1994). The effect of the modified agent on target RNA levels can be verified by Northern blot to assay for a decrease in the level of target mRNA, or by Western blot to assay for a decrease in the level of target protein, as compared to a negative control. Controls can include cells in which with no agent is added.

Kits

In certain other aspects, the invention provides kits that include a suitable container containing a pharmaceutical formulation of an RNAi agent. In one embodiment the individual components of the pharmaceutical formulation may be provided in one container. Alternatively, it may be desirable to provide the components of the pharmaceutical formulation separately in two or more containers, e.g., one container for an RNAi agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

SYNTHETIC METHODS AND EXAMPLES

Exonuclease End Caps
Building Blocks

Preparation of Compound 2: 4-Hydroxy-L-prolinol-DMTr-N-6-hexyl amine 1 (2 g, 3.80 mmol), DMAP (93 mg, 4.5 mmol), acetic anhydride (426 µl, 4.5 mmol) and pyridine (2 ml) were stirred in $CH_2Cl_2$ (40 ml) for 40 min at room temperature (r.t.). After aqueous work up, the di-acetyl product was purified by column chromatography, and treated with methanolic ammonia solution (10 ml) for overnight at room temperature. TLC showed complete reaction. Compound 2 (1.67 g, 73.6%) was isolated after aqueous work up and column chromatography. Yield: 1.67 g, 73.6%. Electrospray MS (+ve) for $C_{34}H_{42}N_2NaO_6$ $(M+Na)^+$ calcd. 597.7, found 597.3.

Preparation of Compound 3: Compound 2 (1 g, 1.67 mmol) in $CH_2Cl_2$ (40 ml) was treated with DMAP (957.7 mg, 7.84 mmol) and succinic anhydride (645 mg, 6.44 mmol) then stirred for overnight at room temperature. After aqueous work up, the product 3 obtained as a quantitative yield. Electrospray MS (+ve) for $C_{38}H_{45}N_2NaO_9$ $(M+Na)^+$ calcd. 696.76, found 696.3.

Preparation of CPG 4: Compound 3 (1.5 g, 2.15 mmol) in DMF (200 ml), HBTU (937 mg, 2.47 mmol), DIEA (1.33 ml, 7.60 mmol) then $CPG-NH_2$ (140 µmol/g, 15 g, 2.1 mmol) were added in succession. The mixture was shaken for 3.5 h at r.t. then the solid was collected by filtration, washed with $CH_2Cl_2$ (100 ml), 10% $MeOH/CH_2Cl_2$ (200 ml) then ether (200 ml) and dried under suction then in

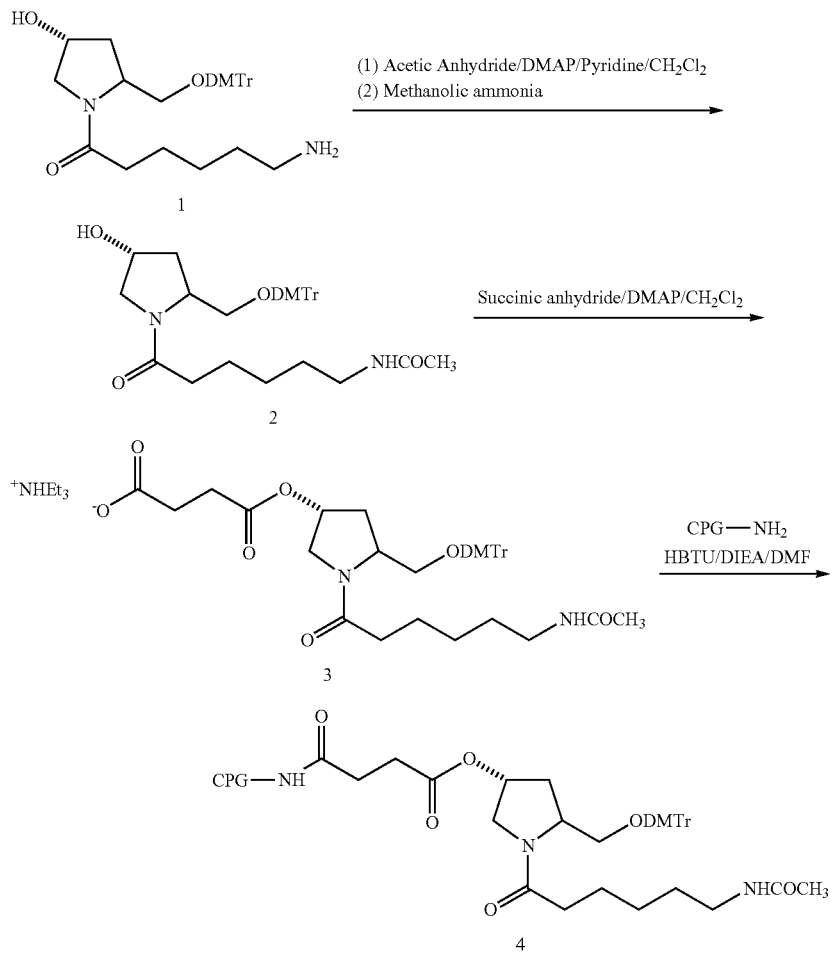

Scheme 1 vacuo. The residual amino groups were capped by shaking for 30 min with Pyridine/Ac₂O/Triethylamine (80:20:2, 100 ml). Filtration and washing with CH₂Cl₂ (100 ml), 10% MeOH/CH₂Cl₂ (200 ml) then ether (200 ml) and drying overnight in vacuo gave CPG compound 4. Loading: 52.8 µmol/g.

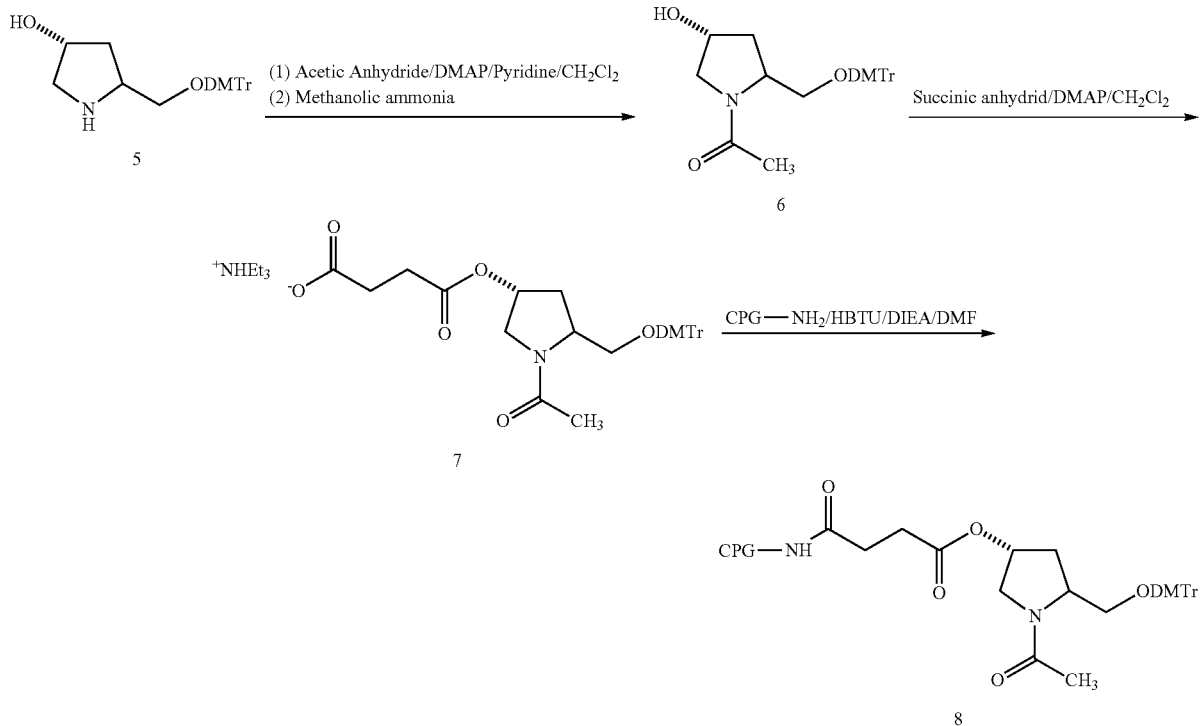

Scheme 2

Preparation of Compound 6: 4-Hydroxy-L-prolinol-2-hydroxymethyl-O-DMTr-amine 5 (lot # H2250-12C, 2 g, 4.80 mmol), DMAP (117.3 mg, 0.96 mmol), acetic anhydride (545 µl, 5.7 mmol) and pyridine (2 ml) were stirred in CH₂Cl₂ (40 ml) for 1.5 h at room temperature. Then 75 ml of methanolic ammonia solution added to it and stirred for overnight at room temperature. TLC showed complete reaction. Compound 6 (1.81 g, 3.73 mmol) was isolated after aqueous work up and column chromatography.

Yield: 1.81 g, 77.9%. Electrospray MS (+ve) for $C_{28}H_{31}NNaO_5$ $(M+Na)^+$ calcd. 484.54, found 484.20.

Preparation of Compound 7: Compound 6 (950 mg, 2.00 mmol) in CH₂Cl₂ (40 ml) was treated with DMAP (856 mg, 7.00 mmol) and succinic anhydride (600 mg, 6.00 mmol) then stirred for overnight at room temperature. After aqueous work up, the product 7 obtained as a quantitative yield. Electrospray MS (+ve) for $C_{32}H_{34}NNaO_8$ $(M+Na)^+$ calcd. 583.60, found 584.20.

Preparation of CPG 8: Compound 7 (1.36 g, 2.32 mmol) in DMF (100 ml), HBTU (987 mg, 2.60 mmol), DIEA (1.40 ml, 8.0 mmol) then CPG-NH₂ (140 µmol/g, 15.7 g, 2.2 mmol) were added in succession. The mixture was shaken for 4 h at r.t. then the solid was collected by filtration, washed with CH₂Cl₂ (100 ml), 10% MeOH/CH₂Cl₂ (200 ml) then ether (250 ml) and dried under suction then in vacuo. The residual amino groups were capped by shaking for 40 min with Pyridine/Ac₂O/Triethylamine (80:20:2, 100 ml). Filtration and washing with CH₂Cl₂ (100 ml), 10% MeOH/CH₂Cl₂ (200 ml) then ether (200 ml) and drying overnight in vacuo gave CPG compound 8. Loading: 74 µmol/g.

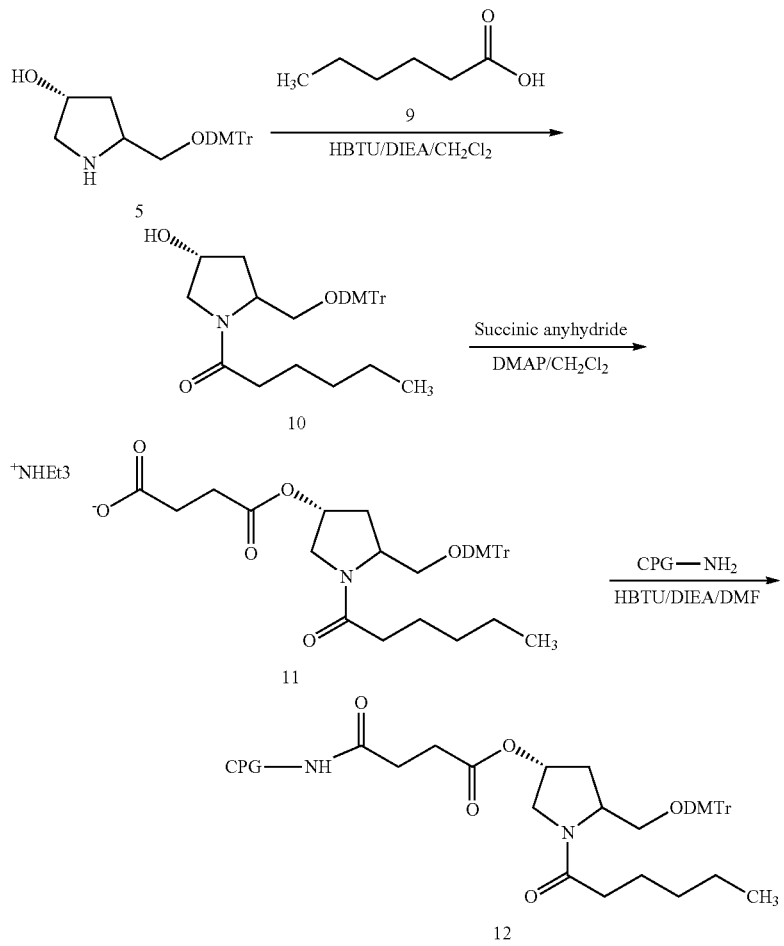

Scheme 3

Preparation of Compound 10: 4-Hydroxy-L-prolinol-2-hydroxymethyl-O-DMTr-amine 5 (lot # H2250-12C, 3 g, 7.15 mmol) was added to a stirred solution of hexanoic acid 9 (990 μl, 7.90 mmol), HBTU (3.50 g, 9.30 mmol) and DIEA (5.60 ml, 32.20 mmol) in $CH_2Cl_2$ (100 ml) for 2 h at room temperature. TLC showed complete reaction. Compound 10 (3.7 g, 6.84 mmol) was isolated after aqueous work up and column chromatography. Yield: 3.7 g, 95.8%. Electrospray MS (+ve) for $C_{32}H_{39}NNaO_5$ (M+Na)$^+$ calcd. 540.65, found 540.30.

Preparation of Compound 11: Compound 10 (3.50 g, 6.47 mmol) in $CH_2Cl_2$ (100 ml) was treated with DMAP (2.92 g, 23.94 mmol) and succinic anhydride (2.1 g, 20.54 mmol) then stirred for overnight at room temperature. TLC showed that the reaction was completed. After aqueous work up, the product 11 obtained as a quantitative yield. Electrospray MS (+ve) for $C_{36}H_{42}NNaO_8$ (M+Na) calcd. 639.71, found 640.30.

Preparation of CPG 12: Compound 11 (1.6 g, 2.50 mmol) in DMF (100 ml), HBTU (2.9 g, 7.64 mmol), DIEA (1.60 ml, 9.18 mmol) then CPG-NH$_2$ (lot # PSI.002.859, 147 mol/g, 15.1 g, 2.21 mmol) were added in succession. The mixture was shaken for 3 h at r.t. then the solid was collected by filtration, washed with $CH_2Cl_2$ (100 ml), 10% MeOH/$CH_2Cl_2$ (200 ml) then ether (250 ml) and dried under suction then in vacuo. The residual amino groups were capped by shaking for 40 min with Pyridine/Ac$_2$O/Triethylamine (80:20:2, 100 ml). Filtration and washing with $CH_2Cl_2$ (100 ml), 10% MeOH/$CH_2Cl_2$ (200 ml) then ether (200 ml) and drying overnight in vacuo gave CPG compound 12. Loading: 86 μmol/g.

Scheme 4
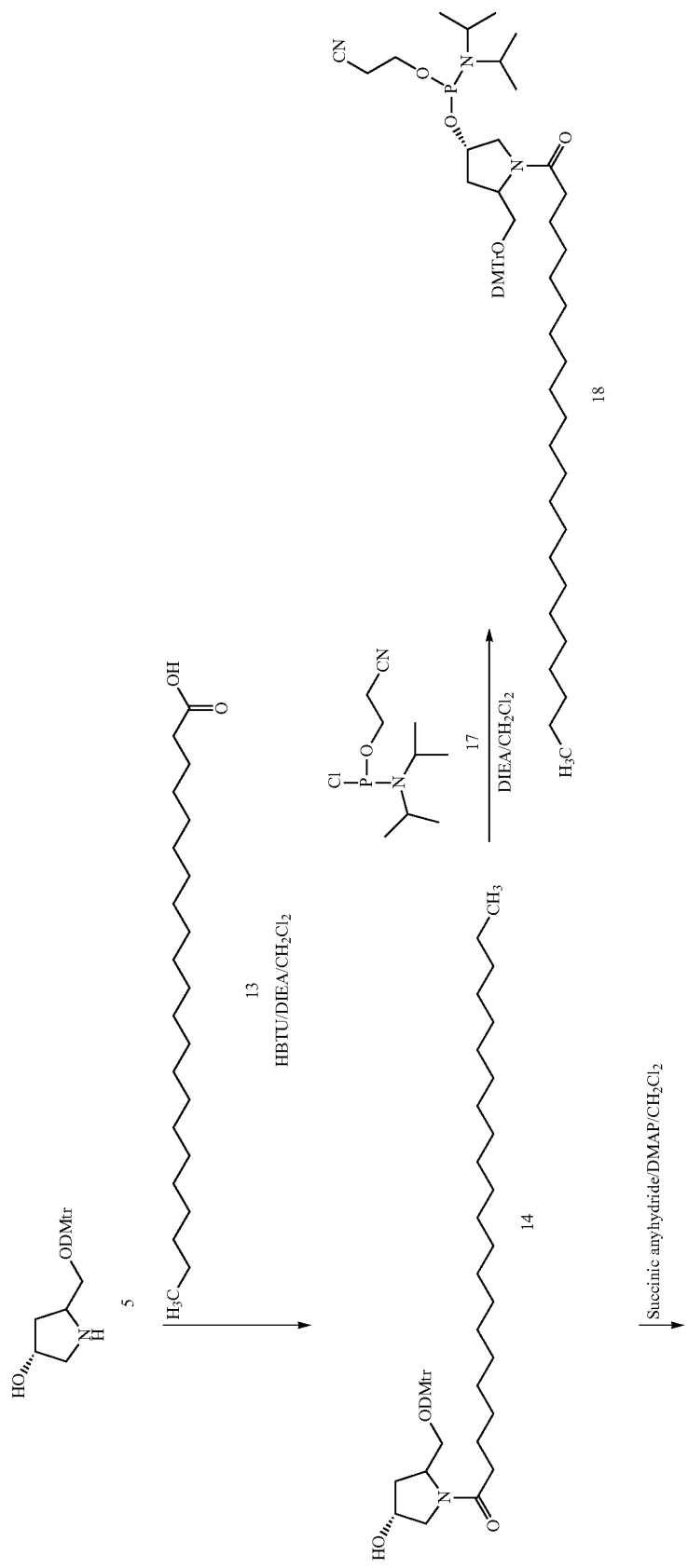

-continued
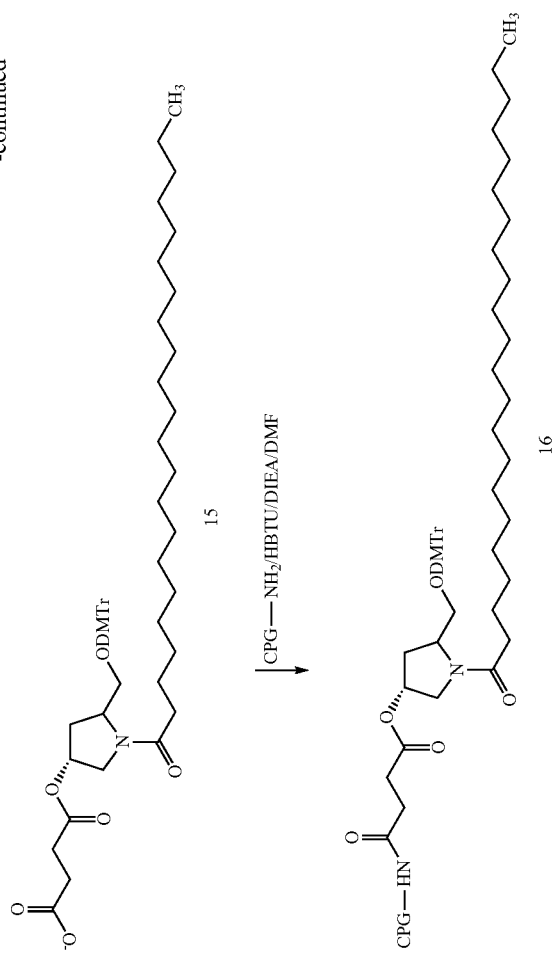

Preparation of Compound 14: 4-Hydroxy-L-prolinol-2-hydroxymethyl-O-DMTr-amine 5 (lot # H2250-12C, 10 g, 23.83 mmol) was added to a stirred solution of docosanoic acid 13 (8.93 g, 26.22 mmol), HBTU (15.40 g, 40.51 mmol) and DIEA (18.70 ml, 107.23 mmol) in $CH_2Cl_2$ (300 ml) for overnight at room temperature. TLC showed that the reaction was completed. Compound 14 (10.51 g pure, 7 g crude) was isolated after aqueous work up and column chromatography. Yield: 10.51 g pure, 7 g crude. Electrospray MS (+ve) for $C_{48}H_{71}NNaO_5$ (M+Na)$^+$ calcd. 765.07, found 764.50.

Preparation of Compound 15: Compound 14 (3.48 g, 4.54 mmol) in $CH_2Cl_2$ (100 ml) was treated with DMAP (1.94 g, 15.89 mmol) and succinic anhydride (1.36 g, 13.63 mmol) then stirred for 2.5 h at room temperature. TLC showed that the reaction was completed. After aqueous work up, the product 15 obtained as a quantitative yield. Electrospray MS (+ve) for $C_{52}H_{74}NNaO_8$ (M+Na) calcd. 863.53, found 862.50.

Preparation of CPG 16: Compound 15 (3.4 g, 3.93 mmol) in DMF (100 ml), HBTU (2.0 g, 5.2 mmol), DIEA (2.10 ml, 12.0 mmol) then CPG-NH$_2$ (lot # PSI.002.859, 147 µmol/g, 21 g, 3.087 mmol) were added in succession. The mixture was shaken for 3.75 h at r.t. then the solid was collected by filtration, washed with $CH_2Cl_2$ (100 ml), 10% MeOH/$CH_2Cl_2$ (200 ml) then ether (250 ml) and dried under suction then in vacuo. The residual amino groups were capped by shaking for 35 min with Pyridine/Ac$_2$O/Triethylamine (80:20:2, 100 ml). Filtration and washing with $CH_2Cl_2$ (100 ml), 10% MeOH/$CH_2Cl_2$ (200 ml) then ether (200 ml) and drying overnight in vacuo gave CPG compound 16. Loading: 81.4 µmol/g.

Preparation of 18: Amidite reagent 17 (2.71 ml, 12.16 mmol) was added to a stirred solution of compound 14 (6.2 g, 8.10 mmol) in $CH_2Cl_2$ (60 ml) and DIEA (5.64 ml, 32.40 mmol) in an ice bath. The reaction mixture was allowed to stir for 30 min at 0° C. to r.t. under argon. TLC showed that the reaction was completed. Compound 18 (3.37 g, 3.49 mmol) was isolated after aqueous work up and column chromatography. Yield: 3.37 g, 43%. Electrospray MS (+ve) for $C_{57}H_{88}N_3NaO_6P$ (M+Na)$^+$ calcd. 965.29, found 965.50.

Preparation of compound 20: 4-Hydroxy-L-prolinol-2-hydroxymethyl-O-DMTr-amine 5 (lot # H2250-12C, 6 g, 14.30 mmol) was added to a stirred solution of azido-dPEG4-acid 19 (4.6 g, 15.73 mmol), HBTU (9.22 g, 24.31 mmol) and DIEA (11.2 ml, 64.35 mmol) in $CH_2Cl_2$ (150 ml) for overnight at room temperature. TLC showed that the reaction was completed. Compound 20 (9.47 g, 13.23 mmol) was isolated after aqueous work up and column chromatography. Yield: 9.47 g, 92.5%. Electrospray MS (+ve) for $C_{37}H_{48}N_4NaO_9$ (M+Na)$^+$ calcd. 715.79, found 715.30.

Preparation of Compound 21: Compound 20 (19.9 g, 28.7 mmol) and PPh3 (22.6 g, 86.2 mmol) in THF/H$_2$O (10:1, 500 ml) was stirred for 20 h at room temperature. TLC showed a complete reaction. Column chromatography gave pure compound 21. Yield: 15.7 g, 82%. $^1$H NMR (DMSO-d$_6$, 400 MHz) δ=7.30 (m, 4H), 7.19 (m, 5H), 6.86 (m, 4H), 5.2-4.75 (br, 1H), 4.39-4.26 (m, 1H), 4.13 (m, 1H), 3.72 (s, 6H), 3.62-3.54 (m, 2H), 3.51-3.24 (m, 16H), 3.13-2.99 (m, 2H), 2.62 (t, J=5.8 Hz, 2H), 2.50-2.40 (m, 2H), 2.24-1.78 (m, 2H), 1.8-1.4 (br, 2H). Electrospray MS (+ve) for $C_{37}H_{50}N_2NaO_9$ (M+Na)$^+$ calcd. 689.3, found 689.2.

Preparation of Compound 23: Compound 21 (10.6 g, 15.37 mmol) in THF (100 ml), triethylamine (8.6 ml, 61.48 mmol) and N-carbethoxy-phthalimide (5.05 g, 23.06 mmol) were stirred for overnight at r.t. Compound 23 (8.2 g, 10.00 mmol) was isolated after aqueous work up and column chromatography. Yield: 8.2 g, 65%. Electrospray MS (+ve) for $C_{45}H_{52}N_2NaO_{11}$ (M+Na)$^+$ calcd. 819.35, found 819.20.

Preparation of Compound 24: Compound 23 (3.1 g, 3.78 mmol) in $CH_2Cl_2$ (100 ml) was treated with DMAP (1.48 g, 12.13 mmol) and succinic anhydride (1.04 g, 10.4 mmol) then stirred for overnight at room temperature. TLC showed that the reaction was completed. After aqueous work up, the product 24 obtained as a quantitative yield. Electrospray MS (+ve) for $C_{49}H_{55}N_2NaO_{14}$ (M+Na)$^+$ calcd. 918.96, found 919.2.

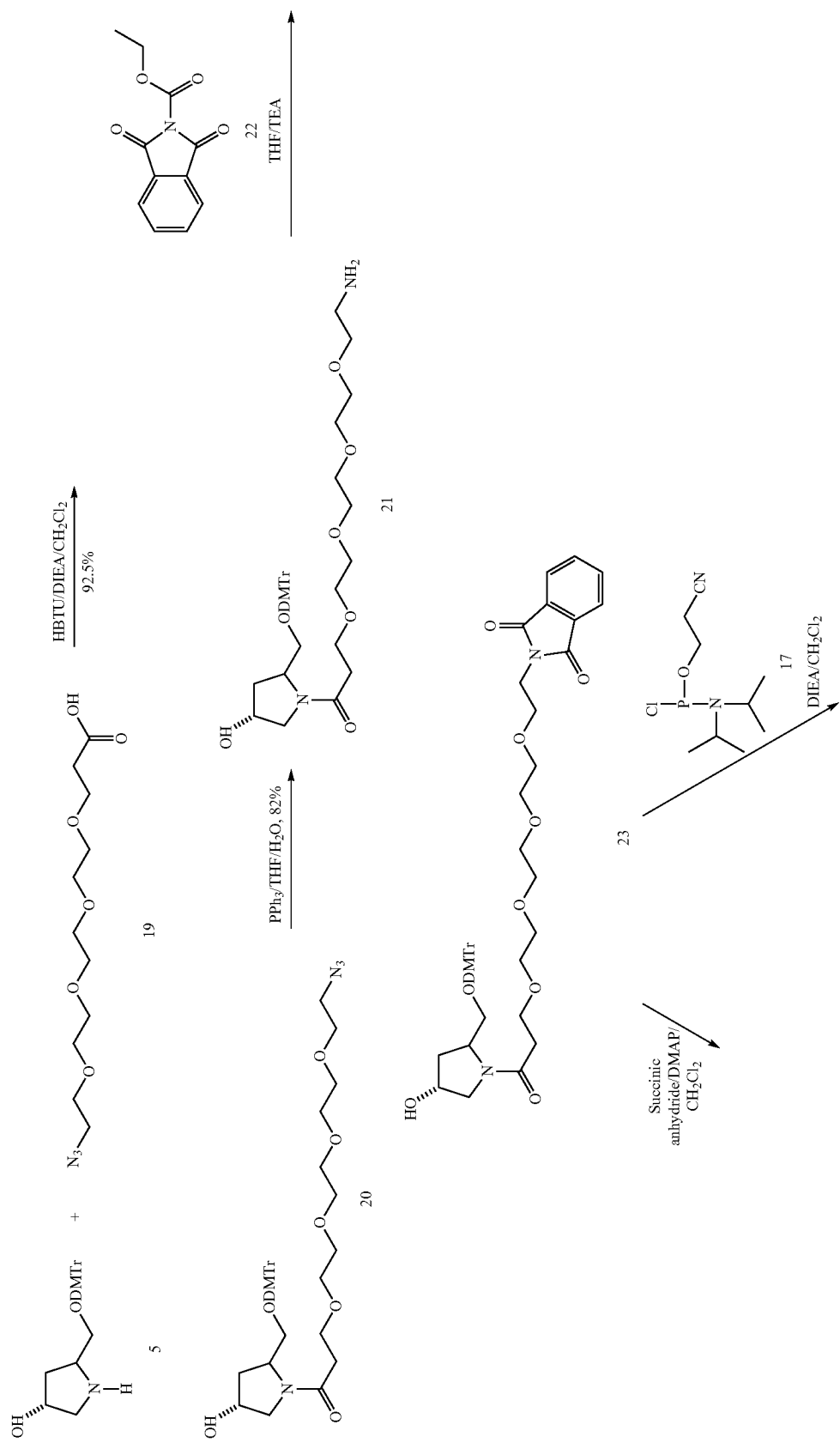

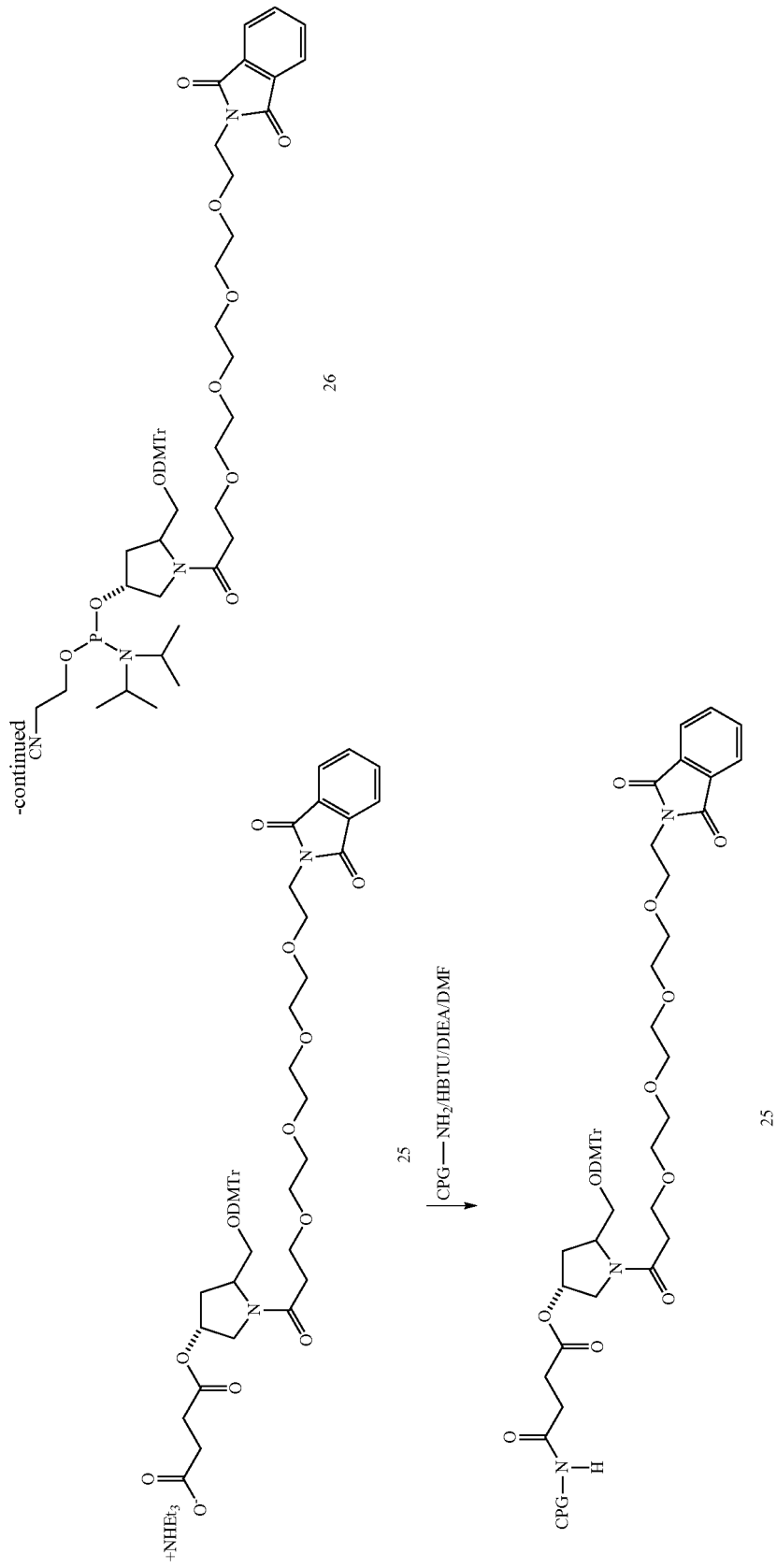

Preparation of CPG 25: Compound 24 (3.88 g, 4.22 mmol) in DMF (100 ml), HBTU (1.8 g, 4.76 mmol), DIEA (2 ml, 11.2 mmol) then CPG-NH$_2$ (lot # PSI.002.787, 140 µmol/g, 20 g, 2.8 mmol) were added in succession. The mixture was shaken for 3.5 h at r.t. then the solid was collected by filtration, washed with CH$_2$Cl$_2$ (100 ml), 10% MeOH/CH$_2$Cl$_2$ (200 ml) then ether (250 ml) and dried under suction then in vacuo. The residual amino groups were capped by shaking for 30 min with Pyridine/Ac$_2$O/Triethylamine (80:20:2, 100 ml). Filtration and washing with CH$_2$Cl$_2$ (100 ml), 10% MeOH/CH$_2$Cl$_2$ (200 ml) then ether (200 ml) and drying overnight in vacuo gave CPG compound 25. Loading: 83 µmol/g.

Preparation of 26: Amidite reagent 17 (2.0 ml, 9.15 mmol) was added to a stirred solution of compound 23 (5.0 g, 6.10 mmol) in CH$_2$Cl$_2$ (50 ml) and DIEA (4.2 ml, 24.4 mmol) in an ice bath. The reaction mixture was allowed to stir for 1 h at 0° C. to r.t. under argon. TLC showed that the reaction was completed. Compound 26 (3.78 g, 3.79 mmol) was isolated after aqueous work up and column chromatography. Yield: 3.78 g, 62%.

Scheme 6

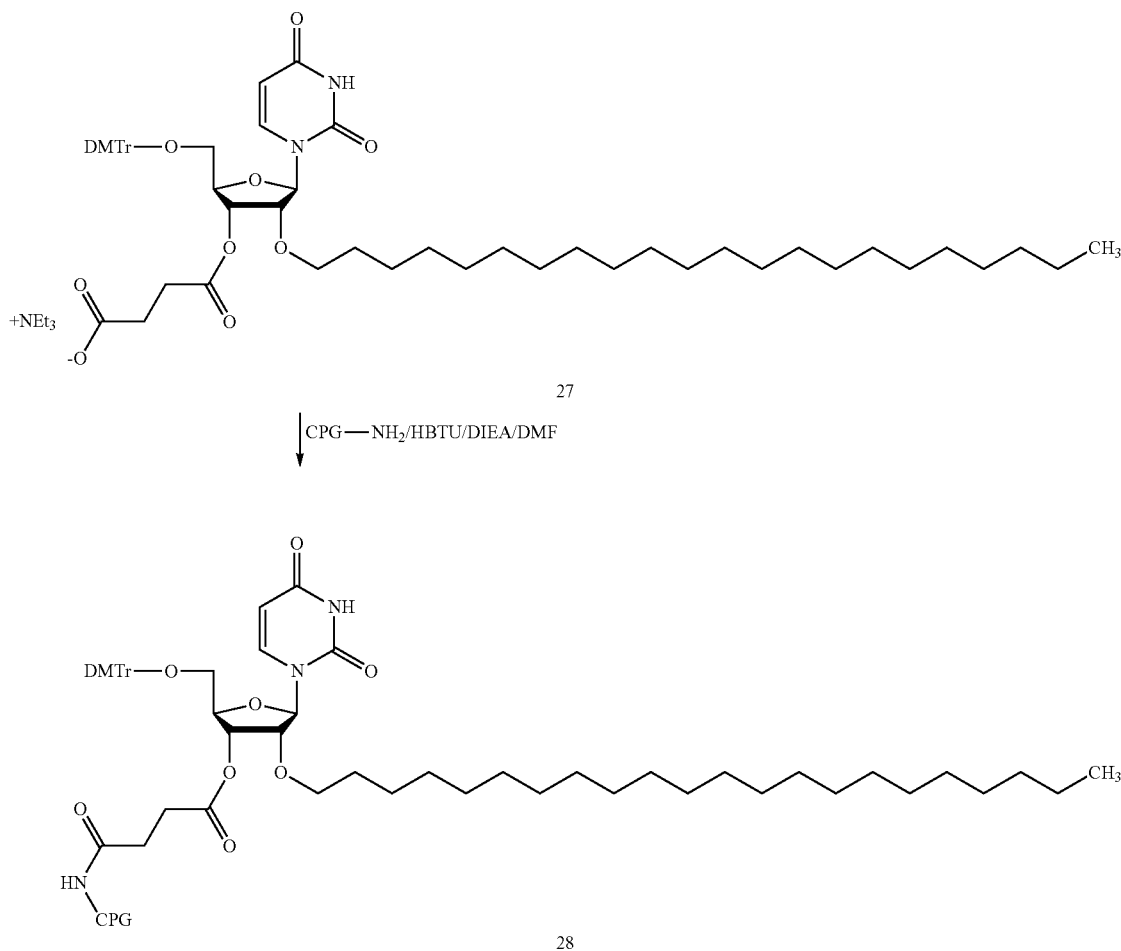

Preparation of CPG 28: 2'-Docosanyl-Uridine succinate compound 27 (3.3 g, 3.12 mmol)(obtained from NuBlocks LLC) in DMF (100 ml), HBTU (1.6 g, 4.21 mmol), DIEA (1.73 ml, 9.92 mmol) then CPG-NH$_2$ (lot # PSI.002.1167, 124 µmol/g, 20 g, 2.48 mmol) were added in succession. The mixture was shaken for 5 h at r.t. then the solid was collected by filtration, washed with CH$_2$Cl$_2$ (100 ml), 10% MeOH/CH$_2$Cl$_2$ (200 ml) then ether (250 ml) and dried under suction then in vacuo. The residual amino groups were capped by shaking for 35 min with Pyridine/Ac$_2$O/Triethylamine (80:20:2, 100 ml). Filtration and washing with CH$_2$Cl$_2$ (100 ml), 10% MeOH/CH$_2$Cl$_2$ (200 ml) then ether (200 ml) and drying overnight in vacuo gave CPG compound 28. Loading: 67.6 µmol/g.

Scheme 7

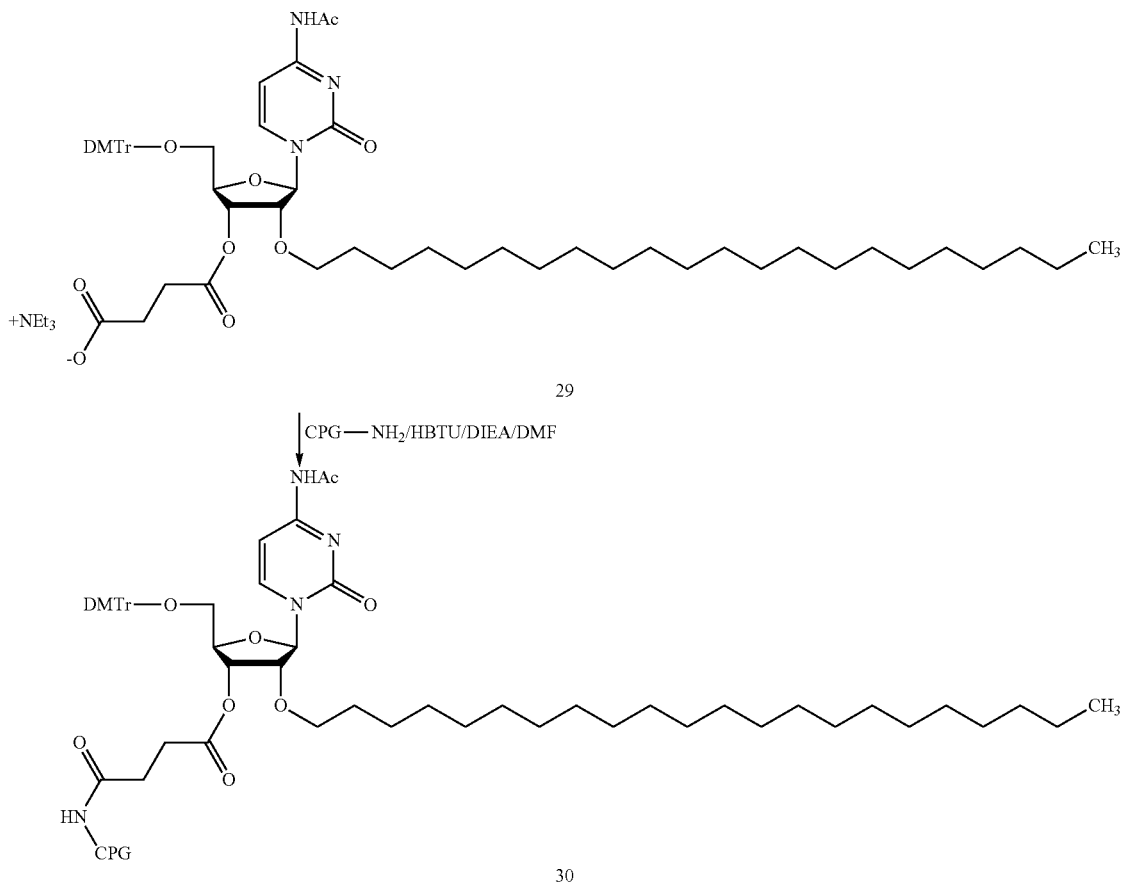

Preparation of CPG 30: 2'-Docosanyl-cytidine succinate compound 29 (3.53 g, 3.22 mmol)(obtained from NuBlocks LLC) in DMF (100 ml), HBTU (1.6 g, 4.21 mmol), DIEA (1.73 ml, 9.92 mmol) then CPG-NH$_2$ (lot # PSI.002.1167, 124 µmol/g, 20 g, 2.48 mmol) were added in succession. The mixture was shaken for 5 h at r.t. then the solid was collected by filtration, washed with CH$_2$Cl$_2$ (100 ml), 10% MeOH/CH$_2$Cl$_2$ (200 ml) then ether (250 ml) and dried under suction then in vacuo. The residual amino groups were capped by shaking for 35 min with Pyridine/Ac$_2$O/Triethylamine (80:20:2, 100 ml). Filtration and washing with CH$_2$Cl$_2$ (100 ml), 10% MeOH/CH$_2$Cl$_2$ (200 ml) then ether (200 ml) and drying overnight in vacuo gave CPG compound 30. Loading: 69.5 µmol/g.

Scheme 8 2'-O-Alkyl Modifications

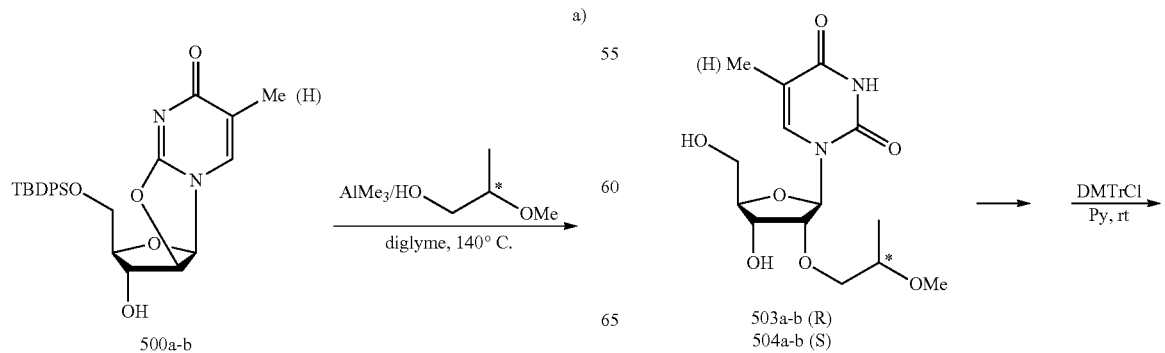

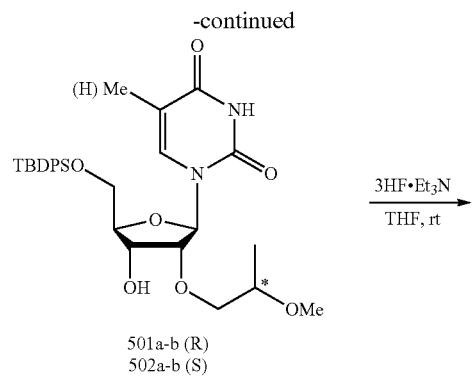

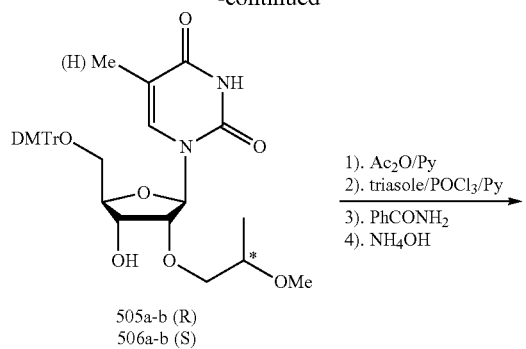
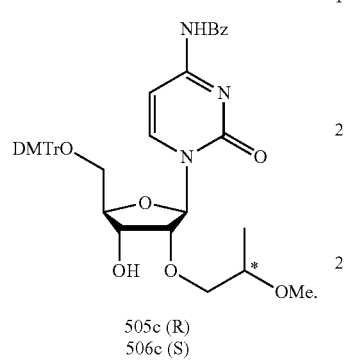
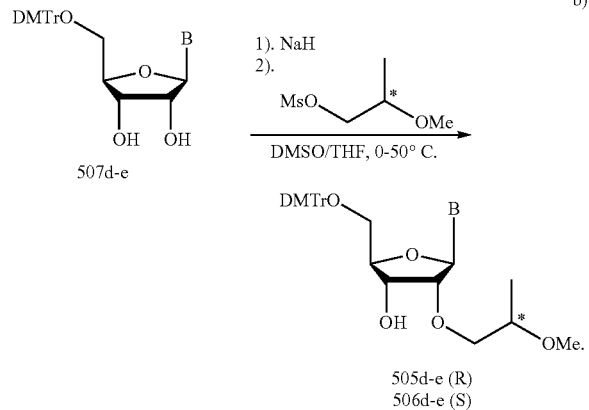
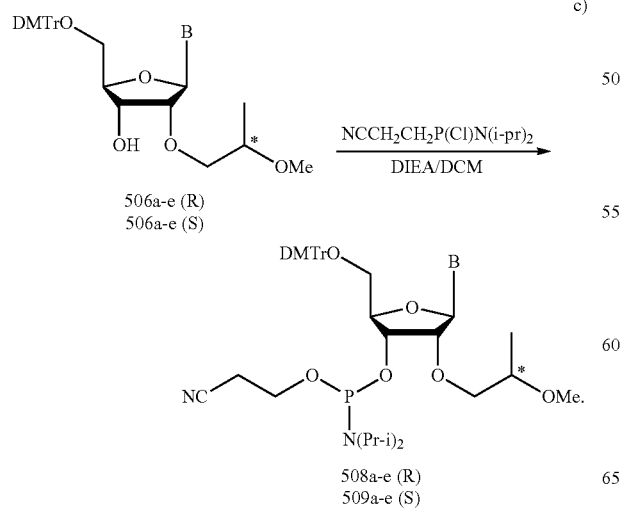
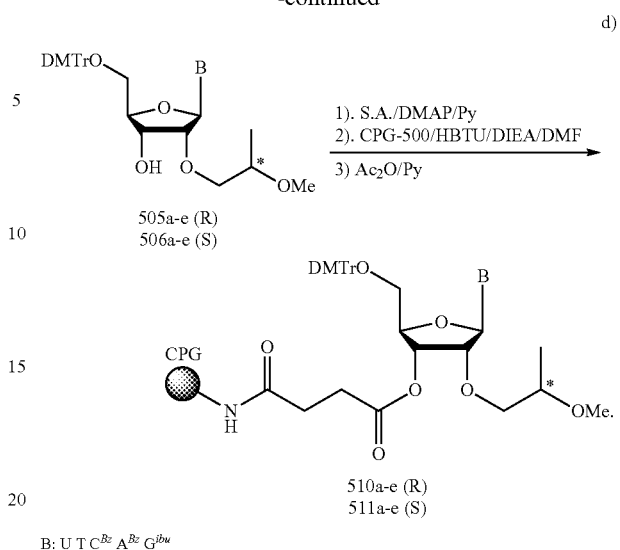
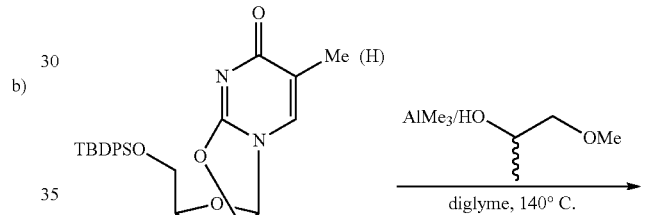
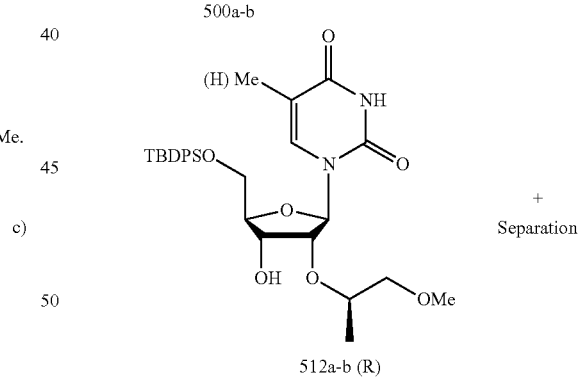
Scheme 9

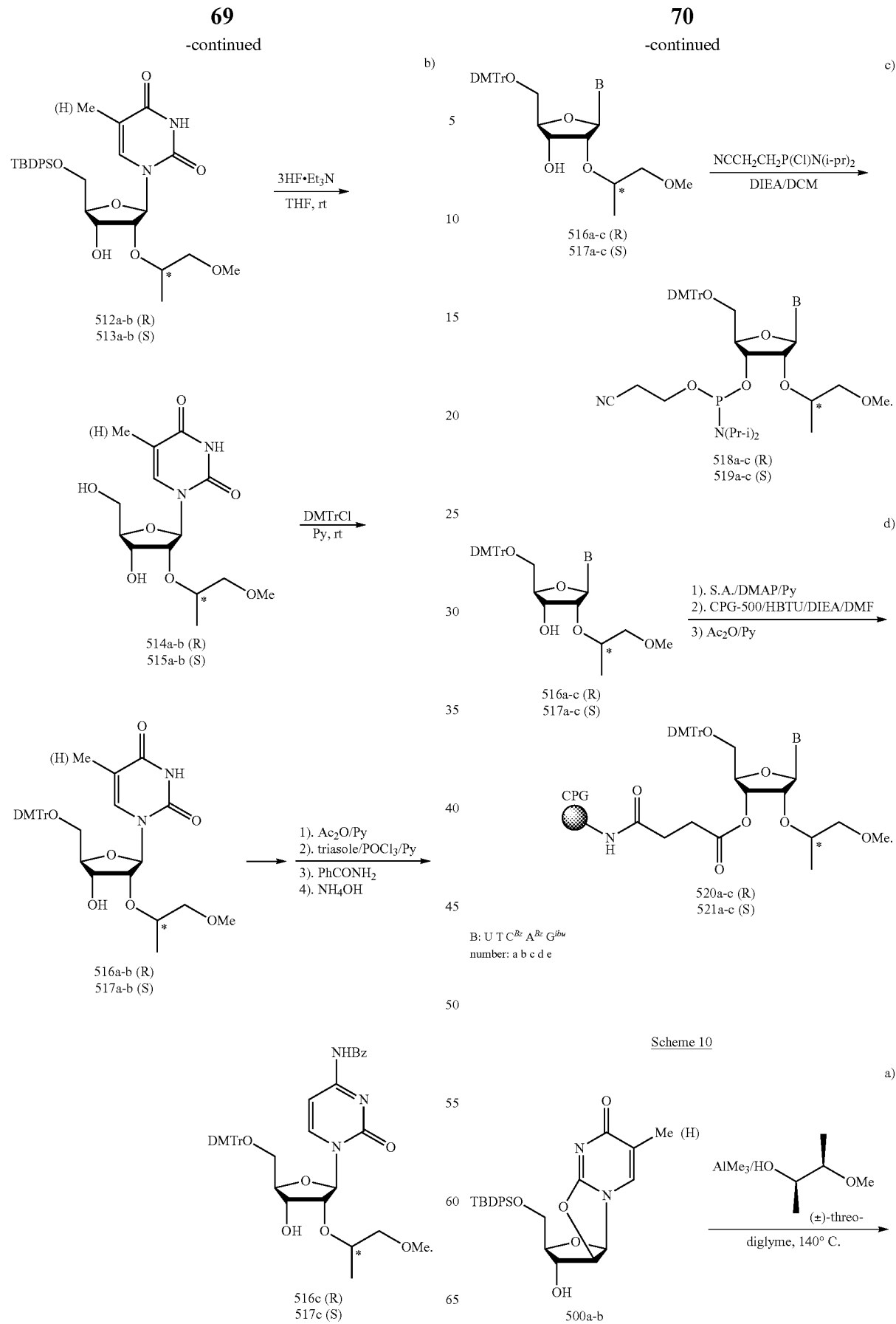

-continued

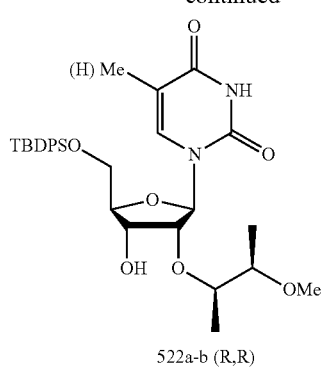

522a-b (R,R)

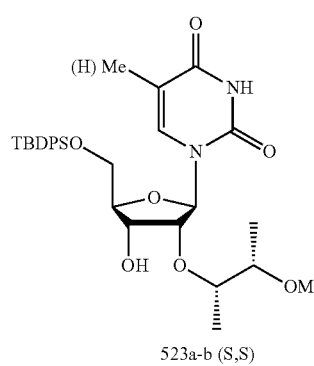

523a-b (S,S)

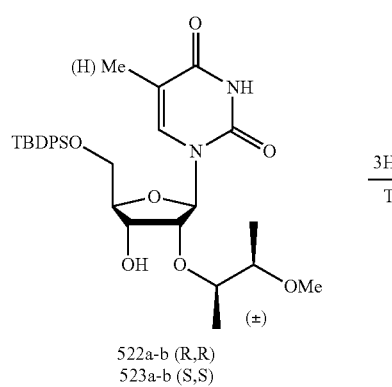

522a-b (R,R)
523a-b (S,S)

$\xrightarrow{\text{3HF·Et}_3\text{N}}{\text{THF, rt}}$

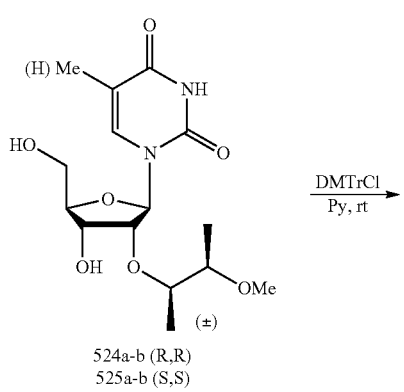

524a-b (R,R)
525a-b (S,S)

$\xrightarrow{\text{DMTrCl}}{\text{Py, rt}}$

+ Separation

-continued

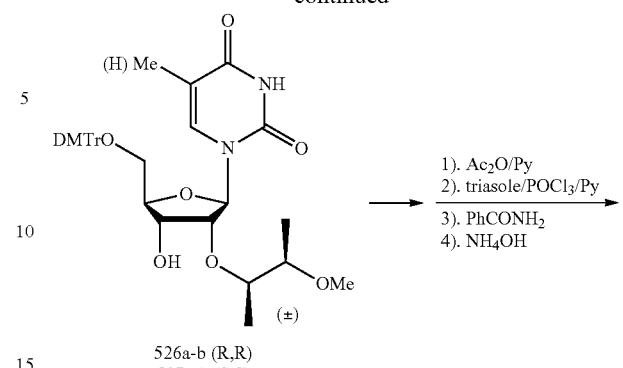

526a-b (R,R)
527a-b (S,S)

1). Ac$_2$O/Py
2). triasole/POCl$_3$/Py
3). PhCONH$_2$
4). NH$_4$OH
$\longrightarrow$

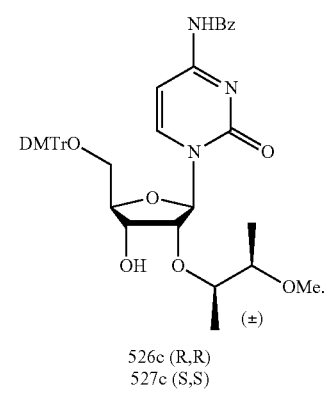

526c (R,R)
527c (S,S)

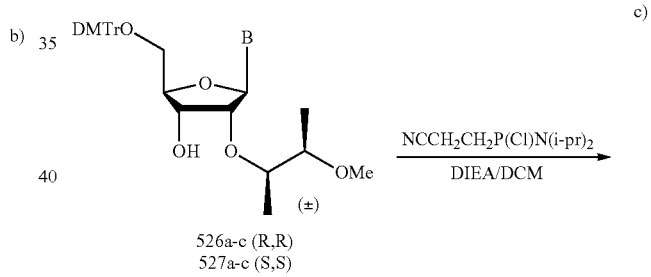

526a-c (R,R)
527a-c (S,S)

$\xrightarrow{\text{NCCH}_2\text{CH}_2\text{P(Cl)N(i-pr)}_2}{\text{DIEA/DCM}}$

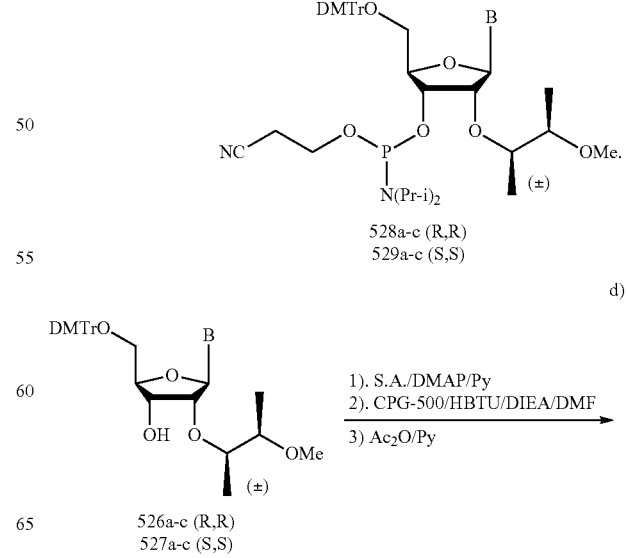

528a-c (R,R)
529a-c (S,S)

526a-c (R,R)
527a-c (S,S)

1). S.A./DMAP/Py
2). CPG-500/HBTU/DIEA/DMF
3) Ac$_2$O/Py
$\longrightarrow$

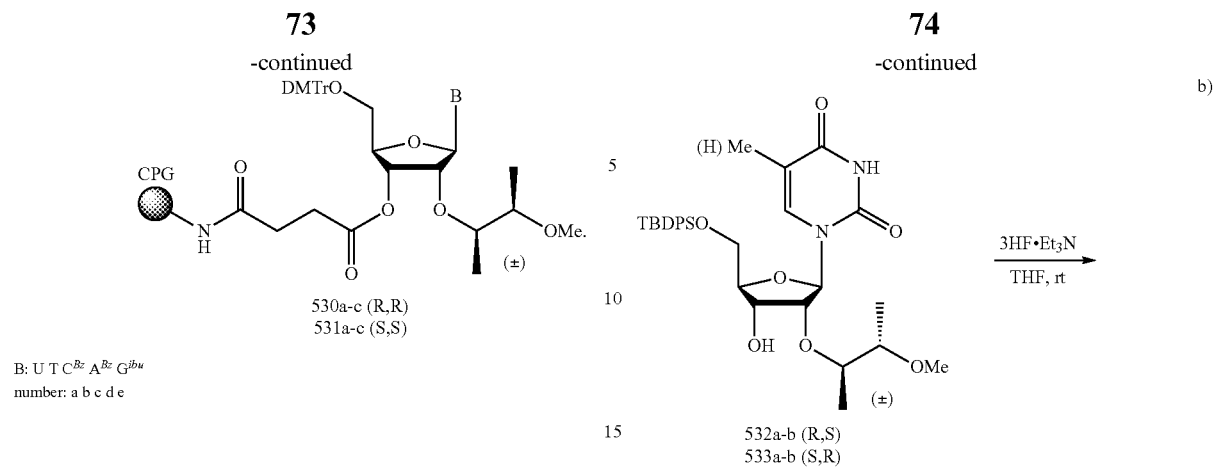
Scheme 11
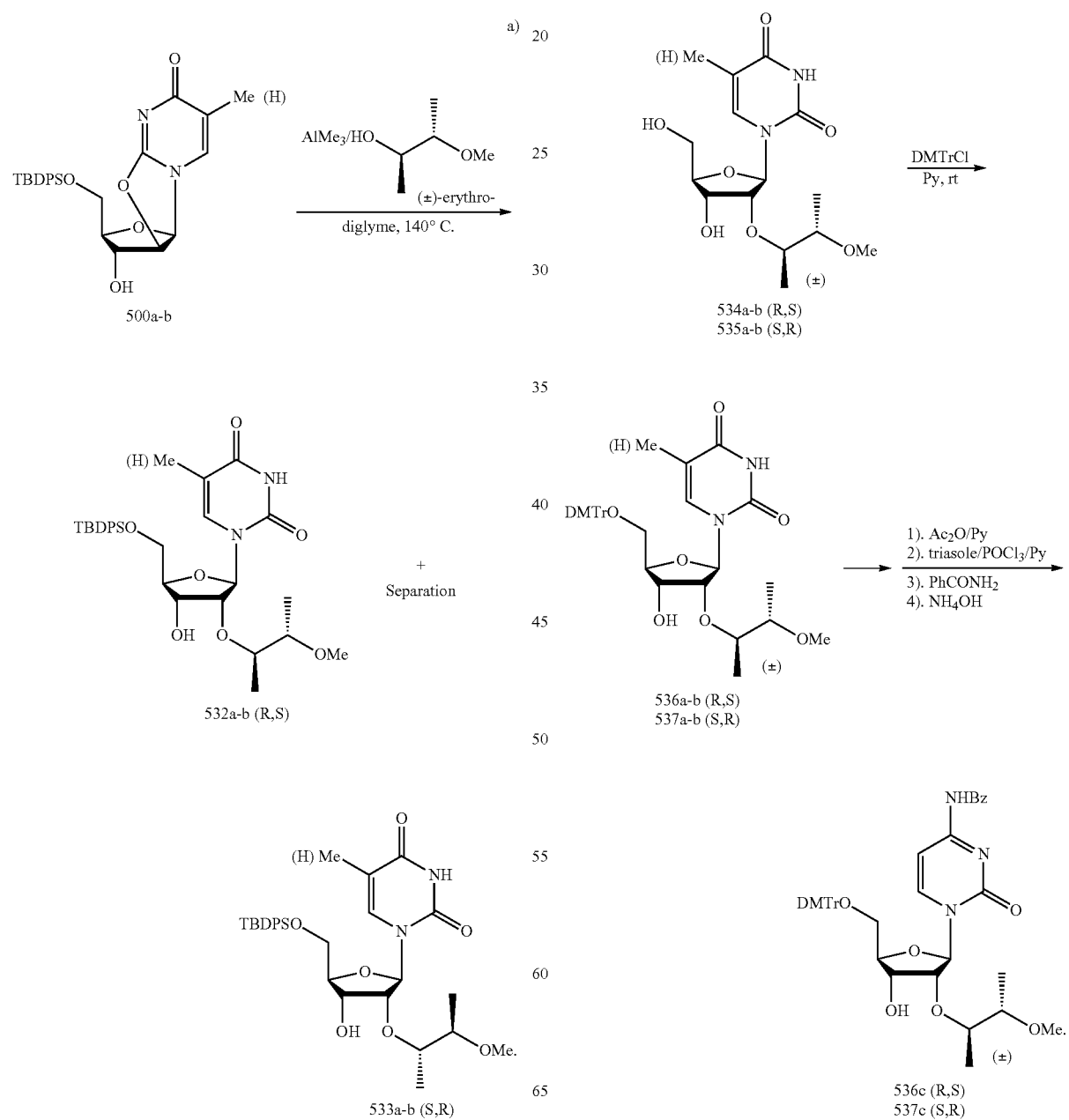

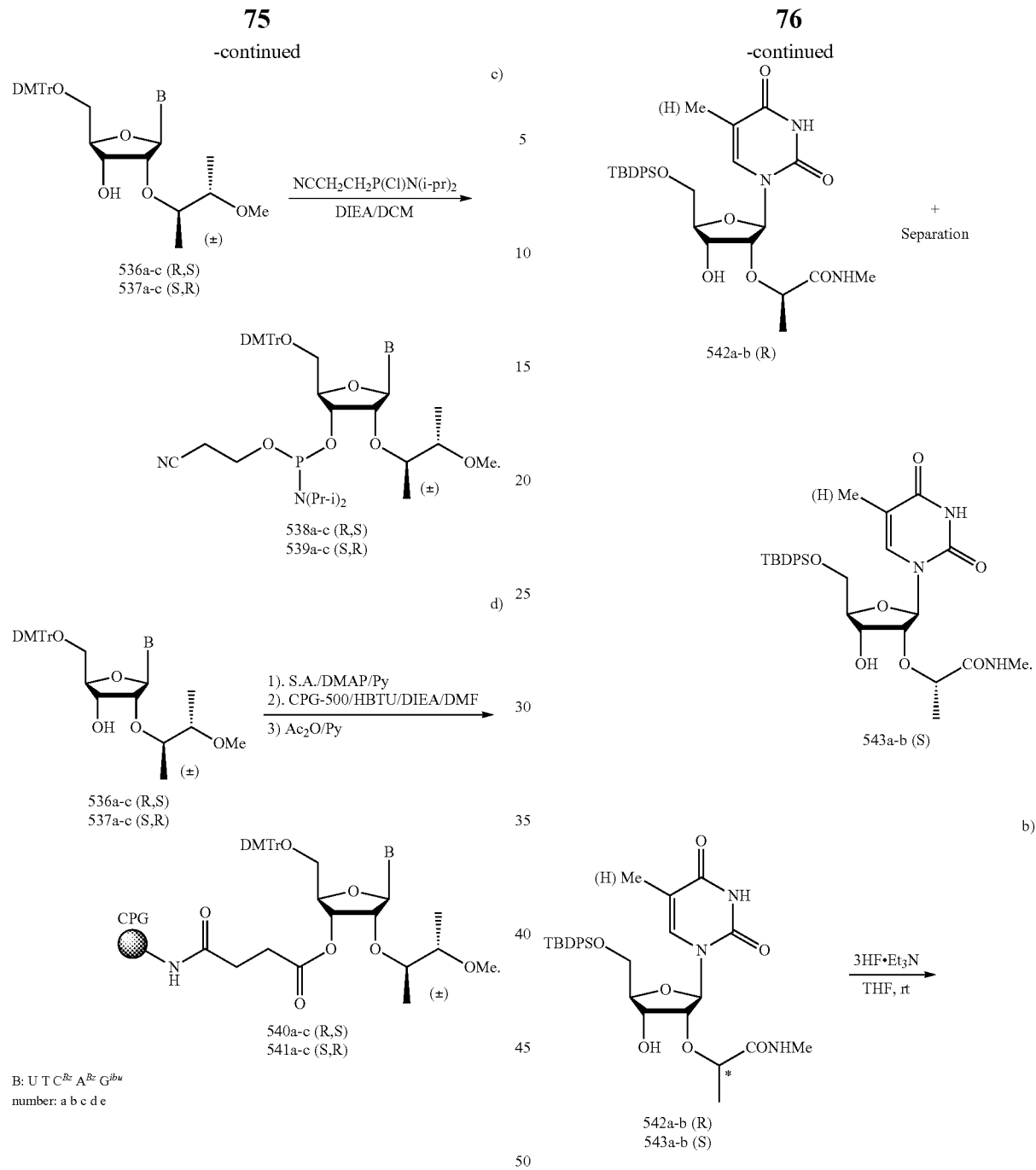
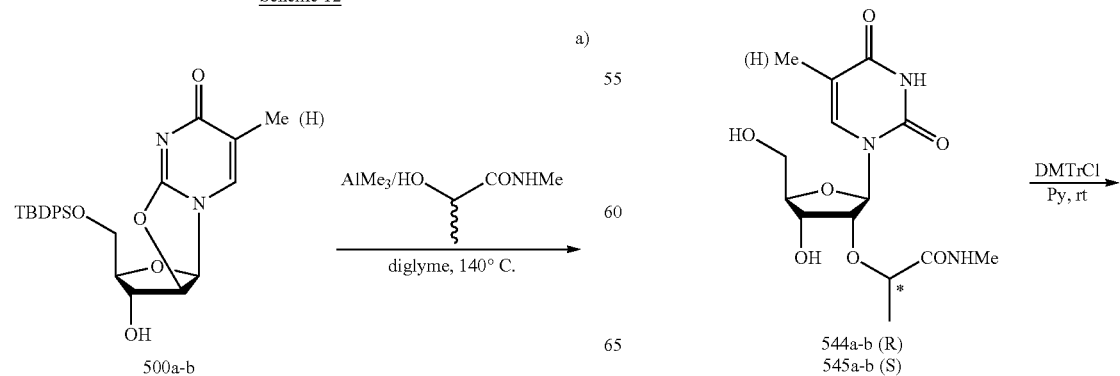

77
-continued
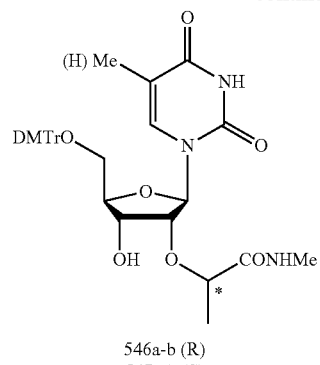
546a-b (R)
547a-b (S)
1). Ac₂O/Py
2). triasole/POCl₃/Py
3). PhCONH₂
4). NH₄OH
B: U T C$^{Bz}$ A$^{Bz}$ G$^{ibu}$
number: a b c d e
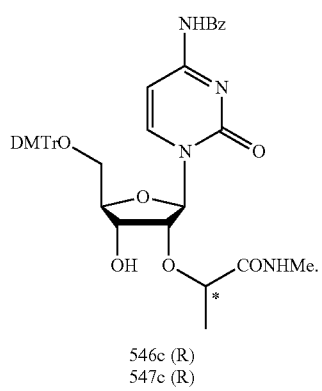
546c (R)
547c (R)
c)
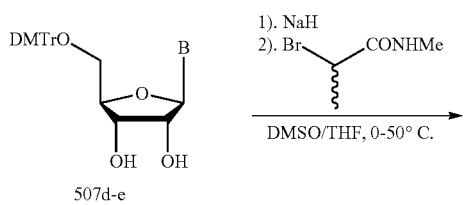
507d-e
1). NaH
2). Br–CH(CONHMe)
———————
DMSO/THF, 0–50° C.
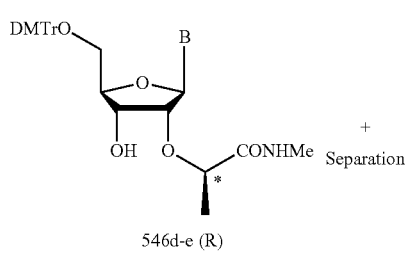
546d-e (R)
+ Separation
78
-continued
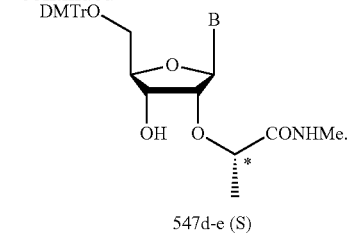
547d-e (S)
d)
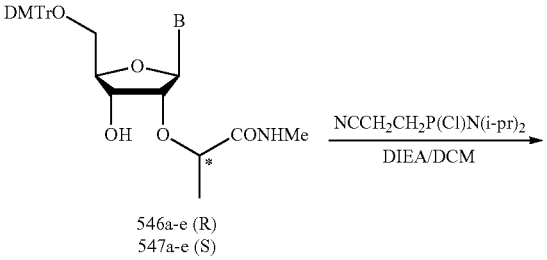
546a-e (R)
547a-e (S)
NCCH₂CH₂P(Cl)N(i-pr)₂
————————
DIEA/DCM
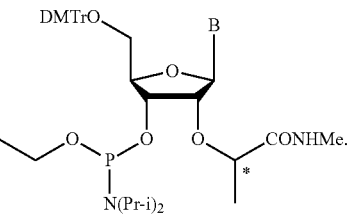
548a-e (R)
549a-e (S)
e)
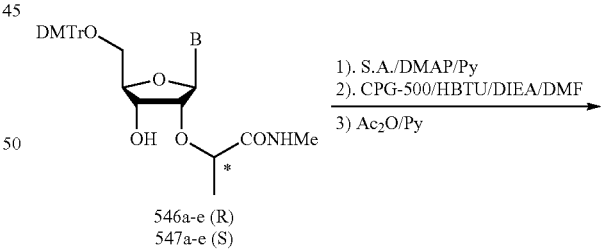
546a-e (R)
547a-e (S)
1). S.A./DMAP/Py
2). CPG-500/HBTU/DIEA/DMF
3) Ac₂O/Py
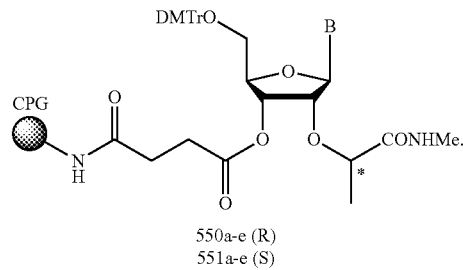
550a-e (R)
551a-e (S)

Scheme 13
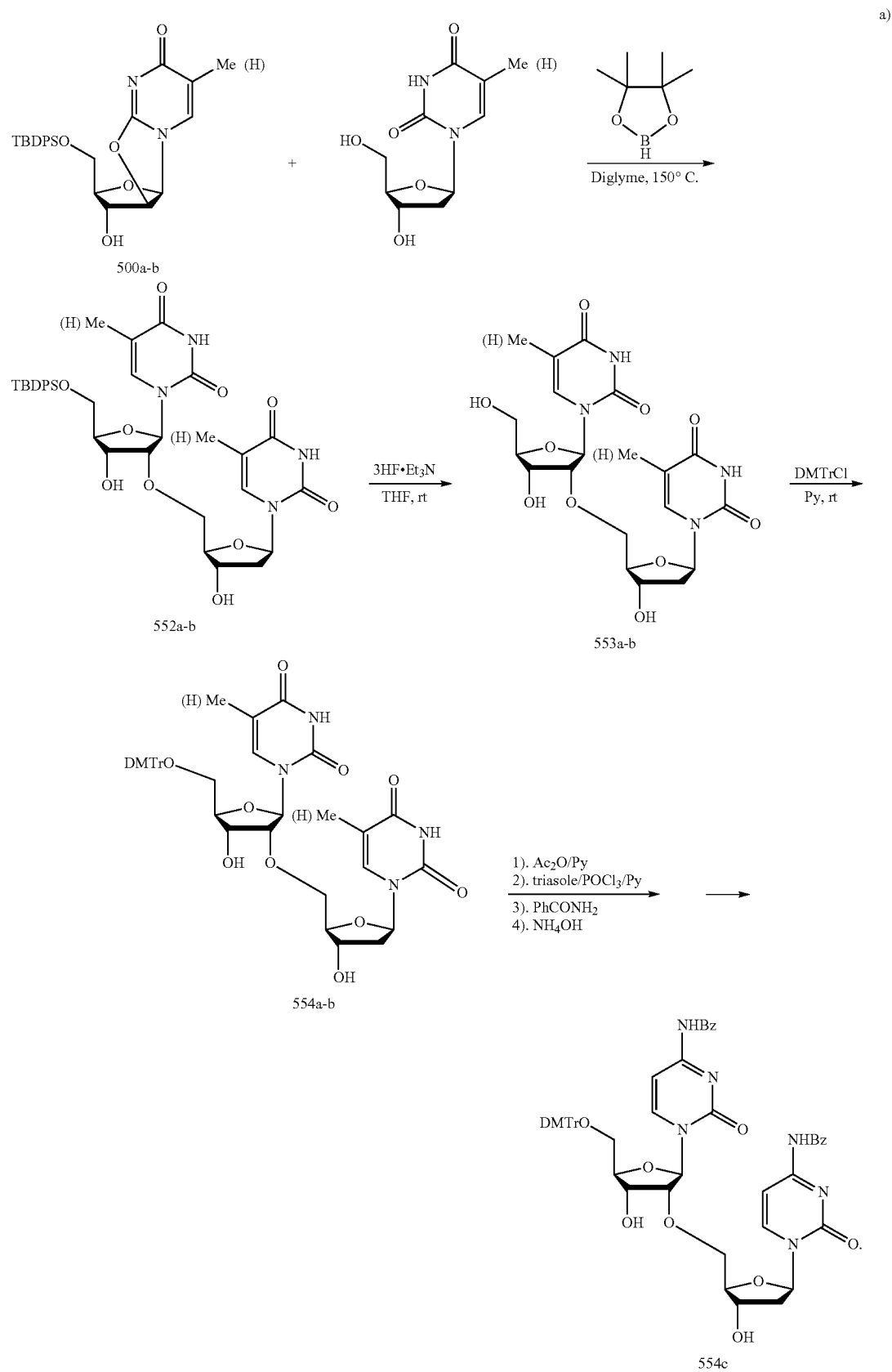

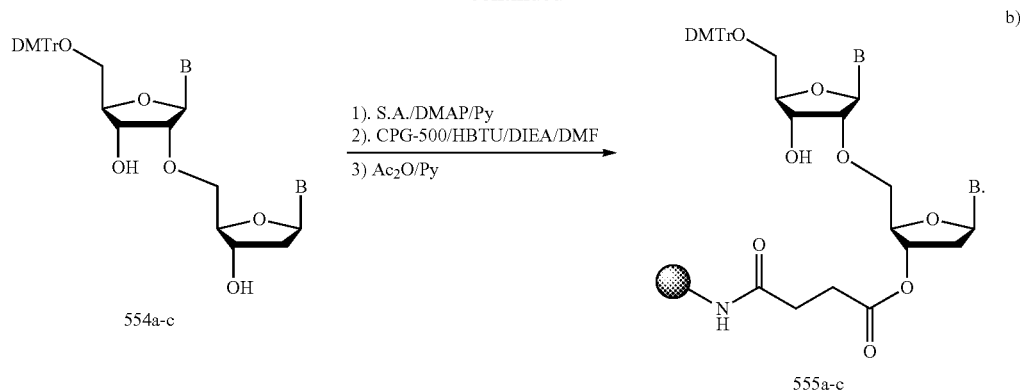
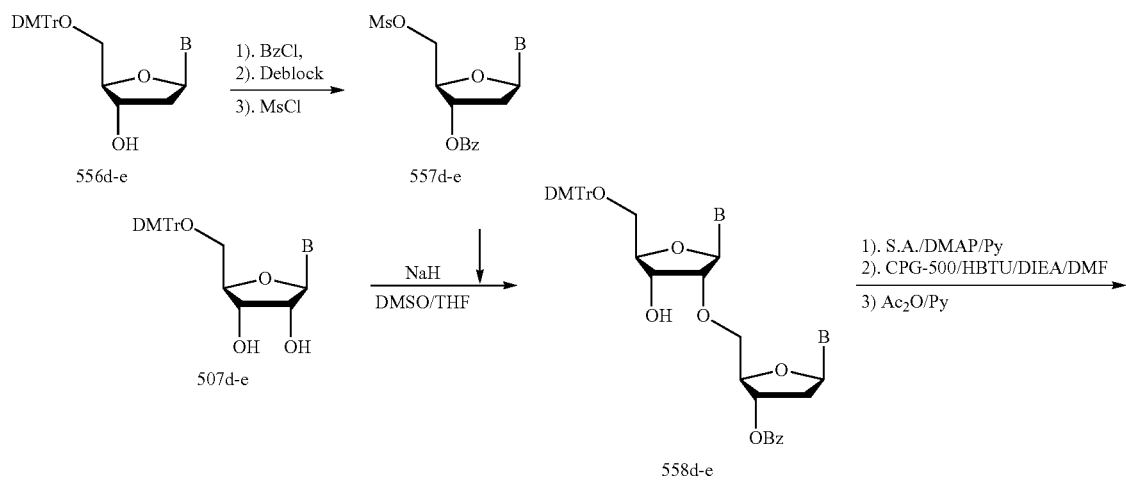
Scheme 14
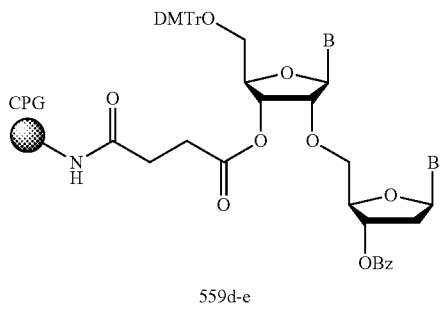
B: U T C$^{Bz}$ A$^{Bz}$ G$^{ibu}$
number: a b c d e

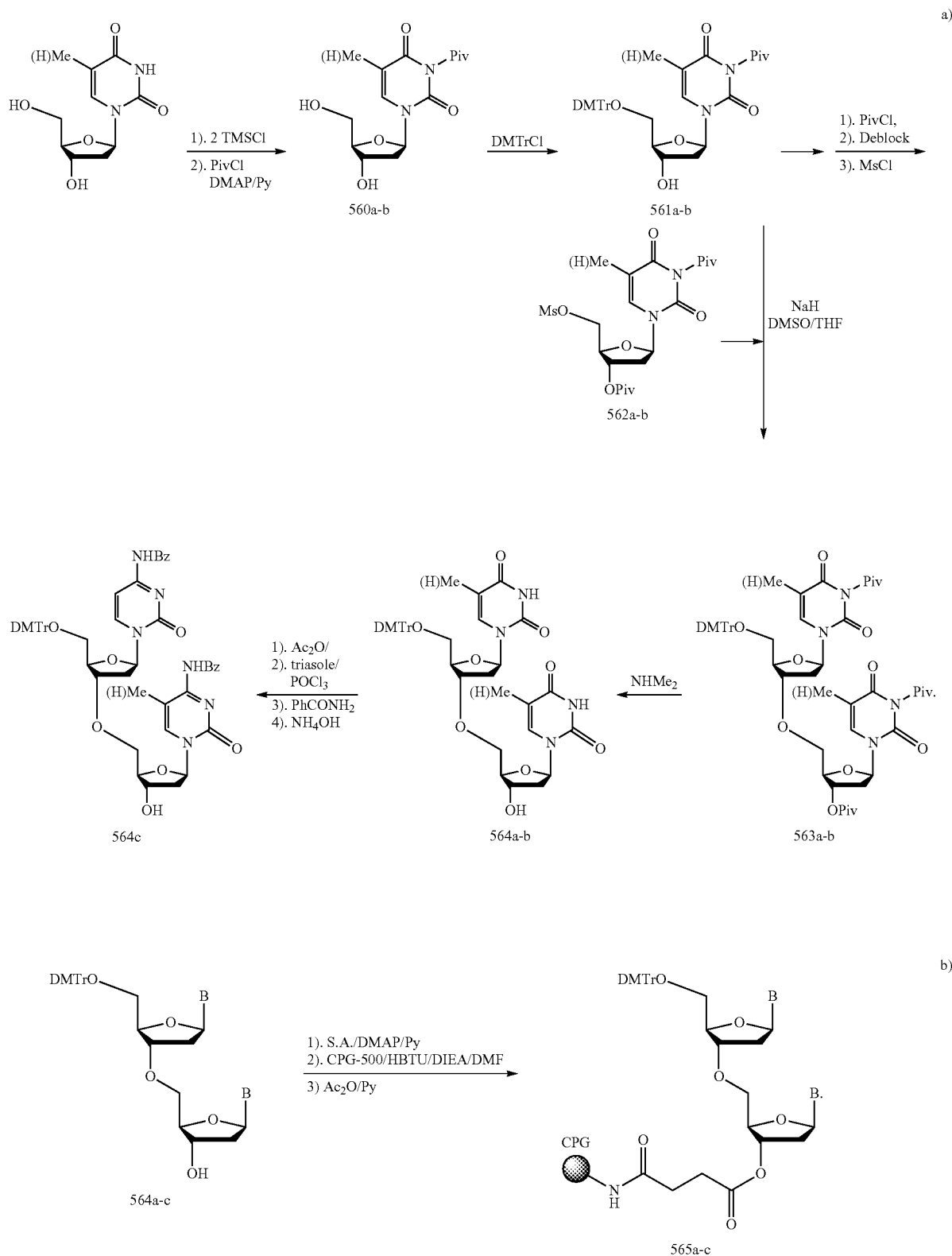

Scheme 16

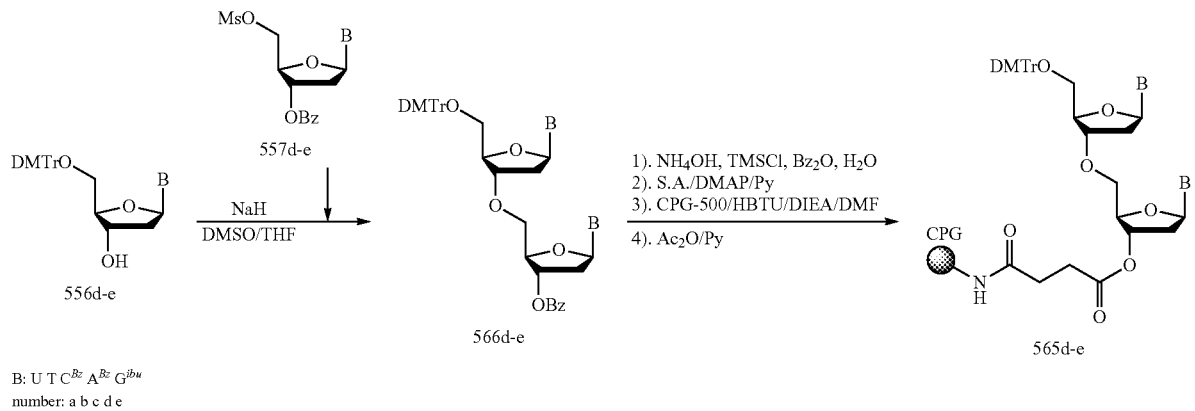

B: U T C$^{Bz}$ A$^{Bz}$ G$^{ibu}$
number: a b c d e

Compounds in Schemes 8-16:
1. Aluminum alkoxide-promoted ring opening of TBDPS-protected anhydro-nucleosides with primary alkohols.
Typical Procedure:

5'-TBDPS-protected 2'-((S)-2-methyl-2-methoxyethyloxy)-5-methyluridine (501b)

(S)-2-Methoxy-1-propanol (18.5 g, 0.206 mol) dried over 4 A molecular sieves was placed under Ar atmosphere to a 100 mL two-neck round-bottom flask fitted with addition funnel and reflux condenser connected to a bubbler. 2M solution of trimethylaluminum in heptane (17 mL, 34 mmol) was added dropwise to the alcohol allowing gentle reflux of the mixture due to strong exothermic effect (~15 min). After the addition was completed, the flask was placed in a heated oil bath and the mixture was refluxed for additional 0.5 hour at 110° C. to insure complete conversion of trimethylaluminum to alkoxide (end of methane evolution). The mixture was cooled to room temperature under Ar, and transferred via canula to a 75 mL pressure bottle containing 500b (5.74 g, 12 mmol). The bottle was sealed under Ar, heated at 130° C. for 66 h, cooled, diluted with AcOEt (50 mL) and quenched with 10% $H_3PO_4$ (150 mL). Organic phase was separated, washed consecutively with 5% NaCl, sat. NaCl, dried over $Na_2SO_4$, and concentrated in vacuo to afford 6.71 g of crude material. Chromatography of the residue over a silica gel column with gradient DCM-MeOH (0-2%) gave 4.44 g (65%) of 501b. $^1$H NMR (400 MHz), DMSO-$d_6$, J (Hz): 1.02 (m, 12H); 1.44 (d, 3H, J=0.7); 3.18 (s, 3H); 3.41 (m, 2H); 3.54 (q, 1H, J=6.3); 3.80 (dd, 1H, $J_1$=3.7, $J_2$=11.6); 3.91 (dd, 1H, $J_1$=2.8, $J_2$=11.6); 3.95 (q, 1H, J=3.2); 4.02 (t, 1H, J=5.5); 4.21 (q, 1H, J=4.3); 5.17 (d, 1H, J=5.8); 5.92 (d, 1H, J=5.8); 7.43 (m, 7H); 7.64 (m, 4H); 11.40 (s, 1H). $^{13}$C NMR (100 MHz), MeCN-$d_3$: 12.3; 16.1; 20.0; 27.4; 56.7; 64.8; 70.0; 74.8; 76.6; 83.1; 85.5; 87.4; 111.5; 128.9; 129.0; 131.0; 131.1; 133.6; 134.3; 136.2; 136.4; 136.5; 151.7; 164.9.

502b was synthesized analogously from chiral (R)-2-methoxy-1-propanol (er=94:6, 16.8 g, 0.187 mol), and 500b (5.26 g, 11 mmol). Obtained: 3.60 g (58%), dr=94:6. 501a, 502a, 569a-z are prepared accordingly from 5'-TBDPS-anhydro-5-MeU (500b).

2. Aluminum Alkoxide-Promoted Ring Opening of TBDPS-Protected Anhydro-Nucleosides with Secondary Alcohols, Diastereomeric Resolution.
Typical Procedure:

5'-TBDPS-protected (R) and (S) 2'-(1-methyl-2-methoxyethyloxy)-uridine (512a and 513a)

Racemic commercial 2-methoxy-2-propanol (88 mL, 0.9 mol) dried over 4 A molecular sieves was placed under Ar atmosphere to a 500 mL two-neck round-bottom flask fitted with addition funnel and reflux condenser connected to a bubbler. 2M solution of trimethylaluminum in heptane (60 mL, 0.12 mol) was added dropwise to the alcohol allowing gentle reflux of the mixture due to strong exothermic effect (~15 min). After the addition was complete, the flask was placed in a heated oil bath and the mixture was refluxed for additional 1 hour at 115° C. to insure complete conversion of trimethylaluminum to alkoxide (end of methane evolution). The mixture was cooled to room temperature under Ar, and transferred via canula to a 500 mL pressure bottle containing 500a (18.6 g, 0.04 mol). The bottle was sealed under Ar, heated at 150° C. for 72 h, cooled, diluted with AcOEt (300 mL) and quenched with 10% $H_3PO_4$ (600 mL). Organic phase was separated, washed consecutively with 5% NaCl, sat. NaCl, dried over $Na_2SO_4$, and concentrated in vacuo to afford 21.9 g of crude material. Chromatography of the residue over a silica gel column with gradient chloroform-AcOEt=4:1 to 1:1 gave 6.17 g (28%) of 512a (R) and 4.20 g (19%) of 513a (S).

512a:
$^1$H NMR (400 MHz), DMSO-$d_6$, J (Hz): 1.03 (s, 9H); 1.06 (d, 3H, J=6.3); 3.26 (s, 3H); 3.27 (m, 2H); 3.37 (dd, 2H, $J_1$=6.6, $J_2$=10.0); 3.77 (m, 2H); 3.93 (m, 2H); 4.11 (t, 1H, J=4.6); 4.17 (q, 1H, J=4.6); 4.82 (d, 1H, J=5.9); 5.23 (dd, 1H, $J_1$=2.2, $J_2$=8.0); 5.80 (d, 1H, J=4.4); 7.45 (m, 6H); 7.63 (m, 4H); 7.71 (d, 1H, J=8.1); 11.40 (d, 1H, J=2.0). $^{13}$C NMR (100 MHz), DMSO-$d_6$: 17.1; 18.8; 26.6; 58.4; 63.2; 68.3; 74.4; 75.7; 79.9; 83.9; 87.0; 101.5; 127.97; 127.99; 132.2; 132.7; 135.0; 135.2; 139.8; 150.4; 162.9.

513a:
$^1$H NMR (400 MHz), DMSO-$d_6$, J (Hz): 1.02 (s, 9H); 1.08 (d, 3H, J=6.4); 3.18 (s, 3H); 3.26 (m, 2H); 3.80 (m, 2H); 3.92 (m, 2H); 4.12 (t, 1H, J=4.3); 4.16 (m, 1H); 5.06 (d, 1H, J=5.7); 5.24 (dd, 1H, $J_1$=2.2, $J_2$=8.1); 5.81 (d, 1H, J=4.2); 7.45 (m, 6H); 7.63 (m, 4H); 7.72 (d, 1H, J=8.1); 11.38 (d,

1H, J=2.1). $^{13}$C NMR (100 MHz), DMSO-d$_6$: 17.2; 18.8; 26.6; 58.3; 63.5; 68.0; 74.0; 76.0; 79.8; 83.9; 87.1; 101.3; 127.9; 129.97; 130.02; 132.2; 132.7; 135.0; 135.2; 140.0; 150.4; 163.0.

512b And 513b were prepared accordingly from 500b (19.1 g, 0.04 mol), obtained: 6.18 g (27%) of 512b (R) and 5.20 g (23%) of 513b (S).

522b And 523b were prepared accordingly from racemic threo-3-methoxy-2-butanol (26.6 g, 0.256 mol) and 500b (6.69 g, 14 mmol). Obtained: 1.50 g (18%) of 522b (RR) and 0.42 g (5.2%) of 523b (SS).

532b And 533b were prepared accordingly from erythro-3-methoxy-2-butanol (21.0 g, 0.202 mol), 500b (5.26 g, 11 mmol). Obtained: 1.10 g (18%) of 532b (RS) and 0.97 g (15%) of 533b (SR).

522a, 523a, 532a, 533a, 542a-b, 543a-b are synthesized analogously from the corresponding racemic secondary alcohols and 3,2'-unhydro-U (500a) and 3,2'-anhydro-5-MeU (500b).

3. 4,4,5,5-Tetramethyl-1, 3, 2-Dioxaborolane-Promoted Ring Opening of TBDPS-Protected Anhydro-Nucleosides with Pyrimidine Desoxynucleosides, Synthesis of Nucleoside (O)-Dimers.
Typical Procedure:

TBDPS-protected 5',2'-T-(O)-MeU dimer (552b)

Thymidine (7.3 g, 30 mmol), sodium carbonate (0.11 g, 1 mmol), and anhydrous diglyme (20 mL) were placed in a 150 mL pressure bottle under Ar atmosphere. 4,4,5,5-Tetramethyl-1,3,2-dioxaborolane (8.7 mL, 60 mmol) was added, the pressure bottle was closed with a cap containing low-pressure gas valve, and heated in an oil bath to 110° C. for 15 min. The bottle was cooled to rt, and anhydronucleoside 500b (4.78 g, 10 mmol) was added. The bottle was tightly closed with a regular cap, heated at 150° C. for 64 h, cooled to rt and quenched with sat. NaHCO$_3$ (50 mL) and ethyl acetate (30 mL). The mixture was diluted with water (100 mL), extracted with ethyl acetate (50 mL), the organic phase was separated, washed with 5% NaCl, and dried over anhyd. Na$_2$SO$_4$.

Crude material (9.70 g) was chromatographed over a silica gel column with AcOEt-MeOH gradient (0-5%) to afford 2.20 g (31%) of the dimer 552b as white foam. The product was further purified by crystallization from acetone (10 mL) to afford 1.68 g of white crystals (76% yield on crystallization). $^1$H NMR (400 MHz), DMSO-d$_6$, J (Hz), δ=11.42 (s, 1H), 11.29 (s, 1H), 7.71 (d, J=0.6, 1H), 7.63 (dd, J=10.0, 3.9, 4H), 7.54-7.30 (m, 7H), 6.22 (dd, J=8.2, 6.1, 1H), 5.96 (d, J=5.4, 1H), 5.51 (d, J=5.5, 1H), 5.28 (d, J=3.9, 1H), 4.25 (dd, J=9.8, 5.0, 1H), 4.20 (s, 1H), 4.05-3.97 (m, 2H), 3.97-3.75 (m, 4H), 3.59 (dd, J=10.4, 2.6, 1H), 3.34 (s, 1H), 2.11-1.92 (m, 2H), 1.80 (s, 3H), 1.46 (s, 3H), 1.02 (s, 9H). $^{13}$C NMR (100 MHz), acetone-d$_6$: 12.3; 12.4; 20.0; 27.4; 40.7; 64.7; 69.9; 71.6; 72.8; 83.6; 85.4; 86.0; 86.8; 87.6; 111.1; 111.2; 128.8; 128.9; 130.9; 140.0; 133.5; 134.1; 135.8; 136.2; 136.4; 137.2; 151.4; 151.5; 164.2; 164.4.

552a is synthesized analogously from desoxyuridine and 500a.

4. TBDPS Deprotection from Condensation Products.
Typical Procedure:

2'-(R)-(1-methyl-2-methoxyethyloxy)-uridine (514a)

To a solution of 512a (5.83 g, 10.5 mmol) in anhyd. THF (30 mL) under Ar atmosphere was added triethylammonium trihydrofluoride (6.8 mL; 42 mmol) and the mixture was stirred at rt for 72 h. The mixture was concentrated in vacuo and chromatographed over a column of silica gel with chloroform-methanol (20:1) eluent. Subsequent crystallization of the residue from 250 mL of ether gave 2.56 g (77%) of pure 514a as a white crystalline solid:

$^1$H NMR (400 MHz), DMSO-d$_6$, J (Hz): 1.04 (d, 3H, J=6.3); 3.25 (m, 1H); 3.26 (s, 3H); 3.36 (dd, 1H, J$_1$=6.7, J$_2$=10.0); 3.59 (tt, 1H, J$_1$=3.6, J$_2$=11.9); 3.63 (tt, 1H, J$_1$=3.6, J$_2$=11.9); 3.74 (sextet, 1H, J=6.3); 3.84 (d, 3H, J=3.1); 4.06 (quintet, 1H, J=4.8); 4.68 (d, 1H, J=4.7); 5.13 (t, 1H, J=5.0); 5.65 (d, 1H, J=8.1); 5.79 (d, 1H, J=4.4); 7.94 (d, 1H, J=8.1); 11.3 (s, 1H).

503b (dr~94:6): was synthesized analogously from 3.48 g (6.1 mmol) of 501b (dr=94:6). White foam after column purification, yield: 2.00 g (99%).

504b: was synthesized analogously from 4.21 g (7.4 mmol) of 2e. White foam after column purification, yield: 2.36 g (97%).

514b: from 5.68 g (10 mmol) of 512b. White foam after column purification, yield: 3.07 g (93%).

515a: from 3.74 g (6.8 mmol) of 513a. Yield after column purification and crystallization from ether: 1.70 g (79%), white crystals.

515b: from 4.93 g (8.7 mmol) of 513b. White foam after column purification, yield: 2.07 g (72%).

524b: from 1.44 g (2.5 mmol) of 522b. White foam after column purification, yield: 0.83 g (97%).

525b: from 0.39 g (0.67 mmol) of 523b. White foam after column purification, yield: 0.20 g (87%).

534b: from 1.01 g (1.7 mmol) of 532b. White foam after column purification, yield: 0.56 g (97%).

535b: from 0.86 g (1.5 mmol) of 533b. White foam after column purification, yield: 0.52 g (quant.).

553b: from 1.89 g (2.6 mmol) of 552b. White crystals after column purification, yield: 1.28 g (91%).

Compounds 503a, 504a, 524a, 525a, 534a, 535a, 544a-b, 545a-b, 553a, and 570a-z are prepared analogously.
5. DMTr-Protection of Condensation Products.
Typical Procedure:

5'-DMTr-protected 2'-(R)-(1-methyl-2-methoxyethyloxy)-5-methyluridine (516b)

To a mixture of 514b (2.90 g; 8.8 mmol) and DMTrCl (3.29 g, 9.7 mmol) at 0° C. under argon atmosphere were added consecutively anhyd. pyridine (40 mL) and triethylamine (1.4 mL; 9.7 mmol). The cooling bath was removed and the mixture was stirred at rt for 4 h. The mixture was concentrated under the reduced pressure at 30° C. and partitioned between ethyl acetate (75 mL) and sat. NaHCO$_3$ (75 mL). The organic phase was separated, dried over anhyd. Na$_2$CO$_3$, concentrated and chromatographed over a CombiFlash silica gel column (120 g) with gradient of 50% DCM in hexane to 100% DCM in the presence of 2% Et$_3$N. Pulled fractions were concentrated, diluted with ethyl acetate (50 mL), filtered and evaporated to afford 4.98 g (89%) of 516b as white foam.

$^1$H NMR (400 MHz), DMSO-d$_6$, J (Hz): 1.08 (d, 3H, J=6.4); 1.36 (d, 3H, J=1.0); 3.17 (dd, 1H, J$_1$=2.6, J$_2$=10.7); 3.26 (s, 3H); 3.30 (m, 1H); 3.40 (dd, 1H, J$_1$=6.8, J$_2$=10.1); 3.74 (s, 6H); 3.81 (tt, 1H, J$_1$=4.2, J$_2$=6.5); 3.97 (dd, 1H, J$_1$=3.8, J$_2$=6.5); 4.24 (m, 2H): 4.83 (d, 1H, J=5.2); 5.83 (d, 1H, J=4.9); 6.91 (d split, 4H, J=9.0); 7.27 (m, 5H); 7.32 (t, 2H, J=7.2); 7.40 (d split, 2H, J=7.2); 7.52 (d, 1H, J=1.2); 11.39 (s, 1H). $^{13}$C NMR (100 MHz), MeCN-d$_3$: 12.2; 17.3; 55.9; 59.3; 64.1; 70.5; 76.8; 77.3; 82.0; 84.5; 87.6; 88.2;

111.4; 114.2; 128.0; 128.94; 129.01; 131.0; 136.4; 136.5; 136.7; 145.8; 151.8; 159.76; 159.79; 165.0.

505b (dr~94:6): was prepared analogously from 503b (dr=94:6) (1.95 g, 5.9 mmol). White foam after chromatography, yield: 3.29 g, (88%).

506b: from 504b (2.30 g, 7.0 mmol). White foam after chromatography, yield: 3.77 g, (85%).

517b: from 515b (1.95 g, 5.9 mmol). White foam, yield: 2.94 g, (79%).

526b: from 524b (0.77 g, 2.2 mmol). White foam, yield: 1.33 g, (94%)

527b: from 523b (0.19 g, 0.55 mmol). White foam, yield: 0.34 g, (94%)

536b: from 534b (0.54 g, 1.6 mmol). White foam, yield: 0.90 g, (87%)

537b: from 535b (0.34 g, 1.0 mmol). White foam, yield: 0.62 g, (95%)

554b: from 553b (1.24 g, 2.6 mmol). White foam, yield: 1.73 g, (85%)

Compounds 505a, 506a, 516a, 517a, 526a, 527a, 536a, 537a, 546a-b, 547a-b, 554a, and 571a-z are prepared analogously.

6. Sodium Hydride-Promoted Alkylation of Protected Nucleosides with Primary Mesylates.

Typical Procedure:

5'-DMTr-2'-(S)-(2-methyl-2-methoxyethyloxy)-adenosine-N-benzoyl (506d)

Sodium hydride (1.84 g, 46 mmol) was added to a stirred and cooled (0° C.) mixture of 507d (14.2 g, 21 mmol), anhyd. DMSO (70 mL), and anhyd. THF (50 mL) under Ar atmosphere, the mixture was stirred at 0° C. for 0.5 h, and (S)-2-methoxypropylmethanesulfonate (8.9 g, 53 mmol) in THF (20 mL) was added. The mixture was allowed to warm up to rt, and then heated in an oil bath at 50° C. for 24 h. The mixture was cooled to 0° C. and quenched by consecutive addition of sat. $NH_4Cl$ (200 mL), ethyl acetate (150 mL), and water (30 mL). The organic phase was separated, washed with sat. NaCl and dried over anhyd. $Na_2SO_4$. Crude residue (22.2 g) was chromatographed over a column of silica gel with ethyl acetate-hexane (2:1)-methanol gradient (0-5%) to afford 3.96 g (25%) of 506d as white foam.

$^1$H NMR (400 MHz), DMSO-$d_6$, J (Hz): 11.25 (1 H, s), 8.70 (1 H, s), 8.62 (1 H, s), 8.05 (2 H, m), 7.65 (1 H, t, J 7.4), 7.56 (2 H, t, J 7.6), 7.37 (1 H, m), 7.23 (7 H, m), 6.84 (4 H, m), 6.18 (1 H, d, J 4.8), 5.26 (1 H, d, J 6.0), 4.73 (1 H, t, J 4.9), 4.46 (1 H, dd, J 10.7, 5.2), 4.13 (1 H, dd, J 9.1, 4.8), 3.72 (3 H, s), 3.72 (3 H, s), 3.60 (1 H, dd, J 10.4, 4.1), 3.47 (1 H, m), 3.41 (1 H, m), 3.25 (2 H, m), 3.13 (3 H, s), 0.99 (3 H, d, J 6.2). $^{13}$C NMR (100 MHz), acetone-$d_6$: 16.1; 55.4; 56.5; 64.4; 70.8; 74.9; 76.5; 82.7; 84.9; 87.0; 87.8; 113.8; 126.0; 127.5; 128.5; 128.9; 129.1; 129.3; 130.8; 133.1; 134.9; 135.6; 136.7; 143.5; 145.9; 151.1; 152.6; 152.9; 159.5; 165.9.

Compounds 546d-e are prepared analogously by alkylation of 507d-e with 2-bromopropionylmethylamide. Compounds 558d-e, 563a-b, 566d-e are prepared analogously by alkylation of the corresponding protected nucleosides 507d-e, 561a-b, and 556d-e with protected nucleoside 5'-mesylates 557d-e, and 562a-b. Compounds 573a-z are prepared by alkylation of 507d applying 3 eq of NaH and HCl salts of the corresponding mesylates 568a-z.

7. Synthesis of 5'-DMTr-N-Pivaloyl Pyrimidine Nucleosides.

Typical Procedure:

5'-DMTr-N-pivaloylthymidine (561b)

TMSCl (2.7 ml, 21 mmol) was added to a solution of thymidine (2.42 g, 10 mmol) in anhyd. pyridine (20 mL) under Ar atmosphere. The mixture was stirred at rt for 4 h, and pivaloyl chloride (1.3 mL, 10.5 mmol) was added. The mixture was stirred at rt for 72 h, and water (0.19 mL, 10.5 mmol) was added. After stirring at rt for 16 h, DMTrCl (3.73 g, 11 mmol) was added, and the stirring was continued for an additional 3.5 h. The mixture was diluted with AcOEt (40 mL) and quenched with 10% aq. $H_3PO_4$ (150 mL), washed with 5% NaCl and dried over anhyd. $Na_2SO_4$. The crude mixture (7.51 g) was chromatographed over a column of silica gel with ethyl acetate: hexane (1:1)-methanol gradient (0-3%) to afford 561b, 3.35 g, 53%. $^1$H NMR (400 MHz), MeCN-$d_3$, J (Hz): 7.66 (1 H, s), 7.40 (2 H, m), 7.32 (2 H, t, J 7.6), 7.26 (5 H, t, J 6.5), 6.90 (4 H, dd, J 8.9, 1.0), 6.18 (1 H, t, J 6.6), 5.37 (1 H, s), 4.36 (1 H, s), 3.92 (1 H, dd, J 7.3, 3.9), 3.74 (6 H, s), 3.21 (2 H, s), 2.28 (2 H, m), 1.51 (3 H, d, J 0.9), 1.23 (9 H, s).

Compound 561a is synthesized analogously.

8. Synthesis of Phosphoramidites of Modified Nucleosides.

Typical Procedure:

5'-DMTr-2'-(R)-(1-methyl-2-methoxyethyloxy)-5-methyluridine-3'-phosphoramidite (518b)

To a flask, containing DMTr-protected nucleoside 516b (2.0 g, 3.2 mmol) were added consecutively under argon atmosphere anhyd. DCM (20 mL), DIEA (0.66 mL, 3.8 mmol), and cyanoethylchlorophosphor-N,N-diisopropylamidite (0.85 mL, 3.8 mmol). The mixture was stirred at rt overnight and partitioned between ethyl acetate (20 mL) and sat. $NaHCO_3$ (20 mL). Organic phase was separated, dried over anhyd. $Na_2SO_4$, concentrated and chromatographed over a CombiFlash silica gel column (40 g) with ethyl acetate-hexane (1:1) eluent in the presence of 0.25% of $Et_3N$. Obtained 2.06 g (77%) of pure 518b (mixture of diastereomers) as white foam. $^1$H NMR (400 MHz), MeCN-$d_3$, J (Hz): 1.07 (d, 3H, J=6.8); 1.14 (d, 3H, J=6.3); 1.19 (dd, 9H, $J_1$=2.9, $J_2$=6.8); 1.35 (s, 3H); 2.52 (t, 1H, J=6.0); 2.72 (q split, 1H, J=6.2); 3.30 (s, 1.5H); 3.32 (s, 1.5H); 3.34 (m, 1H); 3.37 (s, 1H); 3.48 (m, 1H); 3.63 (m, 2.5H); 3.74 (m, 0.5H); 3.78 (s split, 6H); 3.91 (m, 2H); 4.15 (d, 0.5H, J=2.6); 4.24 (d, 0.5H, J=2.5); 4.52 (m, 2H); 5.94 (t, 1H, J=5.3); 6.90 (dd, 4H, $J_1$=4.7, $J_2$=8.4); 7.27 (m, 1H); 7.35 (m, 6H); 7.49 (dd, 2H, $J_1$=3.3, $J_2$=8.0); 7.53 (s, 0.5H); 7.57 (s, 0.5H); 9.20 (s broad, 1H). $^{31}$P NMR (160 MHz), MeCN-$d_3$: 149.2; 149.6.

508b (dr~94:6): was prepared analogously from 505b (2.0 g, 3.2 mmol). Yield: 1.98 g (74%), white foam.

509b: from 506b (2.0 g, 3.2 mmol). Yield: 2.14 g (80%), white foam.

509d: from 506d (3.26 g, 4.4 mmol). Yield: 3.17 g (76%), white foam.

519b: from 517b (1.50 g, 2.4 mmol). Yield: 1.52 g (76%), white foam.

528b: from 526b (0.98 g, 1.5 mmol). Yield: 0.96 g (76%), white foam.

529b: from 527b (0.34 g, 0.5 mmol). Yield: 0.34 g (81%), white foam.

538b: from 536b (0.59 g, 0.9 mmol). Yield: 0.46 g (61%), white foam.

539b: from 537b (0.62 g, 0.96 mmol). Yield: 0.64 g (79%), white foam.

Compounds 508a,c; 509a,c; 518a,c; 519a,c; 528a,c; 529a,c; 538a,c; 539a,c; 548a-e; 549a-e; 574a-z; 575a-z; and 576a-z are prepared accordingly.

9. Loading of Condensation Products on CPG.
Typical Procedure:

Loading of 5'-DMTr-2'-(R)-(1-methyl-2-methoxy-ethyloxy)-5-methyluridine (516b) on CPG To a mixture of 516b (500 mg, 0.79 mmol) and succinic anhydride (160 mg, 1.6 mmol) were added anhyd. pyridine (3 mL) and triethylamine (0.42 mL, 3 mmol) under argon atmosphere. After stirring at rt for 24 h, the mixture was diluted with toluene (5 mL), evaporated under the reduced pressure, and coevaporated again with 10 mL of toluene. The residue was partitioned between water and toluene-ethyl acetate 1:1. The organic phase was separated, washed with 5% aq. sodium chloride and dried over anhyd. $Na_2SO_4$. Evaporation of the solvent gave 589 mg (quantitative) of essentially pure 3'-succinate as free acid containing some toluene that was used in the next step without further purification. $^1$H NMR (400 MHz), MeCN-$d_3$, J (Hz): 1.08 (d, 3H, J=6.4); 1.37 (d, 3H, J=1.3); 2.60 (m, 2H); 2.65 (m, 2H); 3.28 (s, 3H); 3.30 (m, 3H); 3.40 (m, 2H); 3.78 (m, 1H); 3.79 (s split, 6H); 4.15 (q, 1H, J=2.7); 4.54 (dd, 1H, $J_1$=5.6, $J_2$=6.8); 5.45 (dd, 1H, $J_1$=3.0, $J_2$=5.5); 5.94 (d, 1H, J=6.8); 6.91 (dd, 4H, $J_1$=1.1, $J_2$=9.0); 7.34 (m, 6H); 7.47 (m, 3H); 9.14 (s broad, 1H).

To a mixture of the succinate (0.79 mmol) and HBTU (330 mg, 0.87 mmol) were added anhyd. DMF (30 mL) and DIEA (0.42 mL, 2.4 mmol) under argon atmosphere. After standing for 5 min, CPG-500 (maximum loading 140 µmol/g) (6.0 g, 0.87 mmol) was added and the mixture was placed on a shaker for 3 h. The mixture was filtered, the residue was washed consecutively with DCM, 20% methanol in DCM, DCM twice, and dried in vacuum to afford 6.13 g of precapped support (loading 90.7 µmol/g). Precapped product was treated under argon atmosphere with anhyd. pyridine (30 mL), triethylamine (2.8 mL, 20 mmol), and acetic anhydride (1.9 mL, 20 mmol). After shaking for 1 h, the solids were filtered, washed twice with DCM, once with 20% MeOH in DCM, and once again twice with DCM, and dried under high vacuum for 1 h to afford support 520b. Loading after cupping: 87.3 µmol/g.

510b: was prepared analogously from 505b (630 mg, 1 mmol). Obtained: 10.3 g, loading 74 µmol/g.

511b: from 506b (630 mg, 1 mmol). Obtained: 10.2 g, loading 66 µmol/g.

511d: from 506d (500 mg, 0.67 mmol). Obtained: 5.2 g, loading 79 µmol/g.

521b: from 517b (500 mg, 0.79 mmol). Obtained: 6.3 g, loading 91 µmol/g.

530b: from 526b (340 mg, 0.53 mmol). Obtained: 4.9 g, loading 61 µmol/g.

540b: from 536b (320 mg, 0.5 mmol). Obtained: 4.1 g, loading 80 µmol/g.

Supports 510a,c-e; 511a,c-e; 520a,c; 512a,c; 530a,c; 531a-c; 540a,c; 541a-c; 550a-e; 551a-e; 559d-e; 565a-c; 565d-e; 577a-z; 578a-z; and 579a-z are prepared analogously.

10. Loading of Bivalent Nucleosides (554a-c) on CPG.
Typical Procedure:

Loading of DMTr-protected 5',2'-T-(O)-MeU dimer (554b) on CPG

Succinic anhydride (0.15 g, 1.5 mmol) was added to a stirred and cooled (0° C.) solution of the dimer 554b (0.82 g, 0.96 mmol), DMAP (0.18 g, 1.5 mmol) in anhyd. pyridine (5 mL) under Ar atmosphere. The mixture was allowed to warm up to rt and stirred for 48 h. The mixture was diluted with AcOEt (10 mL) and quenched with 5% aq. $H_3PO_4$ (30 mL), washed with 10% NaCl and dried over anhyd. $Na_2SO_4$. Evaporation of the solvent followed by double coevaporation with a mixture of toluene (20 mL) and acetonitrile (10 mL) gave succinates of the dimer as a mixture of isomeric monoacids and diacid in ~1:1 ratio. Yield: 0.67 g, 74%. This mixture (0.95 g, 1.01 mmol based on DMTr) was dissolved in anhyd. DMF (50 mL) under Ar atmosphere, and HBTU (0.65 g, 1.71 mmol), and DIEA (0.82 mL, 4.7 mmol) were consecutively added. The mixture was shaken for 5 min, and CPG-500 (maximum loading 147 µmol/g) (12.0 g, 1.74 mmol) was added. The mixture was shaken for 3 h, and methanol (1 mL, 30 mmol) was added. After shaking for additional 0.5 h, the mixture was filtered, the residue was washed consecutively with DCM, 20% methanol in DCM, DCM twice, and dried in vacuum to afford 12.5 g of precapped support (loading 60.0 µmol/g).

The support was capped by consecutive addition of anhyd. pyridine (50 mL), triethylamine (5.6 mL, 40 mmol), and acetic anhydride (3.8 mL, 40 mmol). After shaking for 1 h, the mixture was filtered, the residue was washed consecutively with DCM, 20% methanol in DCM, DCM twice, and dried in vacuum to afford 12.4 g of capped support 555b (loading 56 µmol/g).

Supports 555a,c are prepared analogously.

Serum Incubation Assay

Blood of 8 human volunteers (270 mL) is collected and kept at room temperature for 3 hours. The blood pool is then centrifuged at 20° C. and 3000 rcf using Megafuge 1.0 (Heraeus Instruments, Kendro Laboratory Products GmbH, Langenselbold) to separate the serum from the cellular fraction. The supernatant is stored in aliquots at −20° C. and used as needed. Alternatively, human serum or mouse serum obtained from Sigma (Sigma-Aldrich Chemie GmbH, Taufkirchen, Germany, cat. No. human serum H1513, mouse serum M5905) is employed. Assay results reported herein are consistent among the different human serum sources. Mouse serum showed somewhat higher exonucleolytic activity than human serum.

Double stranded RNAs (300 µmol, ca. 4.2 µg) dissolved in 6 µl phosphate buffered saline (PBS) are added to 60 µl human serum in a 1.5 ml Eppendorf tube, and the mixture is incubated for varying extents of time, e.g. 0, 15, or 30 minutes, or 1, 2, 4, 8, 16, or 24 hours in a thermomixer (Eppendorf thermomixer comfort; Eppendorf, Hamburg, Germany) at 37° C. and 1050 rpm. Subsequently, the whole tube containing the RNA/serum solution is immediately processed further or frozen in liquid nitrogen and stored at −80° C. until analysis. As a control, the same amount of double stranded RNA is added to 60 µl annealing buffer, incubated a 37° C. for 0, 24 or 48 hours, and immediately further processed or frozen in liquid nitrogen and stored at −80° C. until analysis.

Analysis by Electrophoresis and "Stains all" Detection

For analysis, frozen serum incubation samples from store are thawed, their constituents are isolated by phenol-extraction and ethanol-precipitation, separated on denaturing 14% polyacrylamide gels (6M Urea, 20% formamide, Carl Roth GmbH & Co KG Karlsruhe, Germany) and detected by staining with the "stains-all" reagent (Sigma-Aldrich Chemie GmbH, Steinheim, Germany). Reaction mixtures from incubation of selected dsRNAs are further analysed covering the time points 8 hours, 16 hours and 24 hours.

Isolation of siRNA

For analysis, the frozen samples are placed on ice and 450 µl of 0.5 M NaCl is added, followed by brief vortexing. After complete thawing, the resulting solution is transferred to Phase-Lock Gel tubes (Eppendorf, Hamburg, Germany; cat. No. 0032 005.152), fixed with 500 µl 50% phenol, 48% chloroform, 2% isoamylacohol (Carl Roth GmbH & Co KG, Karlsruhe, Germany, cat. No. A156.2), and an additional 300 µl chloroform are added. The tubes are vortexed vigorously for 30 seconds and subsequently centrifuged for 15 min at 16.200 rcf and 4° C. The aqueous supernatant is transferred to a fresh tube, mixed with 40 µl 3M Na-acetate pH 5.2, 1 µl GlycoBlue (Ambion, TX, USA; cat. No. 9515) and 1 ml Ethanol 95%, and vortexed vigorously for ca. 20 s. Precipitation of RNA is brought to completion over night at −20° C.

Denaturing Gel Electrophoresis and RNA Staining

The following day, tubes are centrifuged for 30 min at 16.200 rcf and 4° C. The supernatant is removed and discarded. The RNA pellet is ished with 500 µl ice-cold Ethanol 70%, and re-pelleted by centrifugation for 10 min at 16.200 rcf and 4° C. All liquid is removed, the pellet is air-dried for 1 min and dissolved in 12 µl gel loading buffer (95% formamide, 5% EDTA 1M, 0.02% xylene cyanol, 0.02% bromophenol blue). The gel is pre-run for 1 h at 100 W. The samples are boiled for 10 min at 95° C. and chilled quickly on ice. 4 µl are loaded on a denaturing 14% polyacrylamide gel (8M Urea, 20% formamide, 19:1 acrylamide:N,N-Methylenebisacrylamide). The RNA is separated for about 40 min at 100 W (Sequi-Gen GT gel system, 38×30 cm, Bio-Rad Laboratories, Hercules, Calif., USA, cat. no. 165-3862). RNA bands are visualized by staining with the "stains-all" reagent (Sigma-Aldrich Chemie GmbH, Steinheim, Germany, cat. no. E9379) according to manufacturer's instructions.

Analysis by LC/MS

Frozen serum incubation samples from store are thawed, their constituents are isolated by phenol-extraction and ethanol-precipitation, the resulting pellet is dissolved in 50 µl of water and 42 µl of this solution is injected into the HPLC-system (Amersham Biosciences Ettan mLC-System equipped with UV-detection system and Jetstream column heater coupled to Thermo Finnigan LCQ DecaXp mass spectrometer; HPLC column: Waters Xterra C8-MS; 2.1×50 mm; particle size 2.5 µm; 60° C.; Flow 200 µl/min; UV-Detection at 254 nm; ESI source and IonTrap-detector, total ion current detection for MS-detection). The MS-instrument is started with a 3 min time delay after the injection to protect the mass spectrometer from salt and other unbound sample impurities. An eluent gradient is employed as follows:

| Eluents: | | |
|---|---|---|
| A: | 400 mM Hexafluoroisopropanol/16.3 mM Triethylamine in deionized water; pH = 7.9 | |
| B: | Methanol (LC-MS grade) | |
| Gradient table: | 0-> 3 min: | 1% B; |
| | 3->33 min: | 1%->24% B linear; |
| | 33.1 min: | 100% B; |
| | 33.1->35 min: | 100% B |
| | 35.1 min: | 1% B |
| | 35.1->38 min: | 1% B |

Due to the denaturing conditions on the column (60° C.), all sample fragments elute as single strands. Every fragment is detected as one peak in the UV- and the TIC-chromatogram. A raw mass spectrum of every peak is extracted from the TIC-chromatogram and deconvoluted using the software "Bioworks", Version 3.1 (Thermo Electron GmbH, Dreieich, Germany). At the end of each run, the column is ished and re-equilibrated.

Comparison between the experimentally detected and the calculated masses of all possible fragments of both duplex strands leads to the identification of the cleavage fragments generated during serum incubation. The LC-MS method is insensitive to phosphate-induced shifts as are the gel assays and allows an exact mapping of all cleavage sites.

Data evaluation steps:

1.) Average isotopic masses are calculated for all hypothetical fragments of both the sense and the antisense strand.
2.) 62.0 Da are added to the hypothetical fragment masses to account for a cyclic diester phosphate terminus at the cleavage site; for a cyclic diester phosphorothioate at the cleavage position, +78.06 Da are added; 80.0 Da are added for a 2'- or 3'-monoester phosphate group, and +96.06 Da are added for a phosphorothioate monoester.
3.) All experimental masses are compared to these predicted masses; a fragment is identified if its experimentally determined mass falls to within +/−1 Da of the predicted mass.
4.) Fragments unequivocally assignable allow the identification of cleavage positions.
5.) The increase or decrease of a peak at different time points allow conclusions on whether the cleavage is a primary or secondary event.

2'-3'-cyclic phosphates and the resulting hydrolyzed 2'- or 3'-phosphates as possible termini after the cleavage event are included into the mass calculation of the fragments. This end group analysis provided an insight to the cleavage mechanism. If a cyclic phosphate is detected at the 3'-end of a fragment resulting from cleavage, a nucleophilic attack of the 2'-OH on the 3'-O—P phosphorus of the internal base must have been involved in the cleavage mechanism. For stabilization against degradation following this mechanism, a 2'-modification, e.g. a 2'-O-Methyl substitution on the respective nucleotide, may be employed.

Determination of siRNA Degradation Time Course by HPLC Following Proteinase K Treatment of Serum Samples In order to get a more quantitative means of determining siRNA strand degradation, a method comprising Proteinase K treatment of serum samples followed by the separation of serum sample constituents on an HPLC is developed. By comparison of different modified and unmodified siRNAs, this method can be used to identify sites and sequence motifs in siRNA strands that are particularly vulnerable to nucleolytic degradation.

The example below shows the analyses of serum samples which are contacted with siRNAs in vitro. However, this method can equally be applied to biological samples ex vivo, i.e. obtained from a subject which is contacted with an siRNA in vivo. Proteinase K (20 mg/ml) is obtained from peQLab (Erlangen, Germany; Cat.-No. 04-1075) and diluted 1:1 with deionized water (18.2 mΩ) to a final concentration of 10 mg/ml Proteinase K. Proteinase K Buffer (4.0 ml TRIS-HCl 1M pH 7.5, 1.0 ml EDTA 0.5M, 1.2 ml NaCl 5M, 4.0 ml SDS 10%) is prepared fresh and kept at 50° C. until use to avoid precipitation.

A 40 mer of poly(L-dT), (L-dT)$_{40}$ is obtained from Noxxon Pharma AG (Berlin, Germany) and used as an internal standard. Polymers of the L-enantiomers of nucleic acids show an extraordinary stability towards nucleolytic degradation (Klussman S, et al., Nature Biotechn. 1996, 14:1112) but otherwise very similar properties when compared to naturally occurring nucleic acids consisting of R-enantiomers.

Proteinase K Treatment of Serum Incubation Samples

To terminate the siRNA-degradation, 25 µl of Proteinase K buffer are added to serum incubation samples immediately after expiry of the respective incubation period, the mixture vortexed at highest speed for 5 s (Vortex Genie 2, Scientific Industries, Inc., Bohemia, N.Y., USA, cat. no. SI 0256), 8 µl Proteinase K (10 mg/ml) are added followed by vortexing for 5 s, and finally the mixture is incubated for 20 min in a thermomixer at 42° C. and 1050 rpm.

6 µl of a 50 µM solution (300 µmole) of (L-dT)$_{40}$ are added as an internal standard, the solution is vortexed for 5 s, and the tube centrifuged for 1 min in a tabletop centrifuge to collect all droplets clinging to the inner surfaces of the tube at the bottom. The solution is transferred to a Microcon Centrifugal Filter Unit YM-100 (Millipore GmbH, Eschborn, Germany, Cat. No. 42413) and filtered by centrifugation at 21900 rcf for 45 min. The incubation tube is ished with 47.5 µl deionized water (18.2 mΩ), the ish filtered through the Microcon Centrifugal Filter Unit at 21900 rcf for 15 min, and the ish step repeated. Approximately 180 µl of the theoretical total volume of 200 µl are on average recovered after the second ishing step.

Ion Exchange Chromatographic Separation of siRNA Single Strands from Each Other and from Degradation Products:

A Dionex BioLC HPLC-system equipped with inline-degasser, autosampler, column oven and fixed wavelength UV-detector (Dionex GmbH, Idstein, Germany) is used under denaturing conditions. Standard run parameters are:

| | |
|---|---|
| Column: | Dionex DNA-Pac100; 4 × 250 mm |
| Temperature: | 75° C. |
| Eluent A: | 10 mM NaClO$_4$, 20 mM TRIS-HCl, 1 mM EDTA; 10% acetonitrile, pH = 8.0 |
| Eluent B: | 800 mM NaClO$_4$, 20 mM TRIS-HCl, 1 mM EDTA; 10% acetonitrile, pH = 8.0 |
| Detection: | @ 260 nm |
| Gradient: | 0-1 min: 10% B |
| | 1-11 min: 10%->35% B |
| | 11-12 min: 35% B->100% B |
| | 12-14 min: 100% B->10% B |
| | 14-16 min: 10% B for column reequilibration |
| Injection volume: | 20 µl |

Where separation between the two strands of an siRNA is not satisfactory or a degradation fragment co-eluted with one strand, the chromatographic parameters are adjusted by changing temperature, pH, and/or the concentration of acetonitrile, until separation is achieved which allowed separate quantitation of the peaks from sense and antisense strand.

Peak areas for full length strands are obtained by integration of the UV detector signal using software supplied by the manufacturer of the instrument (Chromeleon 6.5; Dionex GmbH, Idstein, Germany).

Data Analysis:

Integrated sense strand, antisense strand, and internal standard peak areas are obtained for all samples and the normalization control.

A correction factor CF, accounting for liquid losses in the filtration and ishing steps, is determined for every sample by calculating the ratio of experimental to theoretical internal standard peak area. The theoretical internal standard peak area is obtained, e.g. from a calibration curve of the internal standard obtained by injecting 20 µl each of a serial dilution of the 50 µM solution of (L-dT)$_{40}$ onto the HPLC column, and calculation of the theoretical peak area corresponding to 30 µmole (L-dT)$_{40}$ with the equation obtained by linear least square fit to the peak areas from the dilution series. The correction factor CF to be applied to the peak areas of the sense and antisense strand is obtained as:

$$CF = PeakArea_{intStd} \text{ (theoretical)} / PeakArea_{intStd} \text{ (Sample)}$$

This treatment assumes that, by virtue of ishing the filter twice, virtually complete recovery is achieved in the combined filtrates, and corrects for the variable volume of ish water retained in the filter, such that peak areas from different samples can be compared. The peak areas obtained for the sense and antisense strand peaks for each time point are then multiplied with the correction factor CF to obtain Normalized Peak Areas ($NPA_{sense,t}$, $NPA_{antisense,t}$):

$$NPA_{sense \text{ or } antisense, t} = (PeakArea_{sense \text{ or } antisense, t}) \times CF$$

To obtain the relative amount of remaining Full Length Product (% FLP) for the sense and antisense strands at time t, the Normalized Peak Area for each strand at time t=0 min ($NPA_{sense,t=0}$, $NPA_{antisense,t=0}$) is set as 100%, and the NPAs from other time points are divided by these values.

$$\% FLP_{t=1,2,3 \ldots n} = (NPA_{t=1,2,3 \ldots n} / NPA_{t=0}) \times 100$$

The value obtained from the control sample, where the siRNA is incubated with annealing buffer only, may serve as a control of the accuracy of the method. The % FLP for both strands should lie near 100%, within error margins, regardless of time of incubation.

The degradation half life $t_{1/2}$ may then be calculated for each strand, assuming first order kinetics, from the slope of a linear least square fit to a plot of ln(% FLP) versus time as:

$$t_{1/2} = \ln(0.5)/\text{slope}$$

The various embodiments described above can be combined to provide further embodiments. All of the U.S. patents, U.S. patent application publications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. An oligonucleotide comprising a nucleosidic end cap of one of the following formulas:

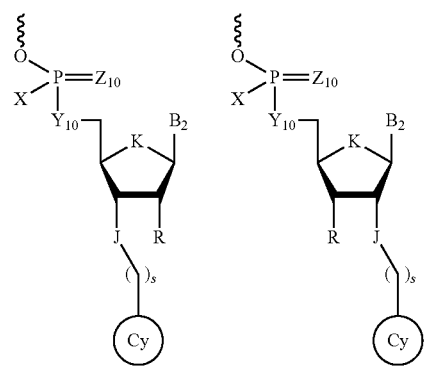

wherein:

J is an ether linkage;

K is O;

B₁ and B₂ are each independently a natural or modified nucleobase;

X is H, OH, OM, SH, SM, optionally substituted alkyl, optionally substituted alkoxy, optionally substituted alkylthio, optionally substituted alkylamino, or optionally substituted dialkylamino, where M represents independently for each occurrence an alkali metal or a transition metal with an overall charge of +1;

$Z_{10}$ is O;

$Y_{10}$ is O;

R and $R_2$ are each independently H, OH, SH, halogen, optionally substituted alkyl, optionally substituted alkenyl, optionally substituted alkynyl, optionally substituted alkoxy, optionally substituted alkylthio, optionally substituted alkylamino, or optionally substituted dialkylamino;

s is 1; and

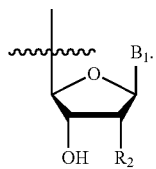

2. The oligonucleotide of claim 1, wherein:

R is H, OH, OMe, F, or O(CH₂)₂OMe; and $R^2$ is OH, F, $C_1$-$C_{32}$ alkyl, $C_1$-$C_{32}$ alkoxy, —(CH₂)ₙ—NR$^b$R$^c$, —O(CH₂)ₙ—NR$^b$R$^c$, —[O(CH₂)ᵣ]ₘ—OR$^b$, —[O(CH₂)ᵣ]ₘ—NR$^b$R$^c$, —(CH₂)ₙ—O—NR$^b$R$^c$, —O—(CH₂)ₙ—O—NR$^b$R$^c$, —[O(CH₂)ᵣ]ₘ—O—NR$^b$R$^c$, —(CH₂)ₙ—N(R$^b$)—C(=NR$^b$)—NR$^b$R$^c$, —O—(CH₂)ₙ—NR$^b$—C(=NR$^b$)—NR$^b$R$^c$, —(CH₂)ₙ—O—NR$^b$—C(=NR$^b$)—NR$^b$R$^c$, —O—(CH₂)ₙ—O—NR$^b$—C(=NR$^b$)—NR$^b$R$^c$, or —[O(CH₂)ᵣ]ₘ—O—NR$^b$—C(=NR$^b$)—NR$^b$R$^c$, where R$^b$ and R$^c$ are each independently hydrogen or $C_1$-$C_{32}$ alkyl, and n, m and r are each independently an integer from 1-20.

3. The oligonucleotide of claim 1, wherein said oligonucleotide is single-stranded siRNA.

4. The oligonucleotide of claim 1, wherein said oligonucleotide is double-stranded siRNA.

5. The oligonucleotide of claim 1, wherein B₂ is

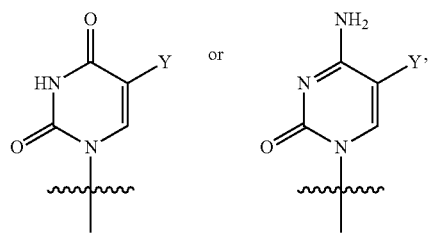

wherein Y is H or CH₃.

6. The oligonucleotide of claim 5, wherein B₂ is

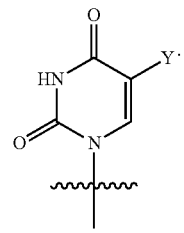

7. The oligonucleotide of claim 5, wherein B₂ is

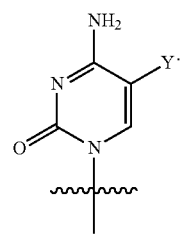

8. The oligonucleotide of claim 1, wherein B₁ is adenine, guanine,

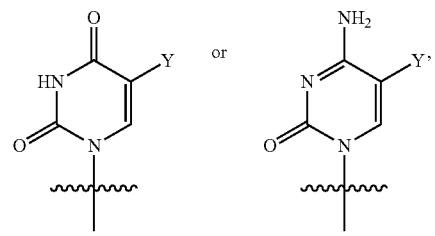

wherein Y is H or CH₃.

9. The oligonucleotide of claim 8, wherein B₁ is adenine.

10. The oligonucleotide of claim 8, wherein B₁ is guanine.

11. The oligonucleotide of claim 1, wherein B₁ is

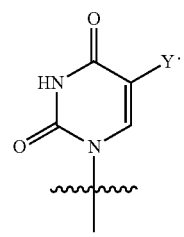

12. The oligonucleotide of claim 1, wherein B₁ is

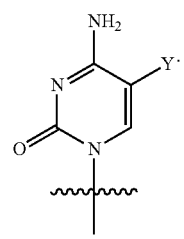

13. The oligonucleotide of claim 1, wherein the nucleosidic end cap is a compound selected from the group consisting of:
1
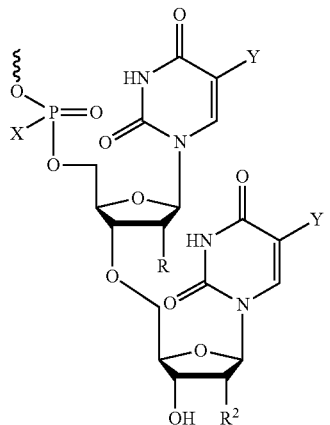
2
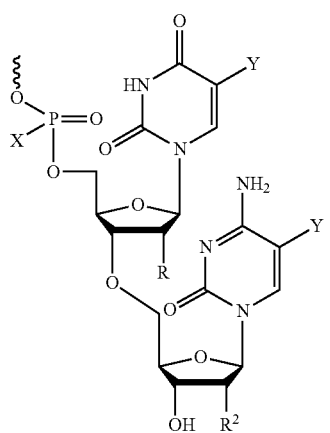
3
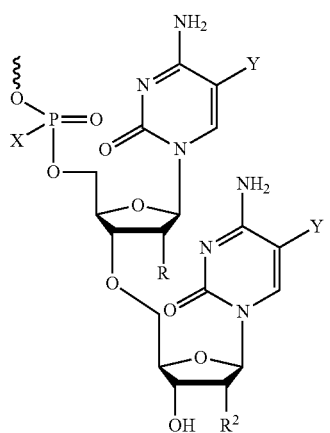
4
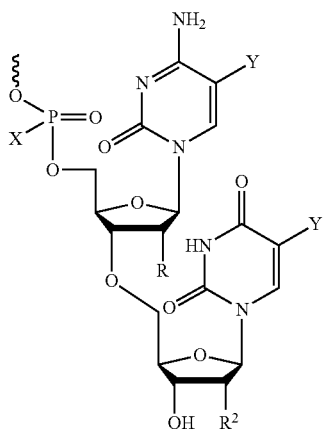
5
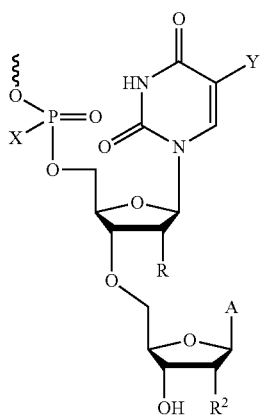
6
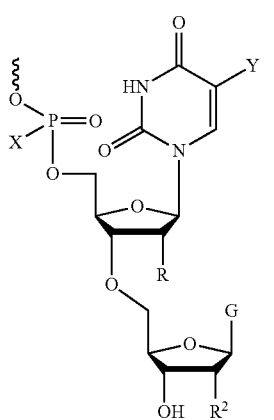

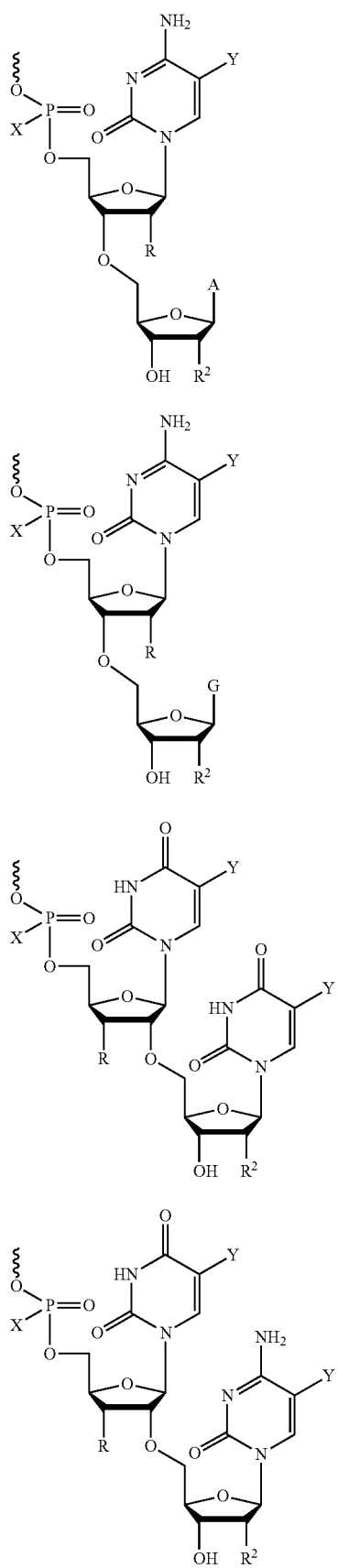
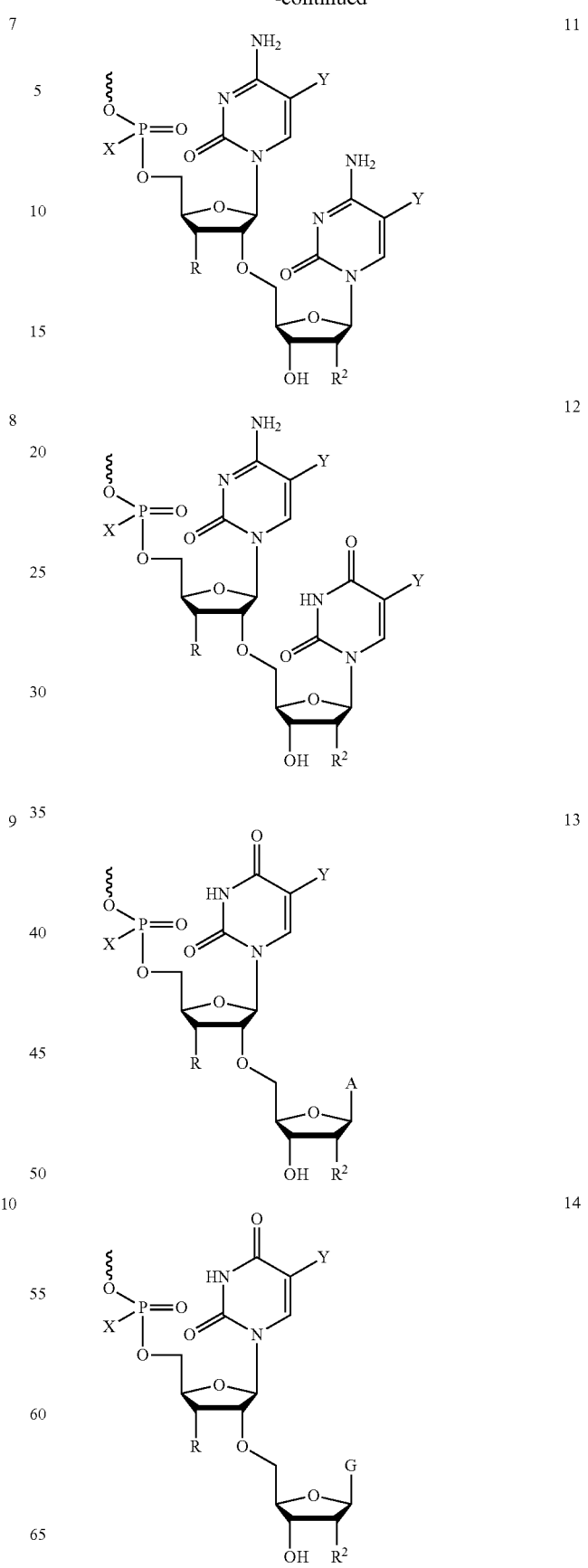

103
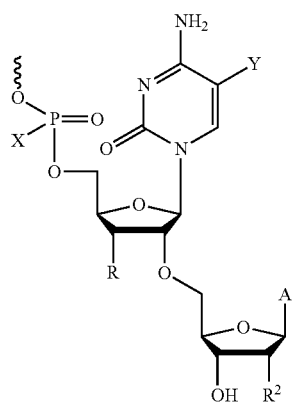
and
104
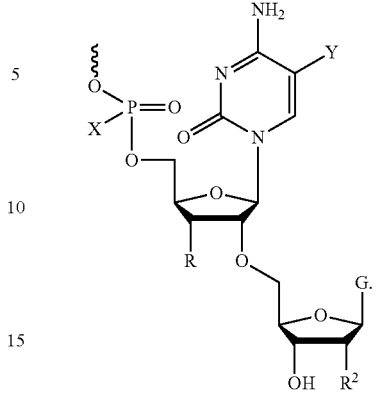
* * * * *

UNITED STATES PATENT AND TRADEMARK OFFICE
CERTIFICATE OF CORRECTION

PATENT NO. : 10,385,337 B2
APPLICATION NO. : 15/334019
DATED : August 20, 2019
INVENTOR(S) : Muthiah Manoharan and Kallanthottathil G. Rajeev It is certified that error appears in the above-identified patent and that said Letters Patent is hereby corrected as shown below:

In the Claims

In Claim 1, Column 97, between Lines 25 and 33, the formula should appear as follows:

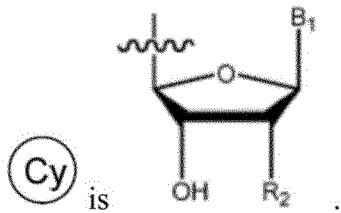 is

In Claim 2, Column 97, Line 38, that portion of the formula reading:
-[O(CH$_2$)$_r$]$_m$-$_{OR}$$^b$, Should read:
-[O(CH$_2$)$_r$]$_m$-OR$^b$, Signed and Sealed this
Twenty-sixth Day of November, 2019

Andrei Iancu
*Director of the United States Patent and Trademark Office*